United States Patent
Liotta et al.

(12) 
(10) Patent No.: US 6,610,835 B1
(45) Date of Patent: Aug. 26, 2003

(54) SPHINGOLIPID DERIVATIVES AND THEIR METHODS OF USE

(75) Inventors: Dennis C. Liotta, McDonough, GA (US); Alfred H. Merrill, Jr., Stone Mountain, GA (US); Thomas E. Keane, Dunwoody, GA (US); Kapil N. Bhalla, Atlanta, GA (US); Eva M Schmelz, Atlanta, GA (US)

(73) Assignee: Emory University, Atlanta, GA (US)

(*) Notice: Subject to any disclaimer, the term of this patent is extended or adjusted under 35 U.S.C. 154(b) by 0 days.

(21) Appl. No.: 09/249,211

(22) Filed: Feb. 12, 1999

(Under 37 CFR 1.47)

Related U.S. Application Data

(60) Provisional application No. 60/074,536, filed on Feb. 12, 1998.

(51) Int. Cl.$^7$ .............................................. C07H 15/06
(52) U.S. Cl. ...................... 536/4.1; 536/17.2; 536/17.9; 536/18.2
(58) Field of Search ................. 536/4.1, 18.2, 536/17.2, 17.9

(56) References Cited

U.S. PATENT DOCUMENTS

| | | | |
|---|---|---|---|
| 5,103,002 A | | 4/1992 | Wieland |
| 5,110,987 A | | 5/1992 | Liotta et al. |
| 5,122,450 A | * | 6/1992 | Feizi et al. ................. 435/7.2 |
| 5,190,876 A | | 3/1993 | Merrill |
| 5,232,837 A | | 8/1993 | Merrill et al. |
| 5,430,169 A | | 7/1995 | Boumendjel et al. |
| 5,440,012 A | * | 8/1995 | Takei et al. ................. 530/307 |
| 5,459,057 A | | 10/1995 | Merrill et al. |
| 5,463,092 A | | 10/1995 | Hostetler et al. |
| 5,488,166 A | | 1/1996 | Hudlicky |
| 5,518,879 A | | 5/1996 | Merrill et al. |
| 5,599,914 A | | 2/1997 | Wiegand et al. |
| 5,610,040 A | | 3/1997 | Smeets et al. |
| 5,616,577 A | * | 4/1997 | Nambi et al. ................. 514/215 |
| 5,635,536 A | | 6/1997 | Lyons |
| 5,672,693 A | * | 9/1997 | Kawahara ................. 536/17.9 |
| 5,780,441 A | * | 7/1998 | Higa et al. ................. 514/25 |
| 5,910,425 A | | 6/1999 | De Boer et al. |
| 5,916,911 A | | 6/1999 | Shayman et al. |
| 6,010,733 A | * | 1/2000 | Takemoto et al. ........... 426/548 |
| 6,043,218 A | * | 3/2000 | Dix ............................. 514/12 |
| 6,063,796 A | * | 5/2000 | Yang et al. ................. 514/322 |

FOREIGN PATENT DOCUMENTS

| | | | |
|---|---|---|---|
| EP | 556962 | * | 8/1993 |
| EP | 560267 | * | 9/1993 |
| EP | 666268 | * | 9/1995 |
| EP | 0 821 068 A | | 1/1998 |
| JP | 1-93562 | * | 4/1989 |
| WO | WO 97 10817 | | 3/1997 |
| WO | WO 97 26891 | | 7/1997 |

OTHER PUBLICATIONS

Waddell, S. et al "Chimeric azalides with functionalized western portions" Heterocycles vol 43, No 11, pp. 2325, 1996.*
Kennedy, K. et al "Asymmetric Synthesis of non–natural homologues of lysine" Bioorg. Med. Chem. Lett. vol 7, No 14, pp 1937–1940, 1997.*
Caplus abstract of Babu et al WO 97/47194, 1997.*
Wipf, P. et al "Solid–phase synthesis of peptide mimetics . . . " J. Org. Chem. vol 62, pp 1586–1587, 1997.*
Caplus abstract of Al–Obeidi et al, WO 95/29189, 1995.*
Caplus abstract of Hunt, EP 675112, 1995.*
Suzuki, N. et al "Farnesyltransferase inhibitors induce cytochrome c release . . . " Proc. Natl. Acad. Sci. vol 95, pp. 15356–15361, 1998.*
Carter, S. et al "Enzymatic sulfation of mucus glycoprotein in gastric mucosa" J. Biol. Chem. vol 263, No 24, pp 11977–11984, 1988.*
Caplus abstract of Feizi et al WO 87/02777, 1987.*
Schmitz, B. et al "Determination of structural elements of the L2/HNK–1 carbohydrate epitope required for its function" Glycoconjugate J. vol 11, No. 4, pp 345–352, 1994.*
Bennun et al., *Infect. & Immun.*, 57:969–74, 1989.
Bell, R., et al. *Cold Spr. Harbor Sym. Quant. Biol*. 53:103, 1988.

(List continued on next page.)

*Primary Examiner*—James O. Wilson
*Assistant Examiner*—Leigh C. Maier
(74) *Attorney, Agent, or Firm*—King & Spalding LLP; Sherry M. Knowles

(57) ABSTRACT

Derivatives of sphingolipids of the formula:

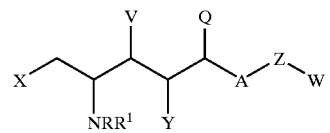

are provided wherein the substituents are as defined in the specification and wherein there is at least one $R^2$ substituent in the sphingolipid derivative. The compounds are useful in the treatment of of abnormal cell proliferation, including benign and malignant tumors, the promotion of cell differentiation, the induction of apoptosis, the inhibition of protein kinase C, and the treatment of inflammatory conditions, psoriasis, inflammatory bowel disease as well as proliferation of smooth muscle cells in the course of development of plaques in vascular tissue. The invention also includes a method for triggering the release of cytochrome c from mitochondria that includes administering an effective amount of a sphingolipid or its derivative or prodrug to a host in need thereof. Further, the invention provides a method for treating bacterial infections, including those that influence colon cancer and other disorders of the intestine, that includes administering an effective amount of one of the active compounds identified herein.

42 Claims, 16 Drawing Sheets

OTHER PUBLICATIONS

Buehrer and Bell, *Adv. Lipid Res* . 6:59–67, 1993.
Farkas–Himsley et al., *Proc. Natl. Acad. Sci.* (USA) 92:6996–7000, 1995.
Hakomori,, *J. Biol. Chem* . 265:18713–18716, 1990.
Hannun et al., *J. Bio. Chem* . 261:12604–12609, 1986.
Hannun, *J. Biol. Chem* . 269:3125–3128, 1994.
Hannun and Obeid, *Trends Biochem. Sci.* 20:73–77, 1995.
*J. Urol.*, 155(5):653A, Abst. 1367, 1996.
Jacewicz et al., *J. Clin. Invest.* 96:1328–1335, 1995.
Jefferson, A. and Schulman, H., *J. Biol. Chem.* 263:15241, 1988.
Karlsson, K. A., *Chem. Phys. Lipids* , 5:6–43, 1970.
Kawai, G. et al., "Stimulatory effect of certain plant sphingolipids on fruiting of Schizophyllum commune," *J. of Biol. Chem.*, 261(2), 1986 779–784.
Keusch et al., *Infect. & Immun* . 63: 1138–1141; 1995.
Kolesnick, *Cell* 77:325–328, 1994.
Merrill et al., Fungal Lipids (R. Prasad and M. Ghanoum, eds.), CRC Press, Boca Raton, FL, 1995a.
Merrill and Wang, *Methods Enzymol,*. 209:427–437, 1992.
Merrill et al., *J. Biol. Chem* . 261:3764–3769, 1986.
Merrill & Sweeley, " Sphingolipids: metabolism and cell signalling," *New Comprehensive Biochemistry: Biochemistry of Lipids, Lipoproteins, and Membranes* , (Vance, D.E. & Vance, J.E., eds.), pp. 309–338, Elsevier Science, Amsterdam, 1996.
Minn, A. J., et al., *Blood* 86: 1903–1910, 1995.
Minn, A. J., et al., *Nature* , 385:353–357, 1997.
Morrison, Biochim. Biophys. Acta., 176:537–546, 1969.
Muchmore, S. W., et al., *Nature* , 381: 335–341, 1996.
Nilsson, A., *Biochim. Biophy. Acta* . 164:575–584, 1968.
Patent Abstracts of Japan, vol. 095, No. 002, Mar. 31, 1995.
Pittet, D., et al., *J. Biol. Chem* . 262:10072, 1987.
Robson et al., *J. Lipid Res* . 35:2060–2068, 1994.
Schmelz et al., *Journal of Nutrition* . 124; 702–712.
Thompson, et al., *Biochem. Pharmacol* . 56: 591–597, 1998.
Wells, G. B. and Lester, R.L., *J. Biol. Chem.* , 258:10200–10203, 1983.
Wilson et al., *J. Biol. Chem.* 261:12616–12623, 1986.
Winicov, I. and Gershengorn, M., *J. Biol. Chem* . 263:12179, 1988.
Wu et al., *J. Biol. Chem* . 268:13830–13837, 1993.

\* cited by examiner

FIG. 3A

| Sphingolipid | | Examples of Biological Activities |
|---|---|---|
| 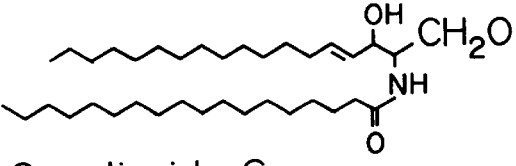 Ganglioside $G_{M3}$ | | Inhibition of EGF Receptor kinase; Inhibition of Cell Growth |
| 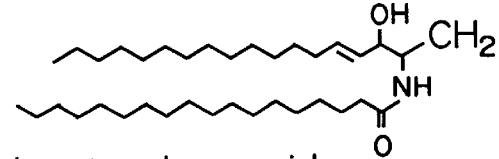 Lactosylceramide | | Stimulation of Cell Growth |
| 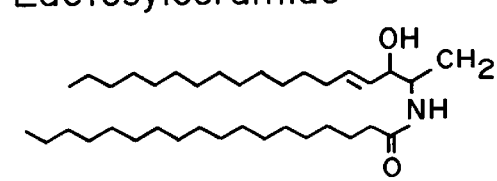 Sphingomyelin | | Inhibition of colon carcinogenesis; Interaction with Cholesterol; Source of Ceramide via Sphingomyelinase |
| 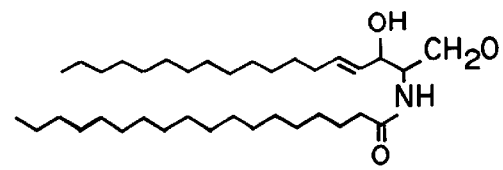 Ceramide | | Activation of Protein Phosphatase(s); Inhibition of Cell Growth; Induction of Apoptosis, Differentiation; Mediator of Cellular Responses to: TNF, IL1 & Gamma Interferon |
| 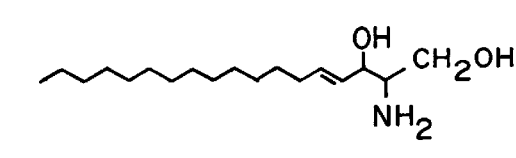 Sphingosine | | Inhibition of Protein kinase C, Na+/K+ ATPase Phosphatidic Acid Phosphatase; Activation of Phospholipase C & D, EGF Receptor Phosphorylation, Protein kinase(s); Inhibition of Cell Transformation, ODC Induction, Tumor Invasion/Metastasis; Stimulation/Inhibition of Growth/Differentiation |

CONTINUED ON FIG. 3B

Sphingosine 1-phosphate

{ Activation of Phospholipase D
Release of Intracellular Calcium
Stimulation of Cell Growth Sphingosine Fumonisin B₁

Fumonisin B₂

Fumonisin B₃

Fumonisin B$_4$

Alternaria toxins (AAL toxins)

$R_1 = H$ OR $R$ $R = COCH_2CH(COOH)CH_2COOH$

Fumonisin Analogs

FIG. 5B

Reagents and conditions: (a) iPr$_2$NP(OMe)Cl/Et$_3$N/CH$_2$Cl$_2$; (b) Choline tosylate/Tetrazole/MeCN/THF; (c) t-BuOOH/MeCN; (d) t-BuNH$_2$/CH$_2$Cl$_2$; (e) MeONa/MeOH

SPHINGOLIPID DERIVATIVES AND THEIR METHODS OF USE

This application claims priority to U.S. provisional application No. 60/074,536, filed on Feb. 12, 1998.

The U.S. government has rights in this invention arising out of funding by federal grant nos. GM46368 and CA61820 from the National Institutes of Health.

This application is in the area of pharmaceutical chemistry, and in particular includes sphingolipid derivatives, prodrugs and pharmaceutical compositions and salts thereof for the treatment of abnormal cell proliferation, including benign and malignant tumors, the promotion of cell differentiation, the induction of apoptosis, the inhibition of protein kinase C, and the treatment of inflammatory conditions, psoriasis, inflammatory bowel disease as well as proliferation of smooth muscle cells in the course of development of plaques in vascular tissue. The invention also includes a method for triggering the release of cytochrome c from mitochondria that includes administering an effective amount of a sphingolipid or its derivative or prodrug to a host in need thereof. Further, the invention provides a method for treating bacterial infections, including those that influence colon cancer and other disorders of the intestine, that includes administering an effective amount of one of the active compounds identified herein.

BACKGROUND OF THE INVENTION

Sphingosine is the common name for D-erythro-4-trans-sphinganine, the prevalent long-chain base of most mammalian sphingolipids. It most often has 18 carbon atoms and the stereochemistry shown in FIG. 1. Sphingolipids generally are composed of a long-chain (sphingoid) base (sphingosine, sphinganine, 4-hydroxysphinganine, or a related compound) as the backbone moiety (Karlsson, K. A. *Chem. Phys. Lipids*, 5:6–43, 1970), which is usually modified by an amide-linked long-chain fatty acid (for ceramides), and a head group at position 1, as illustrated in FIG. 2. Over 300 classes of sphingolipids are known, most of which have head groups with simple to complex carbohydrates (see Merrill & Sweeley, *New Comprehensive Biochemistry: Biochemistry of Lipids, Lipoproteins, and Membranes*, (Vance, D. E. & Vance, J. E., eds.), pp. 309–338, Elsevier Science, Amsterdam, 1996). It is a common misconception from the names of these compounds (e.g., ceramide, sphingomyelin, gangliosides, etc.) that sphingolipids are only found in neuronal tissues. In fact, sphingolipids are major constituents of all eukaryotic (and some prokaryotic) organisms, including plants (Lynch, D. V., *Lipid Metabolism in Plants* (T. S. Moore, Jr., ed.), pp. 285–308, CRC Press, Boca Raton, Fla. 1993). This nomenclature merely reflects their initial discovery in brain tissues by classic studies a century ago (Thudichum, J. L. W., *A Treatise on the Chemical Constitution of Brain*, Bailliere, Tindall & Cox, (London) 1884).

Mammalian sphingolipid compounds typically vary in the presence or absence of: (I) the 4,5-trans-double bond (for example, sphingosine has a double bond whereas sphinganine (also referred to as dihydrosphingosine) does not); (ii) double bond(s) at other positions, such as position 8; (iii) a hydroxyl group at position 4 (D-1-hydroxyphinganine, also called "phytosphingosine") or elsewhere (Robson et al., *J. Lipid Res.* 35:2060–2068, 1994); (iv) methyl group(s) on the alkyl side chain or on the amino group, such as N,N-dimethylsphingosine; and (v) acylation of the amino group (for example ceramide (also referred to as N-acylsphingosine), and dihydroceramide (also referred to as N-acyl-sphinganine)). The 4-hydroxysphinganines are the major long-chain bases of yeast (Wells, G. B. and Lester, R. L., *J. Biol. Chem.*, 258:10200–10203, 1983), plants (Lynch, D. V., *Lipid Metabolism in Plants* (T. S. Moore, Jr., ed.), pp. 285–308, CRC Press, Boca Raton, Fla. 1993), and fungi (Merrill et al., *Fungal Lipids* (R. Prasad and M. Ghanoum, eds.), CRC Press, Boca Raton, Fla. 1995a), but are also made by mammals (Crossman and Hirschberg, *J. Biol. Chem.* 252:5815–5819, 1977). Other modifications of the long-chain base backbone include phosphorylation at the hydroxyl oxygen of carbon 1 (Buehrer and Bell, *Adv. Lipid Res.* 6:59–67, 1993), and acylation (Merrill and Wang, *Methods Enzymol.*, 209:427–437, 1992) (Igarashi and Hakomori, *Biochim. Biophys. Res. Commun.* 164:1411–1416, 1989; Felding-Habermann et al., *Biochemistry* 29:6314–6322, 1990) of the amino group. Each of these compounds can be found in various alkyl chain lengths, with 18 carbons predominating in most sphingolipids, but other homologs can constitute a major portion of specific sphingolipid (as exemplified by the large amounts of $C_{20}$ sphingosine in brain gangliosides) (Valsecchi et al., *J. Neurochem.*, 60:193–196, 1993) and in different sources (e.g., $C_{16}$ sphingosine is a substantial component of milk sphingomyelin) (Morrison, *Biochim. Biophys. Acta.*, 176:537–546, 1969). One difficulty in studying these compounds is that relatively few are commercially available in chemically-pure form. For example, most of the sphinganine that can be purchased from various vendors is a mixture of the D and L enantiomers (therefore, commercially available dihydroceramides are also mixtures) and the metabolism, and some of the functions, of these compounds are sensitive to stereochemistry (Stroffel and Bister, *Hoppe-Seyler's Z. Physiol. Chem.* 354:169–181, 1973; Buehrer and Bell, *J. Biol. Chem.* 267:3154–3159, 1992; *Adv. Lipid Res.* 26:59–67, 1993; Hauser et al., *J. Biol. Chem.* 269:6803–6809, 1994; Olivera et al., *J. Biol. Chem.* 269:17924–17930, 1994). For example, sphingosine kinase (which forms the signaling compound sphingosine 1-phosphate) will act only on the erythro stereoisomers—the threo stereoisomers are inhibitors of the enzyme (Buehrer and Bell, *J. Biol. Chem.* 267:3154–3159, 1992; *Adv. Lipid Res.* 26:59–67, 1993). Release of intracellular calcium is limited to D-(+)-erythrosphingosine 1-phosphate.

Sphingosines and other long-chain bases are cationic amphiphiles, which distinguishes them from most other naturally occurring lipids, which are neutral (including zwitterionic) or anionic. In the protonated form, they affect the phase behavior of both zwitterionic (Koiv et al., *Chem. Phys. Lipids.* 66:123–134, 1993; López-Garcia et al., *Biochim. Biophys. Acta.*, 1194:281–288, 1994) and acidic (Koiv et al., *Chem. Phys. Lipids.* 66:123–134, 1993; López-Garcia et al., *Biochim. Biophys. Acta.* 1194:281–288, 1994) phospholipids.

The hydroxyl groups at positions 1, 3 and sometimes 4 or 6 are also relevant to the behavior of these compounds. This has mostly been considered from the perspective of how hydrogen bonding in the interfacial region of the bilayer affects membrane structure (Thompson and Tillack, *Annu. Biophys. Chem.*, 14:361–386, 1985). However, in a study of phosphatidic acid phosphatase purified from yeast (Wu et al., *J. Biol. Chem.* 268:13830–13837, 1993), inhibition of this enzyme by long-chain bases showed a considerable preference for phytosphingosine and sphinganine over sphingosine, which matches the types of sphingoid bases found in yeast. Therefore, these functional groups appear to be present both for structural purposes and to allow optimum interaction with cellular targets.

Many microorganisms, microbial toxins and viruses bind to cells via sphingolipids. Specific organisms that have been reported as binding to sphingolipids include cholera toxin (ganglioside GM1) (Thompson, et al., Biochem. Pharmacol. 56:591–597, 1998); verotoxin (globosides) (Farkas-Himsley et al., Proc. Natl. Acad. Sci. (USA) 92:6996–7000, 1995; Bast et al., Infect. & Immun., 57:969–74, 1997); Shiga-like toxin 2e (globotriaosylceramide, Gb3) (Jacewicz et al., J. Clin. Invest. 96:1328–1335, 1995; Keusch et al., Infect. & Immun. 63: 1138–1141; 1995); and Clostridium botulinum type B neurotoxin (to synaptotagmin II associated with gangliosides GT1b/GD1a) (Nishiki et al., FEBS Lett. 378: 253–257, 1996).

Furthermore, many bacteria utilize sphingolipids to adhere to cell. Examples known in the art include *Escherichia coli* (galactosylceramide) (Blomberg et al., Infect. & Immun. 61: 2526–2531, 199; Payne et al., Infect. & Immun. 61: 3673–3677, 1993; Khan et al., Infect. & Immun. 64: 3688–3693, 1996); *Haemophilus influenzae* (gangliotetraosylceramide and gangliotriosylceramide) (Hartmann et al., Infect. Immun. 65: 1729–1733, 1997); *Helicobacter pylori* (gangliotetraosylceramide, gangliotriaosylceramide, sulfatides and GM3) (Huesca et al., Infect. & Immun. 64: 2643–2648, 1996; Kamisago et al., Infect. & Immun. 64:624–628, 1996; Simon et al., Infect Immun. 65: 750–757, 1997; Wadstrom et al., Curr. Microbiol. 34: 267–272, 1997); *Borrelia burgdorferi* (galactocerebroside; Virulent strain 297; glycosylceramide, lactosylceramide, and galactosylgloboside) (Garcia Monco et al., Neurology 42:1341–1348, 1992; Kaneda et al., Infect. & Immun. 65: 1138–1141, 1997); and *Pseudomonas aeuroginosa* and *Candida albicans* (asialo GM1) (Yu et al., Infect. & Immun. 62: 5213–5219, 1994).

Virus binding can be mediated via sphingolipids, including HIV-1 gp120 (galactosylceramide) (Fantini et al., J. Biol. Chem. 272: 7245–7252, 1997), Sendai virus (ganglioside GD1a) (Epand et al., Biochemistry 34: 1084–1089, 1995); and influenza viruses (gangliosides, sulfatides and polyglycosylceramides) (Fakih et al., Infect. & Immun. 65: 1695–1700, 1997; Matrosovich et al., Virology 233: 224–234, 1997; Matrosovich et al., Virology 223: 413–416, 1996; Sato et al., Biochim. Biophys. Acta 1285: 14–20, 1996; Suzuki et al., Biochim. J. 318:389–393, 1996).

Sphingolipids are significant components of foods. The types of sphingolipids differ among organisms (and for different types of cells within an organism); for examples, the predominant sphingolipid classes for plants are cerebrosides (Lynch, D. V., *Lipid Metabolism in Plants* (T. S. Moore, Jr., ed.), pp. 285–308, CRC Press, Boca Raton, Fla. 1993), ceramide phosphoinositols for yeast (Lester et al., Biochim. Biophys. Acta. 1165:314–320, 1993), and sphingomyelin (plus a wide spectrum of neutral and acidic glycolipids) for mammals (Hakomori, *J. Biol. Chem.* 265:18713–18716, 1983). There are also differences in the nature of the sphingoid-base backbones because plants contain predominantly 4-hydroxysphingenine (t18:1) isomers and 4,8-sphingadienine (d18:2) isomers (Lynch, D. V., *Lipid Metabolism in Plants* (T. S. Moore, Jr., ed.), pp. 285–308, CRC Press, Boca Raton, Fla. 1993), ceramide phosphoinositols for yeast (Lester et al., *Biochim. Biophys. Acta.*, 1165:314–320, 1993). Furthermore, considerable structural diversity exists among the sphingoid base (and fatty acid) composition of glucocerebrosides isolated from different plant tissues. Sphingoid bases with a double bond at position 8 have been seen in mammalian sphingolipids (Karlsson, K. A., *Chem. Phys. Lipids*, 5:6–43, 1970), but have never been shown to be synthesized by mammalian cells; therefore, it is likely that they are acquired by mammals by consumption of plant sphingolipids.

Sphingolipids not only help define the structural properties of membranes, but also play important roles in cell—cell and cell-substratum interactions, and help regulate growth and differentiation by a variety of mechanisms, such as inhibition of growth factor receptor kinases and effects on numerous cellular signal transduction systems (for reviews see Hakomori, *J. Biol. Chem.* 265:18713–18716, 1991; Bell et al., *Advances in Lipid Research: Sphingolipids and Their Metabolites,* vols. 25 and 26, Academic Press, Sand Diego, 1993; Merrill and Sweeley, *New Comprehensive Biochemistry: Biochemistry of Lipids, Lipoproteins, and Membranes* (Vance, D. E. & Vance, J. E., eds.), 1996; Spiegel and Merrill, *FASEB J* 10, 1388–1397, 1996). The backbones of dietary sphingolipids (ceramides and sphingoid bases) are assumed to induce cellular responses that are normally regulated by intracellular sphingolipid second messengers. This may have implications far beyond just their effects on carcinogenesis, such as restenosis, where there is proliferation of smooth muscle cells in the course of development of plaques in vascular tissue, and closing off of the artery after angioplasty.

Interest in these lipid backbones as bioactive compounds began when Hannun, Loomis and Bell at Duke University serendipitously discovered that sphingosine is a potent inhibitor of protein kinase C in vitro (Hannun et al., *J. Bio. Chem.* 261:12604–12609, 1986), and by the finding that sphingoid bases also inhibit diverse cell functions requiring protein kinase C (Hannun et al., *J. Bio. Chem.* 261:12604–12609, 1986; Wilson et al., *J. Biol. Chem.* 261:12616–12623, 1986; Merrill et al., *J. Biol. Chem.* 261:12610–12615, 1986). Subsequent studies have found that sphingosine activates and inhibits several protein kinases, and affects a large number of signal transduction systems. Researchers thereafter uncovered additional bioactive sphingolipid "backbones" such as ceramides (Hannun, *J. Biol. Chem.* 269:3125–3128, 1994; Kolesnick, *Cell* 77:325–328, 1994), sphingosine 1-phosphate (Zhang et al., *J. Cell Biol.* 114:155–167, 1991; Spiegel et al., *J. Lipid Mediators* 8:169–175, 1993), and N-methyl-sphingosines (Igarashi, *J. Biol. Chem.* 265:5385–5389, 1990). As the cellular targets of these compounds have been studied, they have turned out to be as complex as for other lipid-signaling pathways in cells, i.e., they involve activation and inhibition of protein kinases, phosphoprotein phosphatases, ion transporters, and "cross-talk" with other signaling pathways.

The current paradigm for the action of sphingolipids in cell regulation is that complex sphingolipids are important in membrane structure, especially specialized membrane functions such as are found in calveolae. They also interact with cell surface receptors for growth factors, and the extracellular matrix. The lipid backbones (ceramide, sphingosine and sphingosine 1-phosphate) function as "second messengers" to affect protein kinases, phosphoprotein phosphatases, ion transporters, and other regulatory machinery, as illustrated in FIG. 3. As examples, tumor necrosis factor-α, interleukin 1β, and nerve growth factor induce sphingomyelin hydrolysis to ceramide as a second messenger (Hannun, *J. Biol. Chem.* 269:3125–3128, 1994; Kolesnick, *Cell* 77:325–328, 1994); other agonists, such as platelet-derived growth factor, trigger further hydrolysis of ceramide to sphingosine, and activate sphingosine kinase to form sphingosine 1-phosphate (Olivera and Speigel, Nature 365:557–560, 1993; Coroneos et al., *J. Biol. Chem.* 270:23305–23309, 1995). Depending on the cell type, these metabolites can either stimulate or inhibit growth. While the details of growth regulation by ceramide, sphingosine, and sphingosine 1-phosphate are still being uncovered (Spiegel and Merrill, *FASEB J.*, 1996), depending on the system, it appears to involve calcium mobilization from intracellular stores, and activation of the MAP (and Jun) kinase pathways and transcription factors (AP1) (Su et al., *J. Biol. Chem.* 269:16512–16517, 1994), induction of retinoblastoma protein dephosphorylation (Pushkareva et al., *Biochemistry*, 34:1885–1892, 1995), and in some cases, induction of apoptosis (Obeid et al., *Science*, 259:1769–1771, 1993; Jarvis et al., *Cancer Res.* 54:1707–1714, 1994).

Carcinogenesis involves progressive genetic mutations leading to the loss of cell growth regulation and, as importantly, loss of regulation of programmed cell death (apoptosis). The genetic abnormalities have been studied extensively for colorectal cancer and include activation of oncogenes and loss of tumor suppressor genes as cells progress from early premalignant lesions to carcinomas (Fearon and Vogelstein, 1990; Jen et al., 1994; Kinzler and Vogelstein, 1996), and a progressive inhibition of apoptosis (Bedi et al., 1995).

It has been determined that free sphingoid bases and ceramide, through inhibition of protein kinase C (Hannun et al., *J. Biol. Chem.* 261:12604–12609, 1986; Stevens et al., *Biochem. Biophys. Acta* 1051:37–45, 1990a) or induction of retinoblastoma protein dephosphorylation (Pushkareva, *Biochemistry* 34:1885–1892, 1995; Obeid & Hannun, *Trends Biochem. Sci.* 20:73–77, 1995) can inhibit cell growth; sphingoid bases (Stevens et al., *Cancer Res.* 50:222–226, 1990b) and ceramide (Okazaki et al., *J. Biol. Chem.* 265:15823–15831, 1990) can promote cell differentiation; and, ceramide (Obeid et al., *Science* 259:1769–1771, 1993; Hannun and Obeid, *Trends Biochem. Sci.* 20:73–77, 1995; Kolesnick and Fuks, 1995) as well as sphingosine (Ohta et al., *Cancer Res.* 55:691–697, 1995) can induce apoptosis, apparently through suppression of Bcl-2 (Sakakura et al., *FEBS Lett.* 379:177–180, 1996; Chen et al., *Cancer Res.* 55:991–994, 1995). Wright et al. (*FASEB J* 10:325–332, 1996) have recently reported that U937 cells that were isolated based on their resistance to TNF-induced apoptosis have a defect in the activation of sphingomyelinase and the 24 kDa apoptotic protease (AP24); furthermore, this also makes the cells resistant to UV-induced apoptosis. This raises the possibility that some tumors could be defective in apoptosis because they have mutation(s) in upstream regulators of sphingomyelin turnover to ceramide. If so, addition of exogenous ceramide (and/or sphingosine or synthetic analogs of either) might bypass this (these) defects.

There have been few studies of the relevance of these compounds to carcinogenesis. Several years ago, it was explored whether free sphingoid bases could inhibit transformation using C3H 10T1/2 cells initiated by γ-irradiation or chemical carcinogens as a model system (Borek et al., *Proc. Natl. Acad. Sci. USA* 88:1953–1957, 1991; Borek and Merrill, *Antimutagenesis and Anticarcinogenesis Mechanisms III* (G. Bronzetti et al. eds., Plenum Publishing Corp., New York), 1993). These studies showed that sphingosine and sphinganine completely blocked "promotion" of transformed foci by phorbol esters, and reduced the number of transformed foci in cells treated with just γ-irradiation. The sphingoid bases were added at levels that affected protein kinase C but were not noticeably cytotoxic; therefore, the effects were not due to non-specific killing by a lipid "detergent."

In another study, female CF1 mice (6 weeks of age, 10 mice per group) were fed a standard, defined diet (AIN76A) (without sphingolipid supplementation), then treated with 1,2-dimethylhydrazine (DMH) in 6 weekly injections (40 mg/kg). One week after the last DMH administration, some of the mice were changed to diets supplemented with 0.05% sphingomyelin, and analyzed on week 7 for aberrant colonic crypts (McLellan et al. *Cancer Res.* 51:5270–5274, 1991; Pretlow et al., *Cancer Res.* 51:1564–1567, 1991). Sphingomyelin caused a significant (50%) reduction in the number of aberrant colonic crypts induced by DMH (Dillehay et al., *J. Nutr.* 124:615–620, 1994). All of the aberrant crypts were found in the distal third of the colon.

Aberrant colonic crypt foci are one of the earliest morphological changes of colonic cells to dysplasia. It is thought that some of these lesions will eventually develop into adenomas and carcinomas (McLellan & Bird, *Cancer Res.* 51:5270–5274, 1991; Pretlow et al., *Cancer Res.* 51:1564–1567, 1991; Bruce et al., *Mutat. Res.* 290:111–118, 1993; Toribara and Sleisenber, 1995), which makes aberrant crypt foci a useful biomarker for studies of agents that may inhibit (or enhance) colon carcinogenesis. The effect of sphingomyelin on DMH-induced carcinogenesis was evaluated in a pilot experiment (15 mice per group) conducted with milk sphingomyelin, and a larger experiment (40 mice per group) with buttermilk sphingomyelin. Mice fed sphingomyelin has about half of the tumor incidence of the control. A control group fed sphingomyelin, but not treated with DMH, had not signs of a deleterious effect of consumption of sphingolipids, and developed no tumors.

A second study with buttermilk sphingomyelin gave a somewhat different, but nonetheless very interesting result. There was no reduction in the number of overall tumors, but histological analyses revealed that mice fed sphingomyelin had a shift in tumor type such that there were more adenomas versus adenocarcinomas than for the control (defined as polypoid adenomas by the presence of an intact muscularis mucosa versus invasion of neoplastic cells through the muscularis mucosa, which is characteristic of adenocarcinomas.

The first studies of sphingolipid digestion were published by Nilsson approximately 30 years ago (Nilsson, A., *Biochim. Biophy. Acta.* 164:575–584, 1968; *Biochim. Biophys. Acta* 187: 113–121, 1969) and indicated that sphingomyelin was metabolized in the small intestine and up to 30% of the radiolabel could be recovered in lymph. However, 21 to 46% of the radiolabel was found in feces, mainly as ceramide, which indicated that the digestion of sphingomyelin is not very efficient, but may continue in the lower bowel (probably with the involvement of intestinal microflora). Secondly, the time course for the absorption of radiolabel was somewhat curious, with peak absorption 10 hours after feeding the sphingolipid, which may indicate that coprophagy had occurred. A similar study with the glycolipids glucosylceramide and galactosylceramide (Nilsson, *Biochim. Biophy. Acta.* 164: 575–584, 1969) found that glycolipids are also only partially digested.

Follow-up studies of sphingolipid digestion by rats and mice were conducted using several approaches (Schmelz et al., *Journal of Nutrition*, 124: 702–712, 1994). The first is a simpler model, the use of isolated segments of the intestine in which the animal is anesthetized and the intestines are flushed, tied-off, and then injected with the radio labeled compound of interest. The advantage of this technique is that the intestine retains most of its normal blood supply, and nutrient absorption can be fairly simply assessed by the disappearance of the radiolabel (or appearance in the tissue or blood). When [$^3$H-sphingosyl]sphingomyelin was added to segments of the jejunum, ileum, and caecum, or colon, very little radiolabel was lost from the segments; radiolabel became associated with the tissue in a form that was not removed by washing. It was found that the [$^3$H-sphingosyl] backbone had been incorporated into other classes of sphingolipids. This established that the sphingolipid had undergone some hydrolysis, cellular uptake and metabolism. It is not known whether hydrolysis occurred before or after cellular uptake, and subsequent double labeling experiments have indicated that both the [$^3$H-sphingosyl]backbone and [$^{14}$C] choline head group are taken up.

In a second approach (Schmelz et al., *Journal of Nutrition*. 124; 702–712, 1994), [$^3$H-sphingosyl]-sphingomyelin was given to mice by gavage, and then the animals were killed after different time intervals and the amount of radiolabel in different intestinal segments measured. From 3 to 5% of the radiolabel had progressed into the colon within about 2 hours, which confirmed the earlier observation by Nilsson (*Biochim. Biophys. Acta.,* 164: 575–574, 1968) that at least some sphingomyelin escapes digestion by the upper intestine and arrives in the colon. About 5% of the label appeared in liver, sphingolipids, so there is some uptake of the sphingoid base from the diet, and incorporation into the tissues of the animal. The lack of an effect on weight gain was important because carcinogenesis studies would be more difficult to interpret if sphingolipids had affected growth (Birt et al., 1992).

Current knowledge about sphingolipids and the recent findings summarized above establish four points. First, sphingolipids, and especially sphingosine and ceramide, are highly bioactive compounds with potential to serve as naturally occurring modulators of diverse cell behaviours that include neoplastic transformation. Second, findings in various cell culture systems and animal models for carcinogenesis suggest strongly that sphingolipids suppress carcinogenesis. Third, glycosphingolipids may be more effective than phosphosphingolipids because when they are hydrolyzed to a lysosphingolipid (such as psychosine for cerebrosides) the product is also cytotoxic, in contrast to lysosphingomyelin, which is mitogenic. As a result, they may be selectively cleaved in the lower GI track. Fourth, based on the above-described dietary studies, only a small amount of orally administered sphingolipid survives to the lower intestine, and logically, to other distant sites of the body which might be in need of treatment.

U.S. Pat. Nos. 5,232,837 and 5,518,147 issued to Merrill, Wong, and Riley disclose a method of altering the metabolism of sphingolipids in a cell comprising exposure of the cell to fumonisins, or an analog thereof. Fumonisins (see FIGS. 5 & 6) are a family of mycotoxins produced by *Fusarium moniliforme* and related fungi that are common contaminants of maize, sorgum, and related grains. Fumonisins and sphingosine share a 2-amino-3-ol head group and possess backbone carbon chains of approximately equal size. However, sphingosine is hydroxyl-substituted at carbon 1 while fumonisin $B_1$ and $B_2$ are hydroxyl-substituted at carbon 5. In addition, the fumonisins possess polycarboxylate moieties attached to the tail of the backbone carbon chain. Similarities between sphingosine and Fumonisin in their head groups and tails are responsible for the activity of the fumonisins. It was discovered that fumonisin acts as an inhibitor of ceramide synthase, and thus alters the metabolism of the conversion of sphinganine to dihydroceramide.

An abstract published in *J. Urol.,* 155(5):653A, Abst. 1367, 1996, disclosed that the administration of fumonisin in combination with doxirubicin exhibited a striking ability to treat renal cell carcinoma. This abstract showed that Fumonisin B has cytostatic activity using the Soft Agar thymidine incorporation in vitro assay model of human carcinomas against renal bladder and colon cancer cell lines. It confirmed that Fumonisin B can augment the cytotoxicity of other cytotoxic agents in this model system.

U.S. Pat. No. 5,190,876 and U.S. Pat. No. 5,459,057 to Merrill, Kinkade, and Stevens, disclose a method and composition for enhancing the action of biological response modifiers, such as promoting cellular differentiation, by administration of an effective amount of Vitamin A or an analog thereof with sphingosine or an analog thereof.

U.S. Pat. No. 5,110,987 to Liotta and Merrill discloses a method for preparing sphingosine derivatives.

U.S. Pat. No. 5,635,536 to Lyons discloses emulsions suitable for administration of sphingolipids.

In light of the fact that sphingolipids play a fundamental role in a number of metabolic pathways, including cell proliferation and programmed cell death, it would be of benefit to provide new sphingolipid derivatives that have improved properties, bioavailability, or are targeted to desired locations for effective therapy.

It is therefore an object of the present invention to provide new sphingolipids with biological activity, and in particular, sphingolipids that are useful in the treatment of abnormal cell proliferation, including benign and malignant tumors, the promotion of cell differentiation, the induction of apoptosis, the inhibition of protein kinase C activity, the modification of the colonization of microfora in the body, and the treatment of inflammatory conditions including psoriasis, inflammatory bowel disease as well as proliferation of smooth muscle cells in the course of development of plaques in vascular tissue.

It is therefore an object of the present invention to provide sphingolipids in a prodrug form that can be cleaved to a parent sphingolipid in vivo to increase bioavailability and or efficacy. It is another object of the present invention to provide sphingolipids in a manner that efficiently targets them to a desired location.

It is still another object of the present invention to provide a method and composition that increases the level of sphingolipid that is delivered to a desired location in a host animal.

It is a further object of the present invention to provide new sphingolipid compositions for the treatment of cancer, including colon cancer.

It is yet another object of the present invention to provide new methods for the treatment of bacterial infections.

It is still another object of the present invention to provide new sphingolipid compositions for the modification of the colonization of microfora that influence colon cancer and other intestinal disorders.

SUMMARY OF THE INVENTION

Derivatives of sphingolipids of the formula:

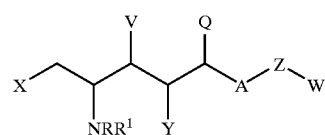

are provided wherein:

A is a spacer group which is $(CH_2)_m$ where m=0–14, where any of the hydrogens may be independently replaced by $R^1$ or X and where any two adjacent carbons may be independently replaced by a $C_3$–$C_8$ cycloalkyl group, a 1,2-, 1,3- or 1,4-disubstituted benzene group, or a 2,3-, 2,4- or 2,5-disubstituted thiophene, furan or pyrrole group;

X, Y, V, and Q are independently hydrogen, $OR^1$, $NR_2$, CN, alkyl, acyl (i.e., C(O)R), carboxylate (i.e., OC(O)R), and wherein alternatively, V and Y, Y and Q or Q and A can together constitute a double or triple bond;

W=no substituent, H, alkyl, aryl, alkenyl, alkynyl, alkaryl, aralkyl, $C(O)(CH_2)_nCO_2H$, $C(O)(CH_2)_nCW'_2CO_2H$, or $OR^1$;

W' is selected independently from H, alkyl, aryl, $(CH_2)_nCO_2H$; $(CH_2)_{n'1}$ $_{CH(CO_2}H)CH_2CO_2H$; and $(CH_2)nCH(CO_2H)CH(CH_2CO_2H)CO_2H$;

Z is H, O, NH, NR, NHC(O), $C(O)OR^1$, C(O)NH, or C(O)NR;

R is selected independently from H, alkyl, acyl, alkenyl, alkynyl, aryl, alkaryl, aralkyl, or heteroaryl;

$R^1$ is R or $R^2$;

$R^2$ is phosphate $(OP(OR_3))$, wherein at least one R is not hydrogen), b-D-galactoside, N-acetyl-b-D-glucosamine, a-D-mannoside, an organic azo-bond containing moiety that can be reduced by an azoreductase, b-D-cellobiosides, b-D-glucopyranosides, b-D-galactopyranosides, b-D-glucuronides, starch (such as maize starch, amylomaize starch, pectin and others found in wheat flour, potato and beans), lactose, raffinose, stachyose, fructooligosaccharides (such as oligofructose and inulin), an amide or ester of b-cyclodextrin, dextran linked via succinate and glutarate, an amino acid or peptide, or a polyamino acid or polypeptide, furanose and pyranose carbohydrates, sulfonate (and esters thereof), phosphocholine, phosphoserine, and phosphoethanolamine;

wherein there is at least one $R^2$ substituent in the sphingolipid derivative.

It has been discovered that biologically important sphingolipids can be administered as prodrugs which increase the level of active compound that is delivered to the active site of interest. The prodrug is cleaved by an appropriate enzyme in vivo to release a parent sphingolipid moiety for desired therapy. Certain derivatives of Formula I are especially suited for treatment of disorders of the lower intestinal tract, including but not limited to colon cancer, intestinal polyps, intestinal tumors, inflammatory bowel diseases including ulcerative colitis and Crohn's disease, necrotizing enterocolitis, and ileocecitis, other inflammations of the lower bowel, and antibiotic associated colitis, as the enzymes which free the sphingolipid from its prodrug form are concentrated in the lower intestine. These prodrugs are resistant to hydrolysis in the upper gastrointestinal tract, and are more readily cleaved in the cecum and the colon. This invention thus addresses the problem to date of low bioavailability of these important compounds at the target site.

In another alternative embodiment of the invention, $R^2$ is a "targeting moiety" that binds to a receptor molecule on the target membrane's surface. Examples of targeting molecules include steroids, hormones (including but not limited to melanin), hormone receptors, cell specific receptors and ligands that bind to cell specific receptors (including but not limited to sugars, proteins, peptides, and glycoproteins), antibodies (for example, the Her 2-Nu antibody for the treatment of breast cancer), antibody fragments (such as the Fab or $Fab_2$ antibody fragments), antigens, T-cell receptor fragments including T-cell receptor variable regions. In one embodiment, a steroid that binds to the membrane of a cancer cell is used as the targeting moiety.

The active compounds are administered in an effective amount to alter sphingolipid metabolism, and thus are useful in the treatment of abnormal cell proliferation, including tumors, cancer, psoriasis, and familial polyposis; in the promotion of cell differentiation, in the induction of apoptosis, in the inhibition of protein kinase C; and in the modification of the colonization of microflora that influence colon cancer and other intestinal disorders, and in the treatment of inflammatory conditions. These compounds either exhibit activity in themselves or act as a prodrug of a parent compound. The compounds can be administered alone or in combination with other biologically active compounds to achieve the desired effect.

These compounds can in particular be used to treat infections caused by bacteria (gram negative and gram positive) and viruses which have receptors for sphingolipids as anchoring means for colonization. Nonlimiting examples of microorganisms that can be treated using this method include cholera toxin, verotoxin, Shiga-like toxin 2e, Clostridium botulinum type B neurotoxin, *Escherichia coli*, *Haemophilus influenzae*; *Helicobacter pylori*; *Borrelia burgdorferi*, *Pseudomonas aeruginosa*, *Candida albicans*, HIV, Sendai virus, and influenza viruses. In this embodiment, an effective amount of a selected compound falling within the above formula is administered to decrease or prevent colonization of the selected microorganism.

In yet another embodiment of the invention, a derivative of a fumonisin is provided that includes at least one covalently bound $R^2$ group. These compounds are also useful in the treatment of abnormal cell hyperproliferation, including cancer and tumors, most notable when used in combination with other antitumor compounds. In particular, the derivatives can be used to target cells, including solid tumors such as colon or urogenital tract tumors including kidney, bladder, prostate, as well as the uterus and cervix, for enhanced therapy.

In yet another embodiment of the invention, sphingolipid derivatives are also useful for the modification of the colonization of microfora that influence colon cancer and other intestinal disorders.

It has also now been discovered that sphingoid bases (including naturally occurring compounds that share this structural motif, such as the fumonisins), including but not limited to those in Formula I and in FIGS. 1–5 trigger the release of cytochrome c from mitochondria into the cytosol, resulting in the cleavage and activity of caspase-3 and thereafter, apoptosis. These compounds are thus useful in the treatment of any disorder which is mediated by, or benefited by, regulation of cell growth, differentiation, and/or induction of cell death. In addition, treatment with sphingolipids has been shown to down-regulate Bcl-2 levels, which further sensitizes cancer cells to apoptosis induced by other apoptotic stimuli including chemotherapeutic drugs, γ-radiation and Fas ligand. Therefore, treatment with sphingolipids sensitizes cancer cells simultaneously by promoting the cytosolic accumulation of cytochrome c and by down-regulating Bcl-2, which acts as a barrier to this event.

It has been discovered that compounds of the above formula can be used to treat bacterial infections.

It is still another object of the present invention to provide new sphingolipid compositions for the modification of the colonization of microfora that influence colon cancer and other intestinal disorders.

BRIEF DESCRIPTION OF THE FIGURES

FIGS. 5(a) and 5(b) are illustrations of representative fumonisins.

FIG. 8 illustrates the preparation of protected imidate (22) using literature procedures, which include the treatment of commercially-available D-glucuronolactone (18) with sodium methoxide in methanol, following the acetylation of methyl ester (19) with acetic anhydride, hydrolysis of β-acetoxyglucuronic acid methyl ester (20) with hydrazine acetate, and treatment of the resulting hemiacetal (21) with trichloroacetonitrile. FIG. 9 illustrates the glycosylation and deprotection steps of the synthesis.

DETAILED DESCRIPTION OF THE INVENTION

Figure 1:
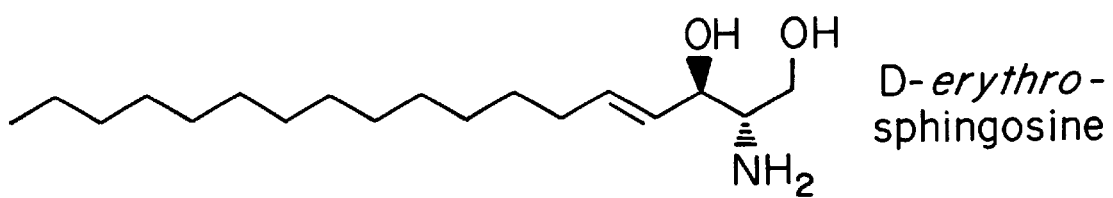
FIG. 1 is an illustration of the stereochemical configuration of sphingosine.

The present invention includes derivatives and analogs of sphingolipids and fumonisins (referred to below as "sphingolipid metabolism altering compounds"), and pharmaceutical compositions and salts thereof, as well as methods to modify cellular metabolism, including by inhibiting abnormal cell proliferation, promoting cell differentiation, including apoptosis, modifying the colonization of microfora that influence colon cancer and other intestinal disorders, inhibiting protein kinase C activity, decreasing inflammatory reactions, psoriasis, inflammatory bowel disease as well as proliferation of smooth muscle cells in the course of development of plaques in vascular tissue that includes administering an effective amount of the sphingolipid metabolism altering compound to a host animal in need thereof, either alone or in combination with another bioactive agent.

I. Active Compounds a) Sphingolipid Derivatives

Derivatives of sphingolipids of the formula:

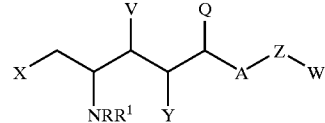

are provided wherein:

A is a spacer group which is $(CH_2)_m$ where m=0–14, where any of the hydrogens may be independently replaced by $R^1$ and X and where any two adjacent carbons may be independently replaced by a $C_3$–$C_8$ cycloalkyl group, a 1,2-, 1,3- or 1,4-disubstituted benzene group, or a 2,3-, 2,4- or 2,5-disubstituted thiophene, furan or pyrrole group;

X, Y, V, and Q are independently hydrogen, $OR^1$, $NR_2$, CN, alkyl, acyl (i.e., C(O)R), carboxylate (i.e., OC(O)R), and wherein alternatively, V and Y, Y and Q or Q and A can together constitute a double or triple bond;

W=no substituent, H, alkyl, aryl, alkenyl, alkynyl, alkaryl, aralkyl, $C(O)(CH_2)_nCO_2H$, $C(O)(CH_2)_nCW'_2CO_2H$, or $OR^1$;

W' is selected independently from H, alkyl, aryl, $(CH_2)_nCO_2H$; $(CH_2)_nCH(CO_2H)CH_2CO_2H$; and $(CH_2)nCH(CO_2H)CH(CH_2CO_2H)CO_2H$;

Z is H, O, NH, NR, NHC(O), C(O)OR, C(O)NH, or C(O)NR;

R is selected independently from H, alkyl, acyl, alkenyl, alkynyl, aryl, alkaryl, aralkyl, or heteroaryl;

$R^1$ is R or $R^2$;

$R^2$ is phosphate (OP(OR_3), wherein at least one R is not hydrogen), b-D-galactoside, N-acetyl-b-D-glucosamine, a-D-mannoside, an organic azo-bond containing moiety that can be reduced by an azoreductase, b-D-cellobiosides, b-D-glucopyranosides, b-D-galactopyranosides, b-D-glucuronides, starch (such as maize starch, amylomaize starch, pectin and others found in wheat flour, potato and beans), lactose, raffinose, stachyose, fructooligosaccharides (such as oligofructose and inulin), an amide or ester of b-cyclodextrin, dextran linked via succinate and glutarate, an amino acid or peptide, or a polyamino acid or polypeptide, furanose and pyranose carbohydrates, sulfonate (and esters thereof), phosphocholine, phosphoserine, and phosphoethanolamine;

wherein there is at least one $R^2$ substituent in the sphingolipid derivative.

In another embodiment, $R^2$ is a biologically active molecule linked to a second "targeting molecule" either directly or through a linking moiety, including, but not limited to A. In a preferred embodiment, the targeting molecule is a moiety that binds to a receptor molecule on the target membrane's surface, as described in more detail below.

b) Fumonisins

In another embodiment, a derivative of a fumonisin is provided that includes at least one covalently bound $R^2$ group. Fumonisins are a family of mycotoxins produced by *Fusarium moniliforme* and related fungi that are common contaminants of maize, sorghum, and related grains. Fumonisins, and their analogs, are known to affect the biosynthetic pathway of sphingolipids. Fumonisins and their analogs are generally referred to collectively as "fumonisin" or "fumonisins" herein. Thus, the present invention provides a method of altering the metabolism of sphingolipids in a cell comprising contacting the cell with a metabolism altering amount of a fumonisin, or an analog thereof, that includes at least one covalently bound $R^2$ group, either directly or through a spacer group. "Fumonisin analog" means any compound which has structural similarity to fumonisin $B_1$, $B_2$, $B_3$, or $B_4$ and can alter the metabolism of sphingolipids. The term "structural similarity to a fumonisin" refers to three basic units as given in FIG. 5: (a) a 1-aminobutan-2-ol head group which may be further substituted by substituents X, Y and V; (b) a spacer group consisting of an alkyl, by hydroxyalkyl or dihydroxyalkyl chain (straight or branched); and (c) a hydrophilic tail (Z-W) in which Z contains an oxygen or nitrogen atom which can be further functionalized to attach mono- or polycarboxylate moieties (W). Fumonisin analogs are disclosed in U.S. Pat. No. 5,232,837, incorporated herein by reference.

The term alkyl, as used herein, unless otherwise specified, refers to a saturated straight, branched, or cyclic, primary, secondary, or tertiary hydrocarbon of $C_1$ to $C_{20}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, halo, cyano, sulfonic acid, sulfate, phosphonic acid, phosphate, or phosphonate, either unprotected, or protected as necessary, as known to those skilled in the art, for example, as taught in Green, et al., "Protective Groups in Organic Synthesis," John Wiley and Sons, Second Edition, 1991.

The term alkaryl or alkylaryl refers to an alkyl group with an aryl substituent.

The term aralkyl or arylalkyl refers to an aryl group with an alkyl substituent.

The term halo, as used herein, includes chloro, bromo, iodo, and fluoro.

The term heteroaryl or heteroaromatic, as used herein, refers to an aromatic moiety that includes at least one sulfur, oxygen, or nitrogen in the aromatic ring. Non-limiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbozolyl, oxazolyl, thiazolyl, isothiazolyl, 1,2,4-thiadiazolyl, isoxazolyl, pyrrolyl, quinazolinyl, pyridazinyl, pyrazinyl, cinnolinyl, phthalazinyl, quinoxalinyl, xanthinyl, hypoxanthinyl, and pteridinyl. Functional oxygen and nitrogen groups on the heterocyclic base can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl.

The term alkenyl, as referred to herein, and unless otherwise specified, refers to a straight, branched, hydrocarbon of $C_2$ to $C_{20}$ with at least one double bond.

The term acyl refers to moiety of the formula —$C(O)R^3$, wherein $R^3$ is alkyl; aryl, alkaryl, aralkyl, heteroaromatic, alkoxyalkyl including methoxymethyl; arylalkyl including benzyl; aryloxyalkyl such as phenoxymethyl; aryl including phenyl optionally substituted with halogen, $C_1$ to $C_4$ alkyl or $C_1$ to $C_4$ alkoxy, or the residue of an amino acid. In one embodiment, the acyl group is the residue of a saturated or unsaturated fatty acid. As used herein the term fatty acid refers to a long chain ($C_6$ to $C_{26}$) aliphatic carboxylic acid, including saturated and unsaturated acids, including $\alpha$-hydroxy fatty acids. Non-limiting examples of fatty acids are lauric, oleic, caproic, linoleic, linolenic, caprylic, capric, perlargonic, neononanoic, neodecanoic, palmitelaidoic, myristic, palmitic, stearic, arachidic, behenic, lignoceric, heptanoic, nonanoic, undecanoic, tridecanoic, pentadecanoic, heptadecanoic, nonadecanoic, heneicosanoic, tricosanoic, arachidonic, docosahexanoic, elaidic, erucic, nervonic, palmitoleic and petriselinic acid.

The term enantiomerically enriched, as used herein, refers to a compound that is a mixture of enantiomers in which one enantiomer is present in excess, and preferably present to the extent of 95% or more, and more preferably 98% or more, including 100%.

The term amino acid includes naturally occurring and synthetic amino acids, and includes but it not limited to, alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, and histidinyl.

As used herein, the term pharmaceutically acceptable salts refers to salts that retain the desired biological activity of the herein-identified compounds and exhibit minimal undesired toxicological effects. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylene-diamine, D-glucosamine, tetraethylammonium, or ethylenediamine; or (c) combinations of (a) and (b); e.g., a zinc tannate salt or the like.

The active compounds are administered in an effective amount to alter sphingolipid metabolism, and thus are useful in the treatment of abnormal cell proliferation, including tumors, cancer, psoriasis, and familial polyposis; in the promotion of cell differentiation, in the induction of apoptosis, in the treatment of infections caused by microorganisms which have sphingolipid receptors which allow colonization of the microorganism; in the modification of microfora that influence colon cancer and other intestinal disorders; in the inhibition of protein kinase C activity, and in the treatment of inflammatory conditions including psoriasis, inflammatory bowel disease as well as proliferation of smooth muscle cells in the course of development of plaques in vascular tissue. These compounds either exhibit activity in themselves or act as a prodrug of a parent compound. The compounds can be administered alone or in combination with other biologically active compounds to achieve the desired effect.

In one preferred embodiment, A is $C_{13}H_{26}$; Z=H; W=no substituent; X=O-β-glucoronide; $R^1$=octanoyl; R=H; V=OH; Y and Q constitute a double bond.

In another embodiment, A=$C_{13}H_{26}$; A=H; W=no substituent; X=O-β-glucoronide; $R^1$=octanoyl; R=H; V=OH; Y and Q constitute a triple bond.

In yet another embodiment, A=$C_{13}H_{26}$; A=H; W=no substituent; X=OH; $R^1$=octanoyl; R=H; V=OH; Y and Q constitute a triple bond.

In still another embodiment, A=$C_{13}H_{26}$; Z=H; W=no substituent; X=OH; $R^1$=octanoyl; R=H; V=O-β-glucoronide; Y and Q constitute a triple bond.

In yet another preferred embodiment, A=$C_{13}H_{26}$; Z=H; W=no substituent; X=OH; $R^1$=octanoyl; R=H; V=OH; Y=O-β-glucoronide; and Q=H.

In another embodiment, A=$C_{13}H_{26}$; Z=H; W=no substituent; X=OH; $R^1$=octanoyl; R=H; V=OH; Y=H and Q=O-β-glucoronide.

In yet another embodiment, A=$C_{13}H_{26}$; Z=H; W=no substituent; X=O-β-glucoronide; $R^1$=octanoyl; R=H; V=OH; Y=H; and Q=H.

In still another embodiment, A=$C_{13}H_{26}$; Z=H; W=no substituent; X=OH; $R^1$=octanoyl; R=H; V=O-β-glucoronide; Y=H; Q=H.

In another embodiment, A=$C_{13}H_{26}$; Z=H; W=no substituent; X=H; $R^1$=octanoyl; R=H; V=O-β-glucoronide; Y and Q constitute a double bond.

In another embodiment, A=$C_{13}H_{26}$; Z=H; W=no substituent; X=H; $R^1$=octanoyl; R=H; V=O-β-glucoronide; Y and Q constitute a triple bond.

In another embodiment, A=$C_{13}H_{26}$; Z=H; W=no substituent; X=H; $R^1$=octanoyl; R=H; V=OH; Y=O-βglucoronide; and Q=H.

In another embodiment, A=$C_{13}H_{26}$; Z=H; W=no substituent; X=H; $R^1$=octanoyl; R=H; V=OH; Y=H; Q=O-β-glucoronide.

In another embodiment, A=$C_{13}H_{26}$; Z=H; W=no substituent; X=H; $R^1$=octanoyl; R=H; V=O-β-glucoronide; Y=H; and Q=H.

In another embodiment, A=$C_{13}H_{26}$; Z=H; W=no substituent; X=O-oligofructoside; $R^1$=octanoyl; R=H; V=OH; Y and Q constitute a double bond.

In another embodiment, A=$C_{13}H_{26}$; Z=H; W=no substituent; X=O-oligofructoside; $R^1$=octanoyl; R=H; V=OH; Y and Q constitute a triple bond.

In another embodiment, A=$C_{13}H_{26}$; Z=H; W=no substituent; X=OH; $R^1$=octanoyl; R=H; V=O-oligofructoside; Y and Q constitute a double bond.

In another embodiment, A=$C_{13}H_{26}$; Z=H; W=no substituent; X=OH; $R^1$=octanoyl; R=H; V=O-oligofructoside; Y and Q constitute a triple bond.

In another embodiment, A=$C_{13}H_{26}$; Z=H; W=no substituent; X=OH; $R^1$=octanoyl; R=H; V=OH; Y-O-oligofructoside; and Q=H.

In another embodiment, A=$C_{13}H_{26}$; Z=H; W=no substituent; X=OH; $R^1$=octanoyl; R=H; V=OH; Y=H; and Q=O-oligofructoside.

In another embodiment, A=$C_{13}H_{26}$; Z=H; W=no substituent; X=O-oligofructoside; $R^1$=octanoyl; R=H; V=OH; Y=H; and Q=H.

In another embodiment, A=$C_{13}H_{26}$; Z=H; W=no substituent; X=OH; $R^1$=octanoyl; R=H; V=O-oligofructoside; Y=H; and Q=H.

In another embodiment, A=$C_{13}H_{26}$; Z=H; W=no substituent; X=H; $R^1$=octanoyl; R=H; V=O-oligofructoside; Y and Q constitute a double bond.

In another embodiment, A=$C_{13}H_{26}$; Z=H; W=no substituent; X=H; $R^1$=octanoyl; R=H; V=O-oligofructoside; Y and Q constitute a triple bond.

In another embodiment, A=$C_{13}H_{26}$; Z=H; W=no substituent; X=H; $R^1$=octanoyl; R=H; V=OH; Y=O-oligofructoside; and Q=H.

In another embodiment, A=$C_{13}H_{26}$; Z=H; W=no substituent; X=H; $R^1$=octanoyl; R=H; V=OH; Y=H; and Q=O-oligofructoside.

In another embodiment, A=$C_{13}H_{26}$; Z=H; W=no substituent; X=H; $R^1$=octanoyl; R=H; V=O-oligofructoside; Y=H; and Q=H.

In another embodiment, A=$C_{13}H_{26}$; Z=H; W=no substituent; X=O-fructoside; $R^1$=octanoyl; R=H; V=OH; Y and Q constitute a double bond.

In another embodiment, A=$C_{13}H_{26}$; Z=H; W=no substituent; X=O-fructoside; $R^1$=octanoyl; R=H; V=OH; Y and Q constitute a triple bond.

In another embodiment, A=$C_{13}H_{26}$; Z=H; W=no substituent; X=OH; $R^1$=octanoyl; R=H; V=O-fructoside; Y and Q constitute a double bond.

In another embodiment, A=$C_{13}H_{26}$; Z=H; W=no substituent; X=OH; $R^1$=octanoyl; R=H; V=O-fructoside; Y and Q constitute a triple bond.

In another embodiment, A=$C_{13}H_{26}$; Z=H; W=no substituent; X=OH; $R^1$=octanoyl; R=H; V=OH; Y=O-fructoside; and Q=H.

In another embodiment, A=$C_{13}H_{26}$; Z=H; W=no substituent; X=OH; $R^1$=octanoyl; R=H; V=OH; Y=H; Q=O-fructoside.

In another embodiment, A=$C_{13}H_{26}$; Z=H; W=no substituent; X=O-fructoside; $R^1$=octanoyl; R=H; V=OH; Y=H; and Q=H.

In another embodiment, A=$C_{13}H_{26}$; Z=H; W=no substituent; X=OH; $R^1$=octanoyl; R=H; V=O-fructoside; Y=H; and Q=H.

In another embodiment, A=$C_{13}H_{26}$; Z=H; W=no substituent; X=H; $R^1$=octanoyl; R=H; V=O-fructoside; Y and Q constitute a double bond.

In another embodiment, A=$C_{13}H_{26}$; Z=H; W=no substituent; X=H; $R^1$=octanoyl; R=H; V=O-fructoside; Y and Q constitute a triple bond.

In another embodiment, A=$C_{13}H_{26}$; Z=H; W=no substituent; X=H; $R^1$=octanoyl; R=H; V=OH; Y=O-fructoside; and Q=H.

In another embodiment, A=$C_{13}H_{26}$; Z=H; W=no substituent; X=H; $R^1$=octanoyl; R=H; V=OH; Y=H; Q=O-fructoside.

In another embodiment, A=$C_{13}H_{26}$; Z=H; W=no substituent; X=H; $R^1$=octanoyl; R=H; V=O-fructoside; Y=H; and Q=H.

In another embodiment, A=$C_{13}H_{26}$; Z=H; W=no substituent; X=O-mannoside; $R^1$=octanoyl; R=H; V=OH; Y and Q constitute a double bond.

In another embodiment, A=$C_{13}H_{26}$; Z=H; W=no substituent; X=O-mannoside; $R^1$=octanoyl; R=H; V=OH; Y and Q constitute a triple bond.

In another embodiment, A=$C_{13}H_{26}$; Z=H; W=no substituent; X=OH; $R^1$=octanoyl; R=H; V=O-mannoside; Y and Q constitute a double bond.

In another embodiment, A=$C_{13}H_{26}$; Z=H; W=no substituent; X=OH; $R^1$=octanoyl; R=H; V=O-mannoside; Y and Q constitute a triple bond.

In another embodiment, A=$C_{13}H_{26}$; Z=H; W=no substituent; X=OH; $R^1$=octanoyl; R=H; V=OH; Y=O-mannoside; and Q=H.

In another embodiment, A=$C_{13}H_{26}$; Z=H; W=no substituent; X=OH; $R^1$=octanoyl; R=H; V=OH; Y=H; and Q=O-mannoside.

In another embodiment, A=$C_{13}H_{26}$; Z=H; W=no substituent; X=O-mannoside; $R^1$=octanoyl; R=H; V=OH; Y=H; and Q=H.

In another embodiment, A=$C_{13}H_{26}$; Z=H; W=no substituent; X=OH; $R^1$=octanoyl; R=H; V=O-mannoside; Y=H; and Q=H.

In another embodiment, A=$C_{13}H_{26}$; Z=H; W=no substituent; X=H; $R^1$=octanoyl; R=H; V=O-mannoside; Y and Q constitute a double bond.

In another embodiment, A=$C_{13}H_{26}$; Z=H; W=no substituent; X=H; $R^1$=octanoyl; R=H; V=O-mannoside; Y and Q constitute a triple bond.

In another embodiment, A=$C_{13}H_{26}$; Z=H; W=no substituent; X=H; $R^1$=octanoyl; R=H; V=OH; Y=O-mannoside; and Q=H.

In another embodiment, A=$C_{13}H_{26}$; Z=H; W=no substituent; X=H; $R^1$=octanoyl; R=H; V=OH; Y=H; and Q=O-mannoside.

In another embodiment, A=$C_{13}H_{26}$; Z=H; W=no substituent; X=H; $R^1$=octanoyl; R=H; V=O-mannoside; Y=H; and Q=H.

In another embodiment, A=$C_{13}H_{26}$; Z=H; W=no substituent; X=O-cellobioside; $R^1$=octanoyl; R=H; V=OH; Y and Q constitute a double bond.

In another embodiment, A=$C_{13}H_{26}$; Z=H; W=no substituent; X=O-cellobioside; $R^1$=octanoyl; R=H; V=OH; Y and Q constitute a triple bond.

In another embodiment, A=$C_{13}H_{26}$; Z=H; W=no substituent; X=OH; $R^1$=octanoyl; R=H; V=O-cellobioside; Y and Q constitute a double bond.

In another embodiment, A=$C_{13}H_{26}$; Z=H; W=no substituent; X=OH; $R^1$=octanoyl; R=H; V=O-cellobioside; Y and Q constitute a triple bond.

In another embodiment, A=$C_{13}H_{26}$; Z=H; W=no substituent; X=OH; $R^1$=octanoyl; R=H; V=OH; Y=O-cellobioside; and Q=H.

In another embodiment, A=$C_{13}H_{26}$; Z=H; W=no substituent; X=OH; $R^1$=octanoyl; R=H; V=OH; Y=H; and Q=O-cellobioside.

In another embodiment, A=$C_{13}H_{26}$; Z=H; W=no substituent; X=O-cellobioside; $R^1$=octanoyl; R=H; V=OH; Y=H; and Q=H.

In another embodiment, A=$C_{13}H_{26}$; Z=H; W=no substituent; X=OH; $R^1$=octanoyl; R=H; V=O-cellobioside; Y=H; and Q=H.

In another embodiment, A=$C_{13}H_{26}$; Z=H; W=no substituent; X=H; $R^1$=octanoyl; R=H; V=O-cellobioside; Y and Q constitute a double bond.

In another embodiment, A=$C_{13}H_{26}$; Z=H; W=no substituent; X=H; $R^1$=octanoyl; R=H; V=O-cellobioside; Y and Q constitute a triple bond.

In another embodiment, A=$C_{13}H_{26}$; Z=H; W=no substituent; X=H; $R^1$=octanoyl; R=H; V=OH; Y=O-cellobioside; and Q=H.

In another embodiment, A=$C_{13}H_{26}$; Z=H; W=no substituent; X=H; $R^1$=octanoyl; R=H; V=OH; Y=H; and Q=O-cellobioside.

In another embodiment, A=$C_{13}H_{26}$; Z=H; W=no substituent; X=H; $R^1$=octanoyl; R=H; V=O-cellobioside; Y=H and Q=H.

In another embodiment, A=$C_{14}H_{28}$; Z=O; W=C(O)CH$(CH_2COOH)_2$; X=O-β-glucoronide; $R^1$=octanoyl; R=H; V=OH; Y and Q constitute a double bond.

In another embodiment, A=$C_{14}H_{28}$; Z=O; W=C(O)CH$(CH_2COOH)_2$; X=O-β-glucoronide; $R^1$=octanoyl; R=H; V=OH; Y and Q constitute a triple bond.

In another embodiment, A=$C_{14}H_{28}$; Z=O; W=C(O)CH$(CH_2COOH)_2$; X=OH; $R^1$=octanoyl; R=H; V=O-β-glucoronide; Y and Q constitute a double bond.

In another embodiment, A=$C_{14}H_{28}$; Z=O; W=C(O)CH$(CH_2COOH)_2$; X=OH; $R^1$=octanoyl; R=H; V=O-β-glucoronide; Y and Q constitute a triple bond.

In another embodiment, A=$C_{14}H_{28}$; Z=O; W=C(O)CH$(CH_2COOH)_2$; X=OH; $R^1$=octanoyl; R=H; V=OH; Y=O-β-glucoronide; and Q=H.

In another embodiment, A=$C_{14}H_{28}$; Z=O; W=C(O)CH$(CH_2COOH)_2$; X=OH; $R^1$=octanoyl; R=H; V=OH; Y=H; and Q=O-βglucoronide.

In another embodiment, A=$C_{14}H_{28}$; Z=O; W=C(O)CH$(CH_2COOH)_2$; X=O-βglucoronide; $R^1$=octanoyl; R=H; V=OH; Y=H; and Q=H.

In another embodiment, A=$C_{14}H_{28}$; Z=O; W=C(O)CH$(CH_2COOH)_2$; X=OH; $R^1$=octanoyl; R=H; V=O-β-glucoronide; Y=H; and Q=H.

In another embodiment, A=$C_{14}H_{28}$; Z=O; W=C(O)CH$(CH_2COOH)_2$; X=H; $R^1$=octanoyl; R=H; V=O-βglucoronide; Y and Q constitute a double bond.

In another embodiment, A=$C_{14}H_{28}$; Z=O; W=C(O)CH$(CH_2COOH)_2$; X=H; $R^1$=octanoyl; R=H; V=O-β-glucoronide; Y and Q constitute a triple bond.

In another embodiment, A=$C_{14}H_{28}$; Z=O; W=C(O)CH$(CH_2COOH)_2$; X=H; $R^1$=octanoyl; R=H; V=OH; Y=O-β-glucoronide; and Q=H.

In another embodiment, A=$C_{14}H_{28}$; Z=O; W=C(O)CH$(CH_2COOH)_2$; X=H; $R^1$=octanoyl; R=H; V=OH; Y=H; and Q=O-β-glucoronide.

In another embodiment, A=$C_{14}H_{28}$; Z=O; W=C(O)CH$(CH_2COOH)_2$; X=H; $R^1$=octanoyl; R=H; V=O-β-glucoronide; Y=H; and Q=H.

In another embodiment, A=$C_{14}H_{28}$; Z=O; W=C(O)CH$(CH_2COOH)_2$; X=O-fructoside; $R^1$=octanoyl; R=H; V=OH; Y and Q constitute a double bond.

In another embodiment, A=$C_{14}H_{28}$; Z=O; W=C(O)CH$(CH_2COOH)_2$; X=O-fructoside; $R^1$=octanoyl; R=H; V=OH; Y and Q constitute a triple bond.

In another embodiment, A=$C_{14}H_{28}$; Z=O; W=C(O)CH$(CH_2COOH)_2$; X=OH;; $R^1$=octanoyl; R=H; V=O-fructoside; Y and Q constitute a double bond.

In another embodiment, A=$C_{14}H_{28}$; Z=O; W=C(O)CH$(CH_2COOH)_2$; X=OH; $R^1$=octanoyl; R=H; V=O-fructoside; Y and Q constitute a double bond.

In another embodiment, A=$C_{14}H_{28}$; Z=O; W=C(O)CH$(CH_2COOH)_2$; X=OH; $R^1$=octanoyl; R=H; V=OH; Y=fructoside; and Q=H.

In another embodiment, $A=C_{14}H_{28}$; $Z=O$; $W=C(O)CH(CH_2COOH)_2$; $X=OH$; $R^1$=octanoyl; $R=H$; $V=OH$; $Y=H$; and Q=fructoside.

In another embodiment, $A=C_{14}H_{28}$; $Z=O$; $W=C(O)CH(CH_2COOH)_2$; X=O-fructoside; $R^1$=octanoyl; $R=H$; $V=OH$; $Y=H$; and Q=H.

In another embodiment, $A=C_{14}H_{28}$; $Z=O$; $W=C(O)CH(CH_2COOH)_2$; $X=OH$; $R^1$=octanoyl; $R=H$; V=O-fructoside; $Y=H$; and Q=H.

In another embodiment, $A=C_{14}H_{28}$; $Z=O$; $W=C(O)CH(CH_2COOH)_2$; X=H;; $R^1$=octanoyl; $R=H$; V=O-fructoside; Y and Q constitute a double bond.

In another embodiment, $A=C_{14}H_{28}$; $Z=O$; $W=C(O)CH(CH_2COOH)_2$; X=H; $R^1$=octanoyl; $R=H$; V=O-fructoside; Y and Q constitute a triple bond.

In another embodiment, $A=C_{14}H_{28}$; $Z=O$; $W=C(O)CH(CH_2COOH)_2$; X=H; $R^1$=octanoyl; $R=H$; $V=OH$; Y=O-fructoside; and Q=H.

In another embodiment, $A=C_{14}H_{28}$; $Z=O$; $W=C(O)CH(CH_2COOH)_2$; X=H; $R^1$=octanoyl; $R=H$; $V=OH$; $Y=H$; and Q=O-fructoside.

In another embodiment, $A=C_{14}H_{28}$; $Z=O$; $W=C(O)CH(CH_2COOH)_2$; X=H; $R^1$=octanoyl; $R=H$; V=O-fructoside; $Y=H$ and Q=H.

In another embodiment, $A=C_{14}H_{28}$; $Z=O$; $W=C(O)CH(CH_2COOH)_2$; X=O-mannoside; $R^1$=octanoyl; $R=H$; $V=OH$; Y and Q constitute a double bond.

In another embodiment, $A=C_{14}H_{28}$; $Z=O$; $W=C(O)CH(CH_2COOH)_2$; X=O-mannoside; $R^1$=octanoyl; $R=H$; $V=OH$; Y and Q constitute a triple bond.

In another embodiment, $A=C_{14}H_{28}$; $Z=O$; $W=C(O)CH(CH_2COOH)_2$; $X=OH$; $R^1$=octanoyl; $R=H$; $V=OH$; $Y=H$; Q=O-mannoside.

In another embodiment, $A=C_{14}H_{28}$; $Z=O$; $W=C(O)CH(CH_2COOH)_2$; X=O-mannoside; $R^1$=octanoyl; $R=H$; $V=OH$; $Y=H$; and Q=H.

In another embodiment, $A=C_{14}H_{28}$; $Z=O$; $W=C(O)CH(CH_2COOH)_2$; $X=OH$; $R^1$=octanoyl; $R=H$; V=O-mannoside; $Y=H$; and Q=H.

In another embodiment, $A=C_{14}H_{28}$; $Z=O$; $W=C(O)CH(CH_2COOH)_2$; X=H; $R^1$=octanoyl; $R=H$; V=O-mannoside; Y and Q constitute a double bond.

In another embodiment, $A=C_{14}H_{28}$; $Z=O$; $W=C(O)CH(CH_2COOH)_2$; X=H; $R^1$=octanoyl; $R=H$; V=O-mannoside; Y and Q constitute a triple bond.

In another embodiment, $A=C_{14}H_{28}$; $Z=O$; $W=C(O)CH(CH_2COOH)_2$; X=H; $R^1$=octanoyl; $R=H$; $V=OH$; Y=O-mannoside; Q=H.

In another embodiment, $A=C_{14}H_{28}$; $Z=O$; $W=C(O)CH(CH_2COOH)_2$; X=H; $R^1$=octanoyl; $R=H$; $V=OH$; $Y=H$; Q=O-mannoside.

In another embodiment, $A=C_{14}H_{28}$; $Z=O$; $W=C(O)CH(CH_2COOH)_2$; X=H; $R^1$=octanoyl; $R=H$; V=O-mannoside; $Y=H$; and Q=H.

In another embodiment, $A=C_{14}H_{28}$; $Z=O$; $W=C(O)CH(CH_2COOH)_2$; X=O-cellobioside; $R^1$=octanoyl; $R=H$; $V=OH$; Y and Q constitute a double bond.

In another embodiment, $A=C_{14}H_{28}$; $Z=O$; $W=C(O)CH(CH_2COOH)_2$; X=O-cellobioside; $R^1$=octanoyl; $R=H$; $V=OH$; Y and Q constitute a triple bond.

In another embodiment, $A=C_{14}H_{28}$; $Z=O$; $W=C(O)CH(CH_2COOH)_2$; $X=OH$; $R^1$=octanoyl; $R=H$; V=O-cellobioside; Y and Q constitute a double bond.

In another embodiment, $A=C_{14}H_{28}$; $Z=O$; $W=C(O)CH(CH_2COOH)_2$; $X=OH$; $R^1$=octanoyl; $R=H$; V=O-cellobioside; Y and Q constitute a triple bond.

In another embodiment, $A=C_{14}H_{28}$; $Z=O$; $W=C(O)CH(CH_2COOH)_2$; $X=OH$; $R^1$=octanoyl; $R=H$; $V=OH$; Y=O-cellobioside; Q=H.

In another embodiment, $A=C_{14}H_{28}$; $Z=O$; $W=C(O)CH(CH_2COOH)_2$; $X=OH$; $R^1$=octanoyl; $R=H$; $V=OH$; $Y=H$; Q=O-cellobioside.

In another embodiment, $A=C_{14}H_{28}$; $Z=O$; $W=C(O)CH(CH_2COOH)_2$; X=O-cellobioside; $R^1$=octanoyl; $R=H$; $V=OH$; $Y=H$; and Q=H.

In another embodiment, $A=C_{14}H_{28}$; $Z=O$; $W=C(O)CH(CH_2COOH)_2$; $X=OH$; $R^1$=octanoyl; $R=H$; V=O-cellobioside; $Y=H$; and Q=H.

In another embodiment, $A=C_{14}H_{28}$; $Z=O$; $W=C(O)CH(CH_2COOH)_2$; X=H; $R^1$=octanoyl; $R=H$; V=O-cellobioside; Y and Q constitute a double bond.

In another embodiment, $A=C_{14}H_{28}$; $Z=O$; $W=C(O)CH(CH_2COOH)_2$; X=H; $R^1$=octanoyl; $R=H$; V=O-cellobioside; Y and Q constitute a triple bond.

In another embodiment, $A=C_{14}H_{28}$; $Z=O$; $W=C(O)CH(CH_2COOH)_2$; X=H; $R^1$=octanoyl; $R=H$; $V=OH$; Y=O-cellobioside; Q=H.

In another embodiment, $A=C_{14}H_{28}$; $Z=O$; $W=C(O)CH(CH_2COOH)_2$; X=H; $R^1$=octanoyl; $R=H$; $V=OH$; $Y=H$; Q=O-cellobioside.

In another embodiment, $A=C_{14}H_{28}$; $Z=O$; $W=C(O)CH(CH_2COOH)_2$; X=H; $R^1$=octanoyl; $R=H$; V=O-cellobioside; $Y=H$; and Q=H.

In another embodiment, $A=C_{14}H_{28}$; Z=NH; $W=C(O)CH(CH_2COOH)_2$; X=O-β-glucoronide; $R^1$=octanoyl; $R=H$; $V=OH$; Y and Q constitute a double bond.

In another embodiment, $A=C_{14}H_{28}$; Z=NH; $W=C(O)CH(CH_2COOH)_2$; X=O-β-glucoronide; $R^1$=octanoyl; $R=H$; $V=OH$; Y and Q constitute a triple bond.

In another embodiment, $A=C_{14}H_{28}$; Z=NH; $W=C(O)CH(CH_2COOH)_2$; $X=OH$; $R^1$=octanoyl; $R=H$; V=O-β-glucoronide; Y and Q constitute a double bond.

In another embodiment, $A=C_{14}H_{28}$; Z=NH; $W=C(O)CH(CH_2COOH)_2$; $X=OH$; $R^1$=octanoyl; $R=H$; V=O-β-glucoronide; Y and Q constitute a triple bond.

In another embodiment, $A=C_{14}H_{28}$; Z=NH; $W=C(O)CH(CH_2COOH)_2$; $X=OH$; $R^1$=octanoyl; $R=H$; $V=OH$; Y=O-β-glucoronide; Q=H.

In another embodiment, $A=C_{14}H_{28}$; Z=NH; $W=C(O)CH(CH_2COOH)_2$; $X=OH$; $R^1$ octanoyl; $R=H$; $V=OH$; $Y=H$; Q=O-β-glucoronide.

In another embodiment, $A=C_{14}H_{28}$; Z=NH; $W=C(O)CH(CH_2COOH)_2$; X=O-β-glucoronide; $R^1$=octanoyl; $R=H$; $V=OH$; $Y=H$; and Q=H.

In another embodiment, $A=C_{14}H_{28}$; Z=NH; $W=C(O)CH(CH_2COOH)_2$; $X=OH$; $R^1$=octanoyl; $R=H$; V=O-β-glucoronide; $Y=H$; and Q=H.

In another embodiment, $A=C_{14}H_{28}$; Z=NH; $W=C(O)CH(CH_2COOH)_2$; X=H; $R^1$=octanoyl; $R=H$; V=O-β-glucoronide; Y and Q constitute a double bond.

In another embodiment, $A=C_{14}H_{28}$; Z=NH; $W=C(O)CH(CH_2COOH)_2$; X=H; $R^1$=octanoyl; $R=H$; V=O-β-glucoronide; Y and Q constitute a triple bond.

In another embodiment, $A=C_{14}H_{28}$; Z=NH; $W=C(O)CH(CH_2COOH)_2$; X=H; $R^1$=octanoyl; $R=H$; $V=OH$; Y=O-β-glucoronide; Q=H.

In another embodiment, $A=C_{14}H_{28}$; Z=NH; $W=C(O)CH(CH_2COOH)_2$; X=H; $R^1$=octanoyl; $R=H$; $V=OH$; $Y=H$; Q=O-β-glucoronide.

In another embodiment, $A=C_{14}H_{28}$; Z=NH; $W=C(O)CH(CH_2COOH)_2$; X=H; $R^1$=octanoyl; $R=H$; V=O-β-glucoronide; $Y=H$; and Q=H.

In another embodiment, $A=C_{14}H_{28}$; Z=NH; $W=C(O)CH(CH_2COOH)_2$; X=O-oligofructoside; $R^1$=octanoyl; $R=H$; $V=OH$; Y and Q constitute a double bond.

In another embodiment, $A=C_{14}H_{28}$; Z=NH; $W=C(O)CH(CH_2COOH)_2$; X=O-oligofructoside; $R^1$=octanoyl; $R=H$; $V=OH$; Y and Q constitute a triple bond.

In another embodiment, $A=C_{14}H_{28}$; $Z=NH$; $W=C(O)CH(CH_2COOH)_2$; $X=OH$; $R^1$=octanoyl; $R=H$; $V=O$-oligofructoside; Y and Q constitute a double bond.

In another embodiment, $A=C_{14}H_{28}$; $Z=NH$; $W=C(O)CH(CH_2COOH)_2$; $X=OH$; $R^1$=octanoyl; $R=H$; $V=O$-oligofructoside; Y and Q constitute a triple bond.

In another embodiment, $A=C_{14}H_{28}$; $Z=NH$; $W=C(O)CH(CH_2COOH)_2$; $X=OH$; $R^1$=octanoyl; $R=H$; $V=OH$; $Y=O$-oligofructoside; $Q=H$.

In another embodiment, $A=C_{14}H_{28}$; $Z=NH$; $W=C(O)CH(CH_2COOH)_2$; $X=OH$; $R^1$=octanoyl; $R=H$; $V=OH$; $Y=H$; $Q=O$-oligofructoside.

In another embodiment, $A=C_{14}H_{28}$; $Z=NH$; $W=C(O)CH(CH_2COOH)_2$; $X=O$-oligofructoside; $R^1$=octanoyl; $R=H$; $V=OH$; $Y=H$; and $Q=H$.

In another embodiment, $A=C_{14}H_{28}$; $Z=NH$; $W=C(O)CH(CH_2COOH)_2$; $X=OH$; $R^1$=octanoyl; $R=H$; $V=O$-oligofructoside; $Y=H$; and $Q=H$.

In another embodiment, $A=C_{14}H_{28}$; $Z=NH$; $W=C(O)CH(CH_2COOH)_2$; $X=H$; $R^1$=octanoyl; $R=H$; $V=O$-oligofructoside; Y and Q constitute a double bond.

In another embodiment, $A=C_{14}H_{28}$; $Z=NH$; $W=C(O)CH(CH_2COOH)_2$; $X=H$; $R^1$=octanoyl; $R=H$; $V=O$-oligofructoside; Y and Q constitute a triple bond.

In another embodiment, $A=C_{14}H_{28}$; $Z=NH$; $W=C(O)CH(CH_2COOH)_2$; $X=H$; $R^1$=octanoyl; $R=H$; $V=OH$; $Y=O$-oligofructoside; $Q=H$.

In another embodiment, $A=C_{14}H_{28}$; $Z=NH$; $W=C(O)CH(CH_2COOH)_2$; $X=H$; $R^1$=octanoyl; $R=H$; $V=OH$; $Y=H$; $Q=O$-oligofructoside.

In another embodiment, $A=C_{14}H_{28}$; $Z=NH$; $W=C(O)CH(CH_2COOH)_2$; $X=H$; $R^1$=octanoyl; $R=H$; $V=O$-oligofructoside; $Y=H$; and $Q=H$.

In another embodiment, $A=C_{14}H_{28}$; $Z=NH$; $W=C(O)CH(CH_2COOH)_2$; $X=O$-fructoside; $R^1$=octanoyl; $R=H$; $V=OH$; Y and Q constitute a double bond.

In another embodiment, $A=C_{14}H_{28}$; $Z=NH$; $W=C(O)CH(CH_2COOH)_2$; $X=O$-fructoside; $R^1$=octanoyl; $R=H$; $V=OH$; Y and Q constitute a triple bond.

In another embodiment, $A=C_{14}H_{28}$; $Z=NH$; $W=C(O)CH(CH_2COOH)_2$; $X=OH$; $R^1$=octanoyl; $R=H$; $V=O$-fructoside; Y and Q constitute a double bond.

In another embodiment, $A=C_{14}H_{28}$; $Z=NH$; $W=C(O)CH(CH_2COOH)_2$; $X=OH$; $R^1$=octanoyl; $R=H$; $V=O$-fructoside; Y and Q constitute a triple bond.

In another embodiment, $A=C_{14}H_{28}$; $Z=NH$; $W=C(O)CH(CH_2COOH)_2$; $X=OH$; $R^1$=octanoyl; $R=H$; $V=OH$; $Y=O$-fructoside; $Q=H$.

In another embodiment, $A=C_{14}H_{28}$; $Z=NH$; $W=C(O)CH(CH_2COOH)_2$; $X=OH$; $R^1$=octanoyl; $R=H$; $V=OH$; $Y=H$; $Q=O$-fructoside.

In another embodiment, $A=C_{14}H_{28}$; $Z=NH$; $W=C(O)CH(CH_2COOH)_2$; $X=O$-fructoside; $R^1$=octanoyl; $R=H$; $V=OH$; $Y=H$; and $Q=H$.

In another embodiment, $A=C_{14}H_{28}$; $Z=NH$; $W=C(O)CH(CH_2COOH)_2$; $X=OH$; $R^1$=octanoyl; $R=H$; $V=O$-fructoside; $Y=H$; and $Q=H$.

In another embodiment, $A=C_{14}H_{28}$; $Z=NH$; $W=C(O)CH(CH_2COOH)_2$; $X=H$; $R^1$=octanoyl; $R=H$; $V=O$-fructoside; Y and Q constitute a double bond.

In another embodiment, $A=C_{14}H_{28}$; $Z=NH$; $W=C(O)CH(CH_2COOH)_2$; $X=H$; $R^1$=octanoyl; $R=H$; $V=O$-fructoside; Y and Q constitute a triple bond.

In another embodiment, $A=C_{14}H_{28}$; $Z=NH$; $W=C(O)CH(CH_2COOH)_2$; $X=H$; $R^1$=octanoyl; $R=H$; $V=OH$; $Y=O$-fructoside; $Q=H$.

In another embodiment, $A=C_{14}H_{28}$; $Z=NH$; $W=C(O)CH(CH_2COOH)_2$; $X=H$; $R^1$=octanoyl; $R=H$; $V=OH$; $Y=H$; $Q=O$-fructoside.

In another embodiment, $A=C_{14}H_{28}$; $Z=NH$; $W=C(O)CH(CH_2COOH)_2$; $X=H$; $R^1$=octanoyl; $R=H$; $V=O$-fructoside; $Y=H$; and $Q=H$.

In another embodiment, $A=C_{14}H_{28}$; $Z=NH$; $W=C(O)CH(CH_2COOH)_2$; $X=O$-mannoside; $R^1$=octanoyl; $R=H$; $V=OH$; Y and Q constitute a double bond.

In another embodiment, $A=C_{14}H_{28}$; $Z=NH$; $W=C(O)CH(CH_2COOH)_2$; $X=O$-mannoside; $R^1$=octanoyl; $R=H$; $V=OH$; Y and Q constitute a triple bond.

In another embodiment, $A=C_{14}H_{28}$; $Z=NH$; $W=C(O)CH(CH_2COOH)_2$; $X=OH$; $R^1$=octanoyl; $R=H$; $V=O$-mannoside; Y and Q constitute a double bond.

In another embodiment, $A=C_{14}H_{28}$; $Z=NH$; $W=C(O)CH(CH_2COOH)_2$; $X=OH$; $R^1$=octanoyl; $R=H$; $V=O$-mannoside; Y and Q constitute a triple bond.

In another embodiment, $A=C_{14}H_{28}$; $Z=NH$; $W=C(O)CH(CH_2COOH)_2$; $X=OH$; $R^1$=octanoyl; $R=H$; $V=OH$; $Y=O$-mannoside; $Q=H$.

In another embodiment, $A=C_{14}H_{28}$; $Z=NH$; $W=C(O)CH(CH_2COOH)_2$; $X=OH$; $R^1$=octanoyl; $R=H$; $V=OH$; $Y=H$; $Q=O$-mannoside.

In another embodiment, $A=C_{14}H_{28}$; $Z=NH$; $W=C(O)CH(CH_2COOH)_2$; $X=O$-mannoside; $R^1$=octanoyl; $R=H$; $V=OH$; $Y=H$; and $Q=H$.

In another embodiment, $A=C_{14}H_{28}$; $Z=NH$; $W=C(O)CH(CH_2COOH)_2$; $X=OH$; $R^1$=octanoyl; $R=H$; $V=O$-mannoside; $Y=H$; and $Q=H$.

In another embodiment, $A=C_{14}H_{28}$; $Z=NH$; $W=C(O)CH(CH_2COOH)_2$; $X=H$; $R^1$=octanoyl; $R=H$; $V=O$-mannoside; Y and Q constitute double bond.

In another embodiment, $A=C_{14}H_{28}$; $Z=NH$; $W=C(O)CH(CH_2COOH)_2$; $X=H$; $R^1$=octanoyl; $R=H$; $V=O$-mannoside; Y and Q constitute a triple bond.

In another embodiment, $A=C_{14}H_{28}$; $Z=NH$; $W=C(O)CH(CH_2COOH)_2$; $X=H$; $R^1$=octanoyl; $R=H$; $V=OH$; $Y=O$-mannoside; $Q=H$.

In another embodiment, $A=C_{14}H_{28}$; $Z=NH$; $W=C(O)CH(CH_2COOH)_2$; $X=H$; $R^1$=octanoyl; $R=H$; $V=OH$; $Y=H$; $Q=O$-mannoside.

In another embodiment, $A=C_{14}H_{28}$; $Z=NH$; $W=C(O)CH(CH_2COOH)_2$; $X=H$; $R^1$=octanoyl; $R=H$; $V=O$-mannoside; $Y=H$; and $Q=H$.

In another embodiment, $A=C_{14}H_{28}$; $Z=NH$; $W=C(O)CH(CH_2COOH)_2$; $X=O$-cellobioside; $R^1$=octanoyl; $R=H$; $V=OH$; Y and Q constitute a double bond.

In another embodiment, $A=C_{14}H_{28}$; $Z=NH$; $W=C(O)CH(CH_2COOH)_2$); $X=O$-cellobioside; $R^1$=octanoyl; $R=H$; $V=OH$; Y and Q constitute a triple bond.

In another embodiment, $A=C_{14}H_{28}$; $Z=NH$; $W=C(O)CH(CH_2COOH)_2$; $X=OH$; $R^1$=octanoyl; $R=H$; $V=O$-cellobioside; Y and Q constitute a double bond.

In another embodiment, $A=C_{14}H_{28}$; $Z=NH$; $W=C(O)CH(CH_2COOH)_2$; $X=OH$; $R^1$=octanoyl; $R=H$; $V=O$-cellobioside; Y and Q constitute a triple bond.

In another embodiment, $A=C_{14}H_{28}$; $Z=NH$; $W=C(O)CH(CH_2COOH)_2$; $X=OH$; $R^1$=octanoyl; $R=H$; $V=OH$; $Y=O$-cellobioside; $Q=H$.

In another embodiment, $A=C_{14}H_{28}$; $Z=NH$; $W=C(O)CH(CH_2COOH)_2$; $X=OH$; $R^1$=octanoyl; $R=H$; $V=OH$; $Y=H$; $Q=O$-cellobioside.

In another embodiment, $A=C_{14}H_{28}$; $Z=NH$; $W=C(O)CH(CH_2COOH)_2$; $X=O$-cellobioside; $R^1$=octanoyl; $R=H$; $V=OH$; $Y=H$; and $Q=H$.

In another embodiment, $A=C_{14}H_{28}$; $Z=NH$; $W=C(O)CH(CH_2COOH)_2$; $X=OH$; $R^1$=octanoyl; $R=H$; $V=O$-cellobioside; $Y=H$; and $Q=H$.

In another embodiment, $A=C_{14}H_{28}$; $Z=NH$; $W=C(O)CH(CH_2COOH)_2$; $X=H$; $R^1$=octanoyl; $R=H$; $V=O$-cellobioside; Y and Q constitute a double bond.

In another embodiment, A=$C_{14}H_{28}$; Z=NH; W=C(O)CH($CH_2$COOH)$_2$; X=H; $R^1$=octanoyl; R=H; V=O-cellobioside; Y and Q constitute a triple bond.

In another embodiment, A=$C_{14}H_{28}$; Z=NH; W=C(O)CH($CH_2$COOH)$_2$; X=H; $R^1$=octanoyl; R=H; V=OH; Y=O-cellobioside; Q=H.

In another embodiment, A=$C_{14}H_{28}$; Z=NH; W=C(O)CH($CH_2$COOH)$_2$; X=H; $R^1$=octanoyl; R=H; V=OH; Y=H; Q=O-cellobioside.

In another embodiment, A=$C_{14}H_{28}$; Z=NH; W=C(O)CH($CH_2$COOH)$_2$; X=H; $R^1$=octanoyl; R=H; V=O-cellobioside; Y=H; and Q=H.

In another embodiment, A=$C_{14}H_{28}$; Z=O; W=C(O)$CH_2CH_2$COOH; X=O-β-glucoronide; $R^1$=octanoyl; R=H; V=OH; Y and Q constitute a double bond.

In another embodiment, A=$C_{14}H_{28}$; Z=O; W=C(O)$CH_2CH_2$COOH; X=O-β-glucoronide; $R^1$=octanoyl; R=H; V=OH; Y and Q constitute a triple bond.

In another embodiment, A=$C_{14}H_{28}$; Z=O; W=C(O)$CH_2CH_2$COOH; X=OH; $R^1$=octanoyl; R=H; V=O-β-glucoronide; Y and Q constitute a double bond.

In another embodiment, A=$C_{14}H_{28}$; Z=O; W=C(O)$CH_2CH_2$COOH; X=OH; $R^1$=octanoyl; R=H; V=O-β-glucoronide; Y and Q constitute a triple bond.

In another embodiment, A=$C_{14}H_{28}$; Z=O; W=C(O)$CH_2CH_2$COOH; X=OH; $R^1$=octanoyl; R=H; V=OH; Y=O-β-glucoronide; Q=H.

In another embodiment, A=$C_{14}H_{28}$; Z=O; W=C(O)$CH_2CH_2$COOH; X=OH; $R^1$=octanoyl; R=H; V=OH; Y=H; Q=O-β-glucoronide.

In another embodiment, A=$C_{14}H_{28}$; Z=O; W=C(O)$CH_2CH_2$COOH; X=O-β-glucoronide; $R^1$=octanoyl; R=H; V=OH; Y=H; and Q=H.

In another embodiment, A=$C_{14}H_{28}$; Z=O; W=C(O)$CH_2CH_2$COOH; X=OH; $R^1$=octanoyl; R=H; V=O-β-glucoronide; Y=H; and Q=H.

In another embodiment, A=$C_{14}H_{28}$; Z=O; W=C(O)$CH_2CH_2$COOH; X=H; $R^1$=octanoyl; R=H; V=O-β-glucoronide; Y and Q constitute a double bond.

In another embodiment, A=$C_{14}H_{28}$; Z=O; W=C(O)$CH_2CH_2$COOH; X=H; $R^1$=octanoyl; R=H; V=O-β-glucoronide; Y and Q constitute a triple bond.

In another embodiment, A=$C_{14}H_{28}$; Z=O; W=C(O)$CH_2CH_2$COOH; X=H; $R^1$=octanoyl; R=H; V=OH; Y=O-β-glucoronide; Q=H.

In another embodiment, A=$C_{14}H_{28}$; Z=O; W=C(O)$CH_2CH_2$COOH; X=H; $R^1$=octanoyl; R=H; V=OH; Y=H; Q=O-β-glucoronide.

In another embodiment, A=$C_{14}H_{28}$; Z=O; W=C(O)$CH_2CH_2$COOH; X=H; $R^1$=octanoyl; R=H; V=O-β-glucoronide; Y=H; and Q=H.

In another embodiment, A=$C_{14}H_{28}$; Z=O; W=C(O)$CH_2CH_2$COOH; X=O-oligofructoside; $R^1$=octanoyl; R=H; V=OH; Y and Q constitute a double bond.

In another embodiment, A=$C_{14}H_{28}$; Z=O; W=C(O)$CH_2CH_2$COOH; X=O-oligofructoside; $R^1$=octanoyl; R=H; V=OH; Y and Q constitute a triple bond.

In another embodiment, A=$C_{14}H_{28}$; Z=O; W=C(O)$CH_2CH_2$COOH; X=OH; $R^1$=octanoyl; R=H; V=O-oligofructoside; Y and Q constitute a double bond.

In another embodiment, A=$C_{14}H_{28}$; Z=O; W=C(O)$CH_2CH_2$COOH; X=OH; $R^1$=octanoyl; R=H; V=O-oligofructoside; Y and Q constitute a triple bond.

In another embodiment, A=$C_{14}H_{28}$; Z=O; W=C(O)$CH_2CH_2$COOH; X=OH; $R^1$=octanoyl; R=H; V=OH; Y=O-oligofructoside; Q=H.

In another embodiment, A=$C_{14}H_{28}$; Z=O; W=C(O)$CH_2CH_2$COOH; X=OH; $R^1$=octanoyl; R=H; V=OH; Y=H; Q=O-oligofructoside.

In another embodiment, A=$C_{14}H_{28}$; Z=O; W=C(O)$CH_2CH_2$COOH; X=O-oligofructoside; $R^1$=octanoyl; R=H; V=OH; Y=H; and Q=H.

In another embodiment, A=$C_{14}H_{28}$; Z=O; W=C(O)$CH_2CH_2$COOH; X=OH; $R^1$=octanoyl; R=H; V=O-oligofructoside; Y=H; and Q=H.

In another embodiment, A=$C_{14}H_{28}$; Z=O; W=C(O)$CH_2CH_2$COOH; X=H; $R^1$=octanoyl; R=H; V=O-oligofructoside; Y and Q constitute a double bond.

In another embodiment, A=$C_{14}H_{28}$; Z=O; W=C(O)$CH_2CH_2$COOH; X=H; $R^1$=octanoyl; R=H; V=O-oligofructoside; Y and Q constitute a triple bond.

In another embodiment, A=$C_{14}H_{28}$; Z=O; W=C(O)$CH_2CH_2$COOH; X=H; $R^1$=octanoyl; R=H; V=OH; Y=O-oligofructoside; Q=H.

In another embodiment, A=$C_{14}H_{28}$; Z=O; W=C(O)$CH_2CH_2$COOH; X=H; $R^1$=octanoyl; R=H; V=OH; Y=H; Q=O-oligofructoside.

In another embodiment, A=$C_{14}H_{28}$; Z=O; W=C(O)$CH_2CH_2$COOH; X=H; $R^1$=octanoyl; R=H; V=O-oligofructoside; Y=H; and Q=H.

In another embodiment, A=$C_{14}H_{28}$; Z=O; W=C(O)$CH_2CH_2$COOH; X=O-fructoside; $R^1$=octanoyl; R=H; V=OH; Y and Q constitute a double bond.

In another embodiment, A=$C_{14}H_{28}$; Z=O; W=C(O)$CH_2CH_2$COOH; X=O-fructoside; $R^1$=octanoyl; R=H; V=OH; Y and Q constitute a triple bond.

In another embodiment, A=$C_{14}H_{28}$; Z=O; W=C(O)$CH_2CH_2$COOH; X=OH; $R^1$=octanoyl; R=H; V=O-fructoside; Y and Q constitute a double bond.

In another embodiment, A=$C_{14}H_{28}$; Z=O; W=C(O)$CH_2CH_2$COOH; X=OH; $R^1$=octanoyl; R=H; V=O-fructoside; Y and Q constitute a triple bond.

In another embodiment, A=$C_{14}H_{28}$; Z=O; W=C(O)$CH_2CH_2$COOH; X=OH; $R^1$=octanoyl; R=H; V=OH; Y=O-fructoside; Q=H.

In another embodiment, A=$C_{14}H_{28}$; Z=O; W=C(O)$CH_2CH_2$COOH; X=OH; $R^1$=octanoyl; R=H; V=OH; Y=H; Q=O-fructoside.

In another embodiment, A=$C_{14}H_{28}$; Z=O; W=C(O)$CH_2CH_2$COOH; X=O-fructoside; $R^1$=octanoyl; R=H; V=OH; Y=H; and Q=H.

In another embodiment, A=$C_{14}H_{28}$; Z=O; W=C(O)$CH_2CH_2$COOH; X=OH; $R^1$=octanoyl; R=H; V=O-fructoside; Y=H; and Q=H.

In another embodiment, A=$C_{14}H_{28}$; Z=O; W=C(O)$CH_2CH_2$COOH; X=H; $R^1$=octanoyl; R=H; V=O-fructoside; Y and Q constitute a double bond.

In another embodiment, A=$C_{14}H_{28}$; Z=O; W=C(O)CH2CH2COOH; X=H; $R^1$=octanoyl; R=H; V=O-fructoside; Y and Q constitute a triple bond.

In another embodiment, A=$C_{14}H_{28}$; Z=O; W=C(O)$CH_2CH_2$COOH; X=H; $R^1$=octanoyl; R=H; V=OH; Y=O-fructoside; Q=H.

In another embodiment, A=$C_{14}H_{28}$; Z=O; W=C(O)$CH_2CH_2$COOH; X=H; $R^1$=octanoyl; R=H; V=OH; Y=H; Q=O-fructoside.

In another embodiment, A=$C_{14}H_{28}$; Z=O; W=C(O)$CH_2CH_2$COOH; X=H; $R^1$=octanoyl; R=H; V=O-fructoside; Y=H; and Q=H.

In another embodiment, A=$C_{14}H_{28}$; Z=O; W=C(O)$CH_2CH_2$COOH; X=O-mannoside; $R^1$=octanoyl; R=H; V=OH; Y and Q constitute a double bond.

In another embodiment, A=$C_{14}H_{28}$; Z=O; W=C(O)$CH_2CH_2$COOH; X=O-mannoside; $R^1$=octanoyl; R=H; V=OH; Y and Q constitute a triple bond.

In another embodiment, A=$C_{14}H_{28}$; Z=O; W=C(O)$CH_2CH_2$COOH; X=OH; $R^1$=octanoyl; R=H; V=O-mannoside; Y and Q constitute a double bond.

In another embodiment, A=$C_{14}H_{28}$; Z=O; W=C(O)$CH_2CH_2COOH$; X=OH; $R^1$=octanoyl; R=H; V=O-mannoside; Y and Q constitute a triple bond.

In another embodiment, A=$C_{14}H_{28}$; Z=O; W=C(O)$CH_2CH_2COOH$; X=OH; $R^1$=octanoyl; R=H; V=OH; Y=O-mannoside; Q=H.

In another embodiment, A=$C_{14}H_{28}$; Z=O; W=C(O)$CH_2CH_2COOH$; X=OH; $R^1$=octanoyl; R=H; V=OH; Y=H; Q=O-mannoside.

In another embodiment, A=$C_{14}H_{28}$; Z=O; W=C(O)$CH_2CH_2COOH$; X=O-mannoside; $R^1$=octanoyl; R=H; V=OH; Y=H; and Q=H.

In another embodiment, A=$C_{14}H_{28}$; Z=O; W=C(O)$CH_2CH_2COOH$; X=OH; $R^1$=octanoyl; R=H; V=O-mannoside; Y=H; and Q=H.

In another embodiment, A=$C_{14}H_{28}$; Z=O; W=C(O)$CH_2CH_2COOH$; X=H; $R^1$=octanoyl; R=H; V=O-mannoside; Y and Q constitute a double bond.

In another embodiment, A=$C_{14}H_{28}$; Z=O; W=C(O)$CH_2CH_2COOH$; X=H; $R^1$=octanoyl; R=H; V=O-mannoside; Y and Q constitute a triple bond.

In another embodiment, A=$C_{14}H_{28}$; Z=O; W=C(O)$CH_2CH_2COOH$; X=H; $R^1$=octanoyl; R=H; V=OH; Y=O-mannoside; Q=H.

In another embodiment, A=$C_{14}H_{28}$; Z=O; W=C(O)$CH_2CH_2COOH$; X=H; $R^1$=octanoyl; R=H; V=OH; Y=H; Q=O-mannoside.

In another embodiment, A=$C_{14}H_{28}$; Z=O; W=C(O)$CH_2CH_2COOH$; X=H; $R^1$=octanoyl; R=H; V=O-mannoside; Y=H; and Q=H.

In another embodiment, A=$C_{14}H_{28}$; Z=O; W=C(O)$CH_2CH_2COOH$; X=O-cellobioside; $R^1$=octanoyl; R=H; V=OH; Y and Q constitute a double bond.

In another embodiment, A=$C_{14}H_{28}$; Z=O; W=C(O)$CH_2CH_2COOH$; X=O-cellobioside; $R^1$=octanoyl; R=H; V=OH; Y and Q constitute a triple bond.

In another embodiment, A=$C_{14}H_{28}$; Z=O; W=C(O)$CH_2CH_2COOH$; X=OH; $R^1$=octanoyl; R=H; V=O-cellobioside; Y and Q constitute a double bond.

In another embodiment, A=$C_{14}H_{28}$; Z=O; W=C(O)$CH_2CH_2COOH$; X=OH; $R^1$=octanoyl; R=H; V=O-cellobioside; Y and Q constitute a triple bond.

In another embodiment, A=$C_{14}H_{28}$; Z=O; W=C(O)$CH_2CH_2COOH$; X=OH; $R^1$=octanoyl; R=H; V=O-cellobioside; Q=H.

In another embodiment, A=$C_{14}H_{28}$; Z=O; W=C(O)$CH_2CH_2COOH$; X=OH; $R^1$=octanoyl; R=H; V=OH; Y=H; Q=O-cellobioside.

In another embodiment, A=$C_{14}H_{28}$; Z=O; W=C(O)$CH_2CH_2COOH$; X=O-cellobioside; $R^1$=octanoyl; R=H; V=OH; Y=H; Q=H.

In another embodiment, A=$C_{14}H_{28}$; Z=O; W=C(O)$CH_2CH_2COOH$; X=OH; $R^1$=octanoyl; R=H; V=O-cellobioside; Y=H; Q=H.

In another embodiment, A=$C_{14}H_{28}$; Z=O; W=C(O)$CH_2CH_2COOH$; X=H; $R^1$=octanoyl; R=H; V=O-cellobioside; Y and Q constitute a double bond.

In another embodiment, A=$C_{14}H_{28}$; Z=O; W=C(O)$CH_2CH_2COOH$; X=H; $R^1$=octanoyl; R=H; V=O-cellobioside; Y and Q constitute a triple bond.

In another embodiment, A=$C_{14}H_{28}$; Z=O; W=C(O)$CH_2CH_2COOH$; X=H; $R^1$=octanoyl; R=H; V=OH; Y=O-cellobioside; Q=H.

In another embodiment, A=$C_{14}H_{28}$; Z=O; W=C(O)$CH_2CH_2COOH$; X=H; $R^1$=octanoyl; R=H; V=OH; Y=H; Q=O-cellobioside.

In another embodiment, A=$C_{14}H_{28}$; Z=O; W=C(O)$CH_2CH_2COOH$; X=H; $R^1$=octanoyl; R=H; V=O-cellobioside; Y=H; and Q=H.

In another embodiment, A=$C_{14}H_{28}$; Z=NH; W=C(O)$CH_2CH_2COOH$; X=O-β-glucoronide; $R^1$=octanoyl; R=H; V=OH; Y and Q constitute a double bond.

In another embodiment, A=$C_{14}H_{28}$; Z=NH; W=C(O)$CH_2CH_2COOH$; X=O-β-glucoronide; $R^1$=octanoyl; R=H; V=OH; Y and Q constitute a triple bond.

In another embodiment, A=$C_{14}H_{28}$; Z=NH; W=C(O)$CH_2CH_2COOH$; X=OH; $R^1$=octanoyl; R=H; V=O-β-glucoronide; Y and Q constitute a double bond.

In another embodiment, A=$C_{14}H_{28}$; Z=NH; W=C(O)$CH_2CH_2COOH$; X=OH; $R^1$=octanoyl; R=H; V=O-β-glucoronide; Y and Q constitute a triple bond.

In another embodiment, A=$C_{14}H_{28}$; Z=NH; W=C(O)$CH_2CH_2COOH$; X=OH; $R^1$=octanoyl; R=H; V=OH; Y=O-β-glucoronide; Q=H.

In another embodiment, A=$C_{14}H_{28}$; Z=NH; W=C(O)$CH_2CH_2COOH$; X=OH; $R^1$=octanoyl; R=H; V=OH; Y=H; Q=O-β-glucoronide.

In another embodiment, A=$C_{14}H_{28}$; Z=NH; W=C(O)$CH_2CH_2COOH$; X=O-β-glucoronide; $R^1$=octanoyl; R=H; V=OH; Y=H; Q=H.

In another embodiment, A=$C_{14}H_{28}$; Z=NH; W=C(O)$CH_2CH_2COOH$; X=OH; $R^1$=octanoyl; R=H; V=O-β-glucoronide; Y=H; Q=H.

In another embodiment, A=$C_{14}H_{28}$; Z=NH; W=C(O)$CH_2CH_2COOH$; X=H; $R^1$=octanoyl; R=H; V=O-β-glucoronide; Y and Q constitute a double bond.

In another embodiment, A=$C_{14}H_{28}$; Z=NH; W=C(O)$CH_2CH_2COOH$; X=H; $R^1$=octanoyl; R=H; V=O-β-glucoronide; Y and Q constitute a triple bond.

In another embodiment, A=$C_{14}H_{28}$; Z=NH; W=C(O)$CH_2CH_2COOH$; X=H; $R^1$=octanoyl; R=H; V=OH; Y=O-β-glucoronide; Q=H.

In another embodiment, A=$C_{14}H_{28}$; Z=NH; W=C(O)$CH_2CH_2COOH$; X=H; $R^1$=octanoyl; R=H; V=OH; Y=H; Q=O-β-glucoronide.

In another embodiment, A=$C_{14}H_{28}$; Z=NH; W=C(O)$CH_2CH_2COOH$; X=H; $R^1$=octanoyl; R=H; V=O-β-glucoronide; Y=H; and Q=H.

In another embodiment, A=$C_{14}H_{28}$; Z=NH; W=C(O)$CH_2CH_2COOH$; X=O-oligofructoside; $R^1$=octanoyl; R=H; V=OH; Y and Q constitute a double bond.

In another embodiment, A=$C_{14}H_{28}$; Z=NH; W=C(O)$CH_2CH_2COOH$; X=O-oligofructoside; $R^1$=octanoyl; R=H; V=OH; Y and Q constitute a triple bond.

In another embodiment, A=$C_{14}H_{28}$; Z=NH; W=C(O)$CH_2CH_2COOH$; X=OH; $R^1$=octanoyl; R=H; V=O-oligofructoside; Y and Q constitute a double bond.

In another embodiment, A=$C_{14}H_{28}$; Z=NH; W=C(O)$CH_2CH_2COOH$; X=OH; $R^1$=octanoyl; R=H; V=-oligofructoside; Y and Q constitute a triple bond.

In another embodiment, A=$C_{14}H_{28}$; Z=NH; W=C(O)$CH_2CH_2COOH$; X=OH; $R^1$=octanoyl; R=H; V=OH; Y=O-oligofructoside; Q=H.

In another embodiment, A=$C_{14}H_{28}$; Z=NH; W=C(O)$CH_2CH_2COOH$; X=OH; $R^1$=octanoyl; R=H; V=OH; Y=H; Q=O-oligofructoside.

In another embodiment, A=$C_{14}H_{28}$; Z=NH; W=C(O)$CH_2CH_2COOH$; X=O-oligofructoside; $R^1$=octanoyl; R=H; V=OH; Y=H; Q=H.

In another embodiment, A=$C_{14}H_{28}$; Z=NH; W=C(O)$CH_2CH_2COOH$; X=OH; $R^1$=octanoyl; R=H; V=O-oligofructoside; Y=H; Q=H.

In another embodiment, A=$C_{14}H_{28}$; Z=NH; W=C(O)$CH_2CH_2COOH$; X=H; $R^1$=octanoyl; R=H; V=O-oligofructoside; Y and Q constitute a double bond.

In another embodiment, A=$C_{14}H_{28}$; Z=NH; W=C(O)$CH_2CH_2COOH$; X=H; $R^1$=octanoyl; R=H; V=O-oligofructoside; Y and Q constitute a triple bond.

In another embodiment, A=$C_{14}H_{28}$; Z=NH; W=C(O)CH$_2$CH$_2$COOH; X=H; R$^1$=octanoyl; R=H; V=OH; Y=O-oligofructoside; Q=H.

In another embodiment, A=$C_{14}H_{28}$; Z=NH; W=C(O)CH$_2$CH$_2$COOH; X=H; R$^1$=octanoyl; R=H; V=OH; Y=H; Q=oligofructoside.

In another embodiment, A=$C_{14}H_{28}$; Z=NH; W=C(O)CH$_2$CH$_2$COOH; X=H; R$^1$=octanoyl; R=H; V=O-oligofructoside; Y=H; and Q=H.

In another embodiment, A=$C_{14}H_{28}$; Z=NH; W=C(O)CH$_2$CH$_2$COOH; X=O-fructoside; R$^1$=octanoyl; R=H; V=OH; Y and Q constitute a double bond.

In another embodiment, A=$C_{14}H_{28}$; Z=NH; W=C(O)CH$_2$CH$_2$COOH; X=O-fructoside; R$^1$=octanoyl; R=H; V=OH; Y and Q constitute a triple bond.

In another embodiment, A=$C_{14}H_{28}$; Z=NH; W=C(O)CH$_2$CH$_2$COOH; X=OH; R$^1$=octanoyl; R=H; V=O-fructoside; Y and Q constitute a double bond.

In another embodiment, A=$C_{14}H_{28}$; Z=NH; W=C(O)CH$_2$CH$_2$COOH; X=OH; R$^1$=octanoyl; R=H; V=O-fructoside; Y and Q constitute a triple bond.

In another embodiment, A=$C_{14}H_{28}$; Z=NH; W=C(O)CH$_2$CH$_2$COOH; X=OH; R$^1$=octanoyl; R=H; V=OH; Y=O-fructoside; Q=H.

In another embodiment, A=$C_{14}H_{28}$; Z=NH; W=C(O)CH$_2$CH$_2$COOH; X=OH; R$^1$=octanoyl; R=H; V=OH; Y=H; Q=O-fructoside.

In another embodiment, A=$C_{14}H_{28}$; Z=NH; W=C(O)CH$_2$CH$_2$COOH; X=O-fructoside; R$^1$=octanoyl; R=H; V=OH; Y=H; and Q=H.

In another embodiment, A=$C_{14}H_{28}$; Z=NH; W=C(O)CH$_2$CH$_2$COOH; X=OH; R$^1$=octanoyl; R=H; V=O-fructoside; Y=H; and Q=H.

In another embodiment, A=$C_{14}H_{28}$; Z=NH; W=C(O)CH$_2$CH$_2$COOH; X=H; R$^1$=octanoyl; R=H; V=O-fructoside; Y and Q constitute a double bond.

In another embodiment, A=$C_{14}H_{28}$; Z=NH; W=C(O)CH$_2$CH$_2$COOH; X=H; R$^1$=octanoyl; R=H; V=O-fructoside; Y and Q constitute a triple bond.

In another embodiment, A=$C_{14}H_{28}$; Z=NH; W=C(O)CH$_2$CH$_2$COOH; X=H; R$^1$=octanoyl; R=H; V=OH; Y=O-fructoside; Q=H.

In another embodiment, A=$C_{14}H_{28}$; Z=NH; W=C(O)CH$_2$CH$_2$COOH; X=H; R$^1$=octanoyl; R=H; V=OH; Y=H; Q=O-fructoside.

In another embodiment, A=$C_{14}H_{28}$; Z=NH; W=C(O)CH$_2$CH$_2$COOH; X=H; R$^1$=octanoyl; R=H; V=O-fructoside; Y=H; and Q=H.

In another embodiment, A=$C_{14}H_{28}$; Z=NH; W=C(O)CH$_2$CH$_2$COOH; X=O-mannoside; R$^1$=octanoyl; R=H; V=OH; Y and Q constitute a double bond.

In another embodiment, A=$C_{14}H_{28}$; Z=NH; W=C(O)CH$_2$CH$_2$COOH; X=O-mannoside; R$^1$=octanoyl; R=H; V=OH; Y and Q constitute a triple bond.

In another embodiment, A=$C_{14}H_{28}$; Z=NH; W=C(O)CH$_2$CH$_2$COOH; X=OH; R$^1$=octanoyl; R=H; V=O-mannoside; Y and Q constitute a double bond.

In another embodiment, A=$C_{14}H_{28}$; Z=NH; W=C(O)CH$_2$CH$_2$COOH; X=OH; R$^1$=octanoyl; R=H; V=O-mannoside; Y and Q constitute a triple bond.

In another embodiment, A=$C_{14}H_{28}$; Z=NH; W=C(O)CH$_2$CH$_2$COOH; X=OH; R$^1$=octanoyl; R=H; V=OH; Y=O-mannoside; Q=H.

In another embodiment, A=$C_{14}H_{28}$; Z=NH; W=C(O)CH$_2$CH$_2$COOH; X=OH; R$^1$=octanoyl; R=H; V=OH; Y=H; Q=O-mannoside.

In another embodiment, A=$C_{14}H_{28}$; Z=NH; W=C(O)CH$_2$CH$_2$COOH; X=O-mannoside; R$^1$=octanoyl; R=H; V=OH; Y=H; and Q=H.

In another embodiment, A=$C_{14}H_{28}$; Z=NH; W=C(O)CH$_2$CH$_2$COOH; X=OH; R$^1$=octanoyl; R=H; V=O-mannoside; Y=H; and Q=H.

In another embodiment, A=$C_{14}H_{28}$; Z=NH; W=C(O)CH$_2$CH$_2$COOH; X=H; R$^1$=octanoyl; R=H; V=O-mannoside; Y and Q constitute a double bond.

In another embodiment, A=$C_{14}H_{28}$; Z=NH; W=C(O)CH$_2$CH$_2$COOH; X=H; R$^1$=octanoyl; R=H; V=O-mannoside; Y and Q constitute a triple bond.

In another embodiment, A=$C_{14}H_{28}$; Z=NH; W=C(O)CH$_2$CH$_2$COOH; X=H; R$^1$=octanoyl; R=H; V=OH; Y=O-mannoside; Q=H.

In another embodiment, A=$C_{14}H_{28}$; Z=NH; W=C(O)CH$_2$CH$_2$COOH; X=H; R$^1$=octanoyl; R=H; V=OH; Y=H; Q=O-mannoside.

In another embodiment, A=$C_{14}H_{28}$; Z=NH; W=C(O)CH$_2$CH$_2$COOH; X=H; R$^1$=octanoyl; R=H; V=O-mannoside; Y=H; and Q=H.

In another embodiment, A=$C_{14}H_{28}$; Z=NH; W=C(O)CH$_2$CH$_2$COOH; X=O-cellobioside; R$^1$=octanoyl; R=H; V=OH; Y and Q constitute a double bond.

In another embodiment, A=$C_{14}H_{28}$; Z=NH; W=C(O)CH$_2$CH$_2$COOH; X=O-cellobioside; R$^1$=octanoyl; R=H; V=OH; Y and Q constitute a triple bond.

In another embodiment, A=$C_{14}H_{28}$; Z=NH; W=C(O)CH$_2$CH$_2$COOH; X=OH; R$^1$=octanoyl; R=H; V=O-cellobioside; Y and Q constitute a double bond.

In another embodiment, A=$C_{14}H_{28}$; Z=NH; W=C(O)CH$_2$CH$_2$COOH; X=OH; R$^1$=octanoyl; R=H; V=O-cellobioside; Y and Q constitute a triple bond.

In another embodiment, A=$C_{14}H_{28}$; Z=NH; W=C(O)CH$_2$CH$_2$COOH; X=OH; R$^1$=octanoyl; R=H; V=OH; Y=O-cellobioside; Q=H.

In another embodiment, A=$C_{14}H_{28}$; Z=NH; W=C(O)CH$_2$CH$_2$COOH; X=OH; R$^1$=octanoyl; R=H; V=OH; Y=H; Q=O-cellobioside.

In another embodiment, A=$C_{14}H_{28}$; Z=NH; W=C(O)CH$_2$CH$_2$COOH; X=O-cellobioside; R$^1$=octanoyl; R=H; V=OH; Y=H; and Q=H.

In another embodiment, A=$C_{14}H_{28}$; Z=NH; W=C(O)CH$_2$CH$_2$COOH; X=OH; R$^1$=octanoyl; R=H; V=O-cellobioside; Y=H; and Q=H.

In another embodiment, A=$C_{14}H_{28}$; Z=NH; W=C(O)CH$_2$CH$_2$COOH; X=H; R$^1$=octanoyl; R=H; V=O-cellobioside; Y and Q constitute a double bond.

In another embodiment, A=$C_{14}H_{28}$; Z=NH; W=C(O)CH$_2$CH$_2$COOH; X=H; R$^1$=octanoyl; R=H; V=O-cellobioside; Y and Q constitute a triple bond.

In another embodiment, A=$C_{14}H_{28}$; Z=NH; W=C(O)CH$_2$CH$_2$COOH; X=H; R$^1$=octanoyl; R=H; V=OH; Y=O-cellobioside; Q=H.

In another embodiment, A=$C_{14}H_{28}$; Z=NH; W=C(O)CH$_2$CH$_2$COOH; X=H; R$^1$=octanoyl; R=H; V=OH; Y=H; Q=O-cellobioside.

In another embodiment, A=$C_{14}H_{28}$; Z=NH; W=C(O)CH$_2$CH$_2$COOH; X=H; R$^1$=octanoyl; R=H; V=O-cellobioside; Y=H; and Q=H.

In another embodiment, A=$C_{14}H_{28}$; Z=O; W=C(O)CH$_2$CH$_2$COOH; X=H; R$^1$=octanoyl; R=H; V=OH; Y=H; Q=OH.

In another embodiment, A=$C_{14}H_{28}$; Z=O; W=C(O)CH(CH$_2$COOH)$_2$;X=H; R$^1$ octanoyl; R=H; V=OH; Y=H; Q=OH.

In another embodiment, A=$C_{14}H_{28}$; Z=O; W=C(O)N(CH$_2$COOH)$_2$; X=H; R$^1$=octanoyl; R=H; V=OH; Y=H; Q=OH.

In another embodiment, A=$C_{14}H_{28}$; Z=O; W=C(O)CH$_2$CH$_2$COOH; X=H; R$^1$=H; R=H; V=OH; Y=H; Q=OH.

In another embodiment, $A=C_{14}H_{28}$; $Z=O$; $W=C(O)CH(CH_2COOH)_2$; $X=H$; $R^1=H$; $R=H$; $V=OH$; $Y=H$; $Q=OH$.

In another embodiment, $A=C_{14}H_{28}$; $Z=O$; $W=C(O)N(CH_2COOH)_2$; $X=H$; $R^1=H$; $R=H$; $V=OH$; $Y=H$; $Q=OH$.

In another embodiment, $A=C_{14}H_{28}$; $Z=O$; $W=C(O)CH_2CH_2COOH$; $X=H$; $R^1=palmitoyl$; $R=H$; $V=OH$; $Y=H$; $Q=OH$.

In another embodiment, $A=C_{14}H_{28}$; $Z=O$; $W=C(O)CH(CH_2COOH)_2$; $X=H$; $R^1=palmitoyl$; $R=H$; $V=OH$; $Y=H$; $Q=OH$.

In another embodiment, $A=C_{14}H_{28}$; $Z=O$; $W=C(O)N(CH_2COOH)_2$; $X=H$; $R^1=palmitoyl$; $R=H$; $V=OH$; $Y=H$; $Q=OH$.

In another embodiment, $A=C_{14}H_{28}$; $Z=NH$; $W=C(O)CH_2CH_2COOH$; $X=H$; $R^1=octanoyl$; $R=H$; $V=OH$; $Y=H$; $Q=OH$.

In another embodiment, $A=C_{14}H_{28}$; $Z=NH$; $W=C(O)CH(CH_2COOH)_2$; $X=H$; $R^1=octanoyl$; $R=H$; $V=OH$; $Y=H$; $Q=OH$.

In another embodiment, $A=C_{14}H_{28}$; $Z=NH$; $W=C(O)(CH_2COOH)_2$; $X=H$; $R^1=octanoyl$; $R=H$; $V=OH$; $Y=H$; $Q=OH$.

In another embodiment, $A=C_{14}H_{28}$; $Z=NH$; $W=C(O)CH_2CH_2COOH$; $X=H$; $R^1=H$; $R=H$; $V=OH$; $Y=H$; $Q=OH$.

In another embodiment, $A=C_{14}H_{28}$; $Z=NH$; $W=C(O)CH(CH_2COOH)_2$; $X=H$; $R^1=H$; $R=H$; $V=OH$; $Y=H$; $Q=OH$.

In another embodiment, $A=C_{14}H_{28}$; $Z=NH$; $W=C(O)N(CH_2COOH)_2$; $X=H$; $R^1=H$; $R=H$; $V=OH$; $Y=H$; $Q=OH$.

In another embodiment, $A=C_{14}H_{28}$; $Z=NH$; $W=C(O)CH_2CH_2COOH$; $X=H$; $R^1=palmitoyl$; $R=H$; $V=OH$; $Y=H$; $Q=OH$.

In another embodiment, $A=C_{14}H_{28}$; $Z=NH$; $W=C(O)CH(CH_2COOH)_2$; $X=H$; $R^1=palmitoyl$; $R=H$; $V=OH$; $Y=H$; $Q=OH$.

In another embodiment, $A=C_{14}H_{28}$; $Z=NH$; $W=C(O)N(CH_2COOH)_2$; $X=H$; $R^1=palmitoyl$; $R=H$; $V=OH$; $Y=H$; $Q=OH$.

In another embodiment, $A=C_{14}H_{28}$; $Z=O$; $W=C(O)CH_2CH_2COOH)$; $X=H$; $R^1=octanoyl$; $R=H$; $V=O-\beta$-glucoronide; $Y=H$; $Q=OH$.

In another embodiment, $A=C_{14}H_{28}$; $Z=O$; $W=C(O)CH(CH_2COOH)_2$; $X=H$; $R^1=octanoyl$; $R=H$; $V=O-\beta$-glucoronide; $Y=H$; $Q=OH$.

In another embodiment, $A=C_{14}H_{28}$; $Z=O$; $W=C(O)N(CH_2COOH)_2$; $X=H$; $R^1=octanoyl$; $R=H$; $V=O-O-\beta$-glucoronide; $Y=H$; $Q=OH$.

In another embodiment, $A=C_{14}H_{28}$; $Z=O$; $W=C(O)CH_2CH_2COOH)$; $X=H$; $R^1=H$; $R=H$; $V=O-\beta$-glucoronide; $Y=H$; $Q=OH$.

In another embodiment, $A=C_{14}H_{28}$; $Z=O$; $W=C(O)CH(CH_2COOH)_2$; $X=H$; $R^1=H$; $R=H$; $V=O-\beta$-glucoronide; $Y=H$; $Q=OH$.

In another embodiment, $A=C_{14}H_{28}$; $Z=O$; $W=C(O)N(CH_2COOH)_2$; $X=H$; $R^1=H$; $R=H$; $V=O-\beta$-glucoronide; $Y=H$; $Q=OH$.

In another embodiment, $A=C_{14}H_{28}$; $Z=O$; $W=C(O)CH_2CH_2COOH$; $X=H$; $R^1=palmitoyl$; $R=H$; $V=O-\beta$-glucoronide; $Y=H$; $Q=OH$.

In another embodiment, $A=C_{14}H_{28}$; $Z=O$; $W=C(O)CH(CH_2COOH)_2$; $X=H$; $R^1=palmitoyl$; $R=H$; $V=O-\beta$-glucoronide; $Y=H$; $Q=OH$.

In another embodiment, $A=C_{14}H_{28}$; $Z=O$; $W=C(O)N(CH_2COOH)_2$; $X=H$; $R^1=palmitoyl$; $R=H$; $V=O-\beta$-glucoronide; $Y=H$; $Q=OH$.

In another embodiment, $A=C_{14}H_{28}$; $Z=NH$; $W=C(O)CH_2CH_2COOH)$; $X=H$; $R^1=octanoyl$; $R=H$; $V=O-\beta$-glucoronide; $Y=H$; $Q=OH$.

In another embodiment, $A=C_{14}H_{28}$; $Z=NH$; $W=C(O)CH(CH_2COOH)_2$; $X=H$; $R^1=octanoyl$; $R=H$; $V=O-\beta$-glucoronide; $Y=H$; $Q=OH$.

In another embodiment, $A=C_{14}H_{28}$; $Z=NH$; $W=C(O)N(CH_2COOH)_2$; $X=H$; $R^1=octanoyl$; $R=H$; $V=O-\beta$-glucoronide; $Y=H$; $Q=OH$.

In another embodiment, $A=C_{14}H_{28}$; $Z=NH$; $W=C(O)CH_2CH_2COOH)$; $X=H$; $R^1=H$; $R=H$; $V=O-\beta$-glucoronide; $Y=H$; $Q=OH$.

In another embodiment, $A=C_{14}H_{28}$; $Z=NH$; $W=C(O)CH(CH_2COOH)_2$; $X=H$; $R^1=H$; $R=H$; $V=O-\beta$-glucoronide; $Y=H$; $Q=OH$.

In another embodiment, $A=C_{14}H_{28}$; $Z=NH$; $W=C(O)N(CH_2COOH)_2$; $X=H$; $R^1=H$; $R=H$; $V=O-\beta$-glucoronide; $Y=H$; $Q=OH$.

In another embodiment, $A=C_{14}H_{28}$; $Z=NH$; $W=C(O)CH_2CH_2COOH)$; $X=H$; $R^1=palmitoyl$; $R=H$; $V=O-\beta$-glucoronide; $Y=H$; $Q=OH$.

In another embodiment, $A=C_{14}H_{28}$; $Z=NH$; $W=C(O)CH(CH_2COOH)_2$; $X=H$; $R^1=palmitoyl$; $R=H$; $V=O-\beta$-glucoronide; $Y=H$; $Q=OH$.

In another embodiment, $A=C_{14}H_{28}$; $Z=NH$; $W=C(O)N(CH_2COOH)_2$; $X=H$; $R^1=palmitoyl$; $R=H$; $V=O-\beta$-glucoronide; $Y=H$; $Q=OH$.

In another embodiment, $A=C_{14}H_{28}$; $Z=O$; $W=C(O)CH_2CH_2COOH)$; $X=H$; $R^1=octanoyl$; $R=H$; $V=OH$; $Y=H$; $Q=O-\beta$-glucoronide.

In another embodiment, $A=C_{14}H_{28}$; $Z=O$; $W=C(O)CH(CH_2COOH_2$; $X=H$; $R^1=octanoyl$; $R=H$; $V=OH$; $Y=H$; $Q=O-\beta$-glucoronide.

In another embodiment, $A=C_{14}H_{28}$; $Z=O$; $W=C(O)N(CH_2COOH)_2$; $X=H$; $R^1=octanoyl$; $R=H$; $V=OH$; $Y=H$; $Q=O-\beta$-glucoronide.

In another embodiment, $A=C_{14}H_{28}$; $Z=O$; $W=C(O)CH_2CH_2COOH)$; $X=H$; $R^1=H$; $R=H$; $V=OH$; $Y=H$; $Q=O-\beta$-glucoronide.

In another embodiment, $A=C_{14}H_{28}$; $Z=O$; $W=C(O)CH(CH_2COOH)_2$; $X=H$; $R^1=H$; $R=H$; $V=OH$; $Y=H$; $Q=O-\beta$-glucoronide.

In another embodiment, $A=C_{14}H_{28}$; $Z=O$; $W=C(O)N(CH_2COOH)_2$; $X=H$; $R^1H$; $R=H$; $V=OH$; $Y=H$; $Q=O-\beta$-glucoronide.

In another embodiment, $A=C_{14}H_{28}$; $Z=O$; $W=C(O)CH_2CH_2COOH$; $X=H$; $R^1=palmitoyl$; $R=H$; $V=OH$; $Y=H$; $Q=)-\beta$-glucoronide.

In another embodiment, $A=C_{14}H_{28}$; $Z=O$; $W=C(O)CH(CH_2COOH)_2$; $X=H$; $R^1=palmitoyl$; $R=H$; $V=OH$; $Y=H$; $Q=O-\beta$-glucoronide.

In another embodiment, $A=C_{14}H_{28}$; $Z=O$; $W=C(O)N(CH_2COOH)_2$; $X=H$; $R^1=palmitoyl$; $R=H$; $V=OH$; $Y=H$; $Q=O-\beta$-glucoronide.

In another embodiment, $A=C_{14}H_{28}$; $Z=NH$; $W=C(O)CH_2CH_2COOH$; $X=H$; $R^1octanoyl$; $R=H$; $V=OH$; $Y=H$; $Q=O-\beta$-glucoronide.

In another embodiment, $A=C_{14}H_{28}$; $Z=NH$; $W=C(O)CH(CH_2COOH)_2$; $X=H$; $R^1octanoyl$; $R=H$; $V=OH$; $Y=H$; $Q=O-\beta$-glucoronide.

In another embodiment; $A=C_{14}H_{28}$; $Z=NH$; $W=C(O)N(CH_2COOH)_2$; $X=H$; $R^1=octanoyl$; $R=H$; $V=OH$; $Y=H$; $Q=O-\beta$-glucoronide.

In another embodiment, $A=C_{14}H_{28}$; $Z=NH$; $W=C(O)CH_2CH_2COOH$; $X=H$; $R^1=H$; $R=H$; $V=OH$; $Y=H$; $Q=O-\beta$-glucoronide.

In another embodiment, $A=C_{14}H_{28}$; $Z=NH$; $W=C(O)CH(CH_2COOH)_2$; $X=H$; $R^1H$; $R=H$; $V=OH$; $Y=H$; $Q=O-\beta$-glucoronide.

In another embodiment, $A=C_{14}H_{28}$; $Z=NH$; $W=C(O)N(CH_2COOH)_2$; $X=H$; $R^1H$; $R=H$; $V=OH$; $Y=H$; $Q=O-\beta$-glucoronide.

In another embodiment, $A=C_{14}H_{28}$; $Z=NH$; $W=C(O)CH_2CH_2COOH$; $X=H$; $R^1$palmitoyl; $R=H$; $V=OH$; $Y=H$; $Q=O$-β-glucoronide.

In another embodiment, $A=C_{14}H_{28}$; $Z=NH$; $W=C(O)CH(CH_2COOH)_2$; $X=H$; $R^1$=palmitoyl $R=H$; $V=OH$; $Y=H$; $Q=O$-β-glucoronide.

In another embodiment, $A=C_{14}H_{28}$; $Z=NH$; $W=C(O)N(CH_2COOH)_2$; $X=H$; $R^1$=palmitoyl; $R=H$; $V=OH$; $Y=H$; $Q=O$-β-glucoronide.

In another embodiment, $A=C_{14}H_{28}Z=O$; $W=C(O)CH_2CH_2COOH$; $X=H$; $R^1$octanoyl; $R=H$; $V=O$-oligofructoside; $Y=H$; $Q=OH$.

In another embodiment, $A=C_{14}H_{28}$; $Z=O$; $W=C(O)CH(CH_2COOH$; $X=H$; $R^1$=octanoyl; $R=H$; $V=O$-oligofructoside; $Y=H$; $Q=OH$.

In another embodiment, $A=C_{14}H_{28}$; $Z=O$; $W=C(O)N(CH_2COOH)_2$; $X=H$; $R^1$=octanoyl; $R=H$; $V=O$-oligofructoside; $Y=H$; $Q=OH$.

In another embodiment, $A=C_{14}H_{28}$; $Z=O$; $W=C(O)CH_2CH_2COOH)$; $X=H$; $R^1=H$; $R=H$; $V=O$-oligofructoside; $Y=H$; $Q=OH$.

In another embodiment, $A=C_{14}H_{28}$; $Z=O$; $W=C(O)CH(CH_2COOH)_2$; $X=H$; $R^1H$; $R=H$; $V=O$-oligofructoside; $Y=H$; $Q=OH$.

In another embodiment, $A=C_{14}H_{28}$; $Z=O$; $W=C(O)N(CH_2COOH)_2$; $X=H$; $R^1H$; $R=H$; $V=O$-oligofructoside; $Y=H$; $Q=OH$.

In another embodiment; $A=C_{14}H_{28}$; $Z=O$; $W=C(O)CH_2CH_2COOH)$; $X=H$; $R^1$=palmitoyl; $R=H$; $V=O$-oligofructoside; $Y=H$; $Q=OH$.

In another embodiment, $A=C_{14}H_{28}$; $Z=O$; $W=C(O)CH(CH_2COOH)_2$; $X=H$; $R^1$=palmitoyl; $R=H$; $V=O$-oligofructoside; $Y=H$; $Q=OH$.

In another embodiment, $A=C_{14}H_{28}$; $Z=O$; $W=C(O)N(CH_2COOH)_2$; $X=H$; $R^1$palmitoyl; $R=H$; $V=O$-oligofructoside; $Y=H$; $Q=OH$.

In another embodiment, $A=C_{14}H_{28}$; $Z=NH$; $W=C(O)CH_2CH_2COOH)$; $X=H$; $R^1$octanoyl; $R=H$; $V=O$-oligofructoside; $Y=H$; $Q=OH$.

In another embodiment, $A=C_{14}H_{28}$; $Z=NH$; $W=C(O)CH(CH_2COOH)_2$; $X=H$; $R^1$octanoyl; $R=H$; $V=O$-oligofructoside; $Y=H$; $Q=OH$.

In another embodiment, $A=C_{14}H_{28}$; $Z=NH$; $W=C(O)N(CH_2COOH)_2$; $X=H$; $R^1$=octanoyl; $R=H$; $V=O$-oligofructoside; $Y=H$; $Q=OH$.

In another embodiment, $A=C_{14}H_{28}$; $Z=NH$; $W=C(O)CH_2CH_2COOH)$; $X=H$; $R^1=H$; $R=H$; $V=O$-oligofructoside; $Y=H$; $Q=OH$.

In another embodiment, $A=C_{14}H_{28}$; $Z=NH$; $W=C(O)CH(CH_2COOH)_2$; $X=H$; $R^1H$; $R=H$; $V=O$-oligofructoside; $Y=H$; $Q=OH$.

In another embodiment, $A=C_{14}H_{28}$; $Z=NH$; $W=C(O)N(CH_2COOH)_2$; $X=H$; $R^1=H$; $R=H$; $V=O$-oligofructoside; $Y=H$; $Q=OH$.

In another embodiment, $A=C_{14}H_{28}$; $Z=NH$; $W=C(O)CH_2CH_2COOH)$; $X=H$; $R^1$=palmitoyl; $R=H$; $V=O$-oligofructoside; $Y=H$; $Q=OH$.

In another embodiment, $A=C_{14}H_{28}$; $Z=NH$; $W=C(O)CH(CH_2COOH)_2$; $X=H$; $R^1$palmitoyl; $R=H$; $V=O$-oligofructoside; $Y=H$; $Q=OH$.

In another embodiment, $A=C_{14}H_{28}$; $Z=NH$; $W=C(O)N(CH_2COOH)_2$; $X=H$; $R^1$palmitoyl; $R=H$; $V=O$-oligofructoside; $Y=H$; $Q=OH$.

In another embodiment, $A=C_{14}H_{28}$; $Z=O$; $W=C(O)CH_2CH_2COOH$; $X=H$; $R^1$octanoyl; $R=H$; $V=OH$; $Y=H$; $Q=O$-oligofructoside.

In another embodiment; $A=C_{14}H_{28}$; $Z=O$; $W=C(O)CH(CH_2COOH)_2$; $X=H$; $R^1$=octanoyl; $R=H$; $V=OH$; $Y=H$; $Q=O$-oligofructoside.

In another embodiment, $A=C_{14}H_{28}$; $Z=O$; $W=C(O)N(CH_2COOH)_2$; $X=H$; $R^1$=octanoyl; $R=H$; $V=OH$; $Y=H$; $Q=O$-oligofructoside.

In another embodiment, $A=C_{14}H_{28}$; $Z=O$; $W=C(O)CH_2CH_2COOH)$; $X=H$; $R^1H$; $R=H$; $V=OH$; $Y=H$; $Q=O$-oligofructoside.

In another embodiment, $A=C_{14}H_{28}$; $Z=O$; $W=C(O)CH(CH_2COOH)$; $X=H$; $R^1H$; $R=H$; $V=OH$; $Y=H$; $Q=O$-oligofructoside.

In another embodiment, $A=C_{14}H_{28}$; $Z=O$; $W=C(O)N(CH_2COOH)_2$; $X=H$; $R^1H$; $R=H$; $V=OH$; $Y=H$; $Q=O$-oligofructoside.

In another embodiment, $A=C_{14}H_{28}$; $Z=O$; $W=C(O)CH_2CH_2COOH)$; $X=H$; $R^1$=palmitoyl; $R=H$; $V=OH$; $Y=H$; $Q=O$-oligofructoside.

In another embodiment, $A=C_{14}H_{28}$; $Z=O$; $W=C(O)CH(CH_2COOH)_2$; $X=H$; $R^1$=palmitoyl; $R=H$; $V=OH$; $Y=H$; $Q=O$-oligofructoside.

In another embodiment, $A=C_{14}H_{28}$; $Z=O$; $W=C(O)N(CH_2COOH)_2$; $X=H$; $R^1$palmitoyl; $R=H$; $V=OH$; $Y=H$; $Q=O$-oligofructoside.

In another embodiment, $A=C_{14}H_{28}$; $Z=NH$; $W=C(O)CH_2CH_2COOH$; $X=H$; $R^1$=octanoyl; $R=H$; $V=OH$; $Y=H$; $Q=O$-oligofructoside.

In another embodiment, $A=C_{14}H_{28}$; $Z=NH$; $W=C(O)CH(CH_2COOH)_2$; $X=H$; $R^1$=octanoyl; $R=H$; $V=OH$; $Y=H$; $Q=O$-oligofructoside.

In another embodiment, $A=C_{14}H_{28}$; $Z=NH$; $W=C(O)N(CH_2COOH)_2$; $X=H$; $R^1$=octanoyl; $R=H$; $V=OH$; $Y=H$; $Q=O$-oligofructoside.

In another embodiment, $A=C_{14}H_{28}$; $Z=NH$; $W=C(O)CH_2CH_2COOH)$; $X=H$; $R^1H$; $R=H$; $V=OH$; $Y=H$; $Q=O$-oligofructoside.

In another embodiment, $A=C_{14}H_{28}$; $Z=NH$; $W=C(O)CH(CH_2COOH)_2$; $X=H$; $R^1H$; $R=H$; $V=OH$; $Y=H$; $Q=O$-oligofructoside.

In another embodiment; $A=C_{14}H_{28}$; $Z=NH$; $W=C(O)N(CH_2COOH)_2$; $X=H$; $R^1H$; $R=H$; $V=OH$; $Y=H$; $Q=O$-oligofructoside.

In another embodiment, $A=C_{14}H_{28}$; $Z=NH$; $W=C(O)CH_2CH_2COOH$; $X=H$; $R^1$=palmitoyl; $R=H$; $V=OH$; $Y=H$; $Q=O$-oligofructoside.

In another embodiment, $A=C_{14}H_{28}$; $Z=NH$; $W=C(O)CH(CH_2COOH)_2$; $X=H$; $R^1$palmitoyl; $R=H$; $V=OH$; $Y=H$; $Q=O$-oligofructoside.

In another embodiment, $A=C_{14}H_{28}$; $Z=NH$; $W=C(O)N(CH_2COOH)_2$; $X=H$; $R^1$palmitoyl; $R=H$; $V=OH$; $Y=H$; $Q=O$-oligofructoside.

In another embodiment, $A=C_{14}H_{28}$; $Z=O$; $W=C(O)CH_2CH_2COOH)$; $X=H$; $R^1$octanoyl; $R=H$; $V=O$-fructoside; $Y=H$; $Q=OH$.

In another embodiment, $A=C_{14}H_{28}$; $Z=O$; $W=C(O)CH(CH_2COOH)_2$; $X=H$; $R^1$=octanoyl; $R=H$; $V=O$-fructoside; $Y=H$; $Q=OH$.

In another embodiment, $A=C_{14}H_{28}$; $Z=O$; $W=C(O)N(CH_2COOH)_2$; $X=H$; $R^1$=octanoyl; $R=H$; $V=O$-O-fructoside; $Y=H$; $Q=OH$.

In another embodiment, $A=C_{14}H_{28}$; $Z=O$; $W=C(O)CH_2CH_2COOH)$; $X=H$; $R^1H$; $R=H$; $V=O$-fructoside; $Y=H$; $Q=OH$.

In another embodiment, $A=C_{14}H_{28}$; $Z=O$; $W=C(O)CH(CH_2COOH)_2$; $X=H$; $R^1=H$; $R=H$; $V=O$-fructoside; $Y=H$; $Q=OH$.

In another embodiment, $A=C_{14}H_{28}$; $Z=O$; $W=C(O)N(CH_2COOH)_2$; $X=H$; $R^1=H$; $R=H$; $V=O$-fructoside; $Y=H$; $Q=OH$.

In another embodiment, $A=C_{14}H_{28}$; $Z=O$; $W=C(O)CH_2CH_2COOH)$; $X=H$; $R^1$=palmitoyl; $R=H$; $V=O$-fructoside; $Y=H$; $Q=OH$.

In another embodiment, A=$C_{14}H_{28}$; Z=O; W=C(O)CH($CH_2COOH$)$_2$; X=H; $R^1$palmitoyl; R=H; V=O-fructoside; Y=H; Q=OH.

In another embodiment, A=$C_{14}H_{28}$; Z=O; W=C(O)N($CH_2COOH$)$_2$; X=H; $R^1$palmitoyl; R=H; V=O-fructoside; Y=H; Q=OH.

In another embodiment; A=$C_{14}H_{28}$; Z=NH; W=C(O)$CH_2CH_2COOH$); X=H; $R^1$octanoyl; R=H; V=O-fructoside; Y=H; Q=OH.

In another embodiment, A=$C_{14}H_{28}$; Z=NH; W=C(O)CH($CH_2COOH$)$_2$; X=H; $R^1$=octanoyl; R=H; V=O-fructoside; Y=H; Q=OH.

In another embodiment, A=$C_{14}H_{28}$; Z=NH; W=C(O)N($CH_2COOH$)$_2$; X=H; $R^1$octanoyl; R=H; V=O-fructoside; Y=H; Q=OH.

In another embodiment, A=$C_{14}H_{28}$; Z=NH; W=C(O)$CH_2CH_2COOH$)$_2$; X=H; $R^1$H; R=H; V=O-fructoside; Y=H; Q=OH.

In another embodiment, A=$C_{14}H_{28}$; Z=NH; W=C(O)CH($CH_2COOH$)$_2$; X=H; $R^1$H; R=H; V=O-fructoside; Y=H; Q=OH.

In another embodiment, A=$C_{14}H_{28}$; Z=NH; W=C(O)N($CH_2COOH$)$_2$; X=H; $R^1$=H; R=H; V=O-fructoside; Y=H; Q=OH.

In another embodiment, A=$C_{14}H_{28}$; Z=NH; W=C(O)$CH_2CH_2COOH$)$_2$; X=H; $R^1$=palmitoyl; R=H; V=O-fructoside; Y=H; Q=OH.

In another embodiment, A=$C_{14}H_{28}$; Z=NH; W=C(O)CH($CH_2COOH$)$_2$; X=H; $R^1$=palmitoyl; R=H; V=O-fructoside; Y=H; Q=OH.

In another embodiment, A=$C_{14}H_{28}$; Z=NH; W=C(O)N($CH_2COOH$)$_2$; X=H; $R^1$=palmitoyl; R=H; V=O-fructoside; Y=H Q=OH.

In another embodiment, A=$C_{14}H_{28}$; Z=O; W=C(O)$CH_2CH_2COOH$); X=H; $R^1$=octanoyl; R=H; V=OH; Y=H; Q=O-fructoside.

In another embodiment, A=$C_{14}H_{28}$; Z=O; W=C(O)CH($CH_2COOH$)$_2$; X=H; $R^1$octanoyl; R=H; V=OH; Y=H; Q=O-fructoside.

In another embodiment, A=$C_{14}H_{28}$; Z=O; W=C(O)N($CH_2COOH$)$_2$; X=H; $R^1$octanoyl; R=H; V=OH; Y=H; Q=O-fructoside.

In another embodiment; A=$C_{14}H_{28}$; Z=O; W=C(O)CH2CH2COOH); X=H; $R^1$=H; R=H; V=OH; Y=H; Q=O-fructoside.

In another embodiment, A=$C_{14}H_{28}$; Z=O; W=C(O)CH($CH_2COOH$)$_2$; X=H; $R^1$=H; R=H; V=OH; Y=H; Q=O-fructoside.

In another embodiment, A=$C_{14}H_{28}$; Z=O; W=C(O)N($CH_2COOH$)$_2$; X=H; $R^1$H; R=H; V=OH; Y=H; Q=O-fructoside.

In another embodiment, A=$C_{14}H_{28}$; Z=O; W=C(O)$CH_2CH_2COOH$); X=H; $R^1$palmitoyl; R=H; V=OH; Y=H; Q=O-fructoside.

In another embodiment, A=$C_{14}H_{28}$; Z=O; W=C(O)CH($CH_2COOH$)$_2$; X=H; $R^1$palmitoyl; R=H; V=OH; Y=H; Q=O-fructoside.

In another embodiment, A=$C_{14}H_{28}$; Z=O; W=C(O)N($CH_2COOH$)$_2$; X=H; $R^1$=palmitoyl; R=H; V=OH; Y=H; Q=O-fructoside.

In another embodiment, A=$C_{14}H_{28}$; Z=NH; W=C(O)$CH_2CH_2COOH$)$_2$; X=H; $R^1$=octanoyl; R=H; V=OH; Y=H; Q=O-fructoside.

In another embodiment, A=$C_{14}H_{28}$; Z=NH; W=C(O)CH($CH_2COOH$)$_2$; X=H; $R^1$=octanoyl; R=H; V=OH; Y=H; Q=O-fructoside.

In another embodiment, A=$C_{14}H_{28}$; Z=NH; W=C(O)N($CH_2COOH$)$_2$; X=H; $R^1$=octanoyl; R=H; V=OH; Y=H; Q=O-fructoside.

In another embodiment, A=$C_{14}H_{28}$; Z=NH; W=C(O)$CH_2CH_2COOH$); X=H; $R^1$=H; R=H; V=OH; Y=H; Q=O-fructoside.

In another embodiment, A=$C_{14}H_{28}$; Z=NH; W=C(O)CH($CH_2COOH$)$_2$; X=H; $R^1$=H; R=H; V=OH; Y=H; Q=O-fructoside.

In another embodiment, A=$C_{14}H_{28}$; Z=NH; W=C(O)N($CH_2COOH$)$_2$; X=H; $R^1$H; R=H; V=OH; Y=H; Q=O-fructoside.

In another embodiment, A=$C_{14}H_{28}$; Z=NH; W=C(O)($CH_2CH_2COOH$); X=H; $R^1$palmitoyl; R=H; V=OH; Y=H; Q=O-fructoside.

In another embodiment; A=$C_{14}H_{28}$; Z=NH; W=C(O)CH($CH_2COOH$)$_2$; X=H; $R^1$=palmitoyl; R=H; V=OH; Y=H; Q=O-fructoside.

In another embodiment, A=$C_{14}H_{28}$; Z=NH; W=C(O)N($CH_2COOH$)$_2$; X=H; $R^1$=palmitoyl; R=H; V=OH; Y=H; Q=O-fructoside.

In another embodiment, A=$C_{14}H_{28}$; Z=O; W=C(O)($CH_2CH_2COOH$); X=H; $R^1$octanoyl; R=H; V=O-mannoside; Y=H; Q=OH.

In another embodiment, A=$C_{14}H_{28}$; Z=O; W=C(O)CH($CH_2COOH$)$_2$; X=H; $R^1$octanoyl; R=H; V=O-mannoside; Y=H; Q=OH.

In another embodiment, A=$C_{14}H_{28}$; Z=O; W=C(O)N($CH_2COOH$)$_2$; X=H; $R^1$octanoyl; R=H; V=O-O-mannoside; Y=H; Q=OH.

In another embodiment, A=$C_{14}H_{28}$; Z=O; W=C(O)$CH_2CH_2COOH$); X=H; $R^1$=H; R=H; V=O-mannoside; Y=H; Q=OH.

In another embodiment, A=$C_{14}H_{28}$; Z=O; W=C(O)CH($CH_2COOH$)$_2$; X=H; $R^1$=H; R=H; V=O-mannoside; Y=H; Q=OH.

In another embodiment, A=$C_{14}H_{28}$; Z=O; W=C(O)N($CH_2COOH$)$_2$; X=H; $R^1$=H; R=H; V=O-mannoside; Y=H; Q=OH.

In another embodiment, A=$C_{14}H_{28}$; Z=O; W=C(O)$CH_2CH_2COOH$); X=H; $R^1$=palmitoyl; R=H; V=O-mannoside; Y=H; Q=OH.

In another embodiment, A=$C_{14}H_{28}$; Z=O; W=C(O)CH($CH_2COOH$)$_2$; X=H; $R^1$=palmitoyl; R=H; V=O-mannoside; Y=H; Q=OH.

In another embodiment, A=$C_{14}H_{28}$; Z=O; W=C(O)N($CH_2COOH$)$_2$; X=H; $R^1$=palmitoyl; R=H; V=O-mannoside; Y=H; Q=OH.

In another embodiment, A=$C_{14}H_{28}$; Z=NH; W=C(O)$CH_2CH_2COOH$); X=H; $R^1$octanoyl; R=H; V=O-mannoside; Y=H; Q=OH.

In another embodiment, A=$C_{14}H_{28}$; Z=NH; W=C(O)CH($CH_2COOH$)$_2$; X=H; $R^1$octanoyl; R=H; V=O-mannoside; Y=H; Q=OH.

In another embodiment; A=$C_{14}H_{28}$; Z=NH; W=C(O)N($CH_2COOH$)$_2$; X=H; $R^1$=octanoyl; R=H; V=O-mannoside; Y=H; Q=OH.

In another embodiment, A=$C_{14}H_{28}$; Z=NH; W=C(O)$CH_2CH_2COOH$); X=H; $R^1$=H; R=H; V=O-mannoside; Y=H; Q=OH.

In another embodiment, A=$C_{14}H_{28}$; Z=NH; W=C(O)CH($CH_2COOH$)$_2$; X=H; $R^1$H; R=H; V=O-mannoside; Y=H; Q=OH.

In another embodiment, A=$C_{14}H_{28}$; Z=NH; W=C(O)N($CH_2COOH$)$_2$; X=H; $R^1$H; R=H; V=O-mannoside; Y=H; Q=OH.

In another embodiment, A=$C_{14}H_{28}$; Z=NH; W=C(O)$CH_2CH_2COOH$); X=H; $R^1$palmitoyl; R=H; V=O-mannoside; Y=H; Q=OH.

In another embodiment, A=$C_{14}H_{28}$; Z=NH; W=C(O)CH($CH_2COOH$)$_2$; X=H; $R^1$=palmitoyl; R=H; V=O-mannoside; Y=H; Q=OH.

In another embodiment, $A=C_{14}H_{28}$; $Z=NH$; $W=C(O)N(CH_2COOH)_2$; $X=H$; $R^1=$palmitoyl; $R=H$; $V=O$-mannoside; $Y=H$; $Q=OH$.

In another embodiment, $A=C_{14}H_{28}$; $Z=O$; $W=C(O)CH_2CH_2COOH)$; $X=H$; $R^1=$octanoyl; $R=H$; $V=OH$; $Y=H$; $Q=O$-mannoside.

In another embodiment, $A=C_{14}H_{28}$; $Z=O$; $W=C(O)CH(CH_2COOH)$; $X=H$; $R^1=$octanoyl; $R=H$; $V=OH$; $Y=H$; $Q=O$-mannoside.

In another embodiment, $A=C_{14}H_{28}$; $Z=O$; $W=C(O)N(CH_2COOH)_2$; $X=H$; $R^1=$octanoyl; $R=H$; $V=OH$; $Y=H$; $Q=O$-mannoside.

In another embodiment, $A=C_{14}H_{28}$; $Z=O$; $W=C(O)CH_2CH_2COOH)$; $X=H$; $R^1=H$; $R=H$; $V=OH$; $Y=H$; $Q=O$-mannoside.

In another embodiment, $A=C_{14}H_{28}$; $Z=O$; $W=C(O)CH_2COOH)_2$; $X=H$; $R^1H$; $R=H$; $V=OH$; $Y=H$; $Q=O$-mannoside.

In another embodiment, $A=C_{14}H_{28}$; $Z=O$; $W=C(O)N(CH_2COOH)_2$; $X=H$; $R^1H$; $R=H$; $V=OH$; $Y=H$; $Q=O$-mannoside.

In another embodiment, $A=C_{14}H_{28}$; $Z=O$; $W=C(O)CH_2CH_2COOH)$; $X=H$; $R^1=$palmitoyl; $R=H$; $V=OH$; $Y=H$; $Q=O$-mannoside.

In another embodiment, $A=C_{14}H_{28}$; $Z=O$; $W=C(O)CH(CH_2COOH)$; $X=H$; $R^1=$palmitoyl; $R=H$; $V=OH$; $Y=H$; $Q=O$-mannoside.

In another embodiment, $A=C_{14}H_{28}$; $Z=O$; $W=C(O)N(CH_2COOH)_2$; $X=H$; $R^1$palmitoyl; $R=H$; $V=OH$; $Y=H$; $Q=O$-mannoside.

In another embodiment, $A=C_{14}H_{28}$; $Z=NH$; $W=C(O)CH_2CH_2COOH)$; $X=H$; $R^1$octanoyl; $R=H$; $V=OH$; $Y=H$; $Q=O$-mannoside.

In another embodiment, $A=C_{14}H_{28}$; $Z=NH$; $W=C(O)CH(CH_2COOH)_2$; $X=H$; $R^1$octanoyl; $R=H$; $V=OH$; $Y=H$; $Q=O$-mannoside.

In another embodiment, $A=C_{14}H_{28}$; $Z=NH$; $W=C(O)N(CH_2COOH)_2$; $X=H$; $R^1=$octanoyl; $R=H$; $V=OH$; $Y=H$; $Q=O$-mannoside.

In another embodiment, $A=C_{14}H_{28}$; $Z=NH$; $W=C(O)(CH_2CH_2COOH)$; $X=H$; $R^1=H$; $R=H$; $V=OH$; $Y=H$; $Q=O$-mannoside.

In another embodiment, $A=C_{14}H_{28}$; $Z=NH$; $W=C(O)CH(CH_2COOH)$; $X=H$; $R^1=H$; $R=H$; $V=OH$; $Y=H$; $Q=O$-mannoside.

In another embodiment, $A=C_{14}H_{28}$; $Z=NH$; $W=C(O)N(CH_2COOH)_2$; $X=H$; $R^1=H$; $R=H$; $V=OH$; $Y=H$; $Q=O$-mannoside.

In another embodiment, $A=C_{14}H_{28}$; $Z=NH$; $W=C(O)CH_2CH_2COOH)$; $X=H$; $R^1=$palmitoyl; $R=H$; $V=OH$; $Y=H$; $Q=O$-mannoside.

In another embodiment, $A=C_{14}H_{28}$; $Z=NH$; $W=C(O)CH(CH_2COOH)_2$; $X=H$; $R^1=$palmitoyl; $R=H$; $V=OH$; $Y=H$; $Q=O$-mannoside.

In another embodiment, $A=C_{14}H_{28}$; $Z=NH$; $W=C(O)N(CH_2COOH)_2$; $X=H$; $R^1$palmitoyl; $R=H$; $V=OH$; $Y=H$; $Q=O$-mannoside.

In another embodiment, $A=C_{14}H_{28}$; $Z=O$; $W=C(O)CH_2CH_2COOH$; $X=H$; $R^1$octanoyl; $R=H$; $V=O$-cellobioside; $Y=H$; $Q=OH$.

In another embodiment; $A=C_{14}H_{28}$; $Z=O$; $W=C(O)CH(CH_2COOH)_2$; $X=H$; $R^1=$octanoyl; $R=H$; $V=O$-cellobioside; $Y=H$; $Q=OH$.

In another embodiment, $A=C_{14}H_{28}$; $Z=O$; $W=C(O)N(CH_2COOH)_2$; $X=H$; $R^1=$octanoyl; $R=H$; $V=O$-O-cellobioside; $Y=H$; $Q=OH$.

In another embodiment, $A=C_{14}H_{28}$; $Z=O$; $W=C(O)CH_2CH_2COOH)$; $X=H$; $R^1=H$; $R=H$; $V=O$-cellobioside; $Y=H$; $Q=OH$.

In another embodiment, $A=C_{14}H_{28}$; $Z=O$; $W=C(O)CH(CH_2COOH)_2$; $X=H$; $R^1H$; $R=H$; $V=O$-cellobioside; $Y=H$; $Q=OH$.

In another embodiment, $A=C_{14}H_{28}$; $Z=O$; $W=C(O)N(CH_2COOH)_2$; $X=H$; $R^1H$; $R=H$; $V=O$-cellobioside; $Y=H$; $Q=OH$.

In another embodiment, $A=C_{14}H_{28}$; $Z=O$; $W=C(O)CH_2CH_2COOH)$; $X=H$; $R^1=$palmitoyl; $R=H$; $V=O$-cellobioside; $Y=H$; $Q=OH$.

In another embodiment, $A=C_{14}H_{28}$; $Z=O$; $W=C(O)CH(CH_2COOH)_2$; $X=H$; $R^1=$palmitoyl; $R=H$; $V=O$-cellobioside; $Y=H$; $Q=OH$.

In another embodiment, $A=C_{14}H_{28}$; $Z=O$; $W=C(O)N(CH_2COOH)_2$; $X=H$; $R^1=$palmitoyl; $R=H$; $V=O$-cellobioside; $Y=H$; $Q=OH$.

In another embodiment, $A=C_{14}H_{28}$; $Z=NH$; $W=C(O)CH_2CH_2COOH)$; $X=H$; $R^1=$octanoyl; $R=H$; $V=O$-cellobioside; $Y=H$; $Q=OH$.

In another embodiment, $A=C_{14}H_{28}$; $Z=NH$; $W=C(O)CH(CH_2COOH)_2$; $X=H$; $R^1=$octanoyl; $R=H$; $V=O$-cellobioside; $Y=H$; $Q=OH$.

In another embodiment, $A=C_{14}H_{28}$; $Z=NH$; $W=C(O)N(CH_2COOH)_2$; $X=H$; $R^1=$octanoyl; $R=H$; $V=O$-cellobioside; $Y=H$; $Q=OH$.

In another embodiment, $A=C_{14}H_{28}$; $Z=NH$; $W=C(O)CH_2CH_2COOH)$; $X=H$; $R^1H$; $R=H$; $V=O$-cellobioside; $Y=H$; $Q=OH$.

In another embodiment, $A=C_{14}H_{28}$; $Z=NH$; $W=C(O)H(CH_2COOH)_2$; $X=H$; $R^1H$; $R=H$; $V=O$-cellobioside; $Y=H$; $Q=OH$.

In another embodiment; $A=C_{14}H_{28}$; $Z=NH$; $W=C(O)N(CH_2COOH)_2$; $X=H$; $R^1=H$; $R=H$; $V=O$-cellobioside; $Y=H$; $Q=OH$.

In another embodiment, $A=C_{14}H_{28}$; $Z=NH$; $W=C(O)CH_2CH_2COOH)$; $X=H$; $R^1=$palmitoyl; $R=H$; $V=O$-cellobioside; $Y=H$; $Q=OH$.

In another embodiment, $A=C_{14}H_{28}$; $Z=NH$; $W=C(O)CH(CH_2COOH)_2$; $X=H$; $R^1$palmitoyl; $R=H$; $V=O$-cellobioside; $Y=H$; $Q=OH$.

In another embodiment, $A=C_{14}H_{28}$; $Z=NH$; $W=C(O)N(CH_2COOH)_2$; $X=H$; $R^1$palmitoyl; $R=H$; $V=O$-cellobioside; $Y=H$; $Q=OH$.

In another embodiment, $A=C_{14}H_{28}$; $Z=O$; $W=C(O)CH_2CH_2COOH)$; $X=H$; $R^1$octanoyl; $R=H$; $V=OH$; $Y=H$; $Q=O$-cellobioside.

In another embodiment, $A=C_{14}H_{28}$; $Z=O$; $W=C(O)CH(CH_2COOH)_2$; $X=H$; $R^1=$octanoyl; $R=H$; $V=OH$; $Y=H$; $Q=O$-cellobioside.

In another embodiment, $A=C_{14}H_{28}$; $Z=O$; $W=C(O)N(CH_2COOH)_2$; $X=H$; $R^1=$octanoyl; $R=H$; $V=OH$; $Y=H$; $Q=O$-cellobioside.

In another embodiment, $A=C_{14}H_{28}$; $Z=O$; $W=C(O)CH_2CH_2COOH)$; $X=H$; $R^1=H$; $R=H$; $V=OH$; $Y=H$; $Q=O$-cellobioside.

In another embodiment, $A=C_{14}H_{28}$; $Z=O$; $W=C(O)CH(CH_2COOH)_2$; $X=H$; $R^1=H$; $R=H$; $V=OH$; $Y=H$; $Q=O$-cellobioside.

In another embodiment, $A=C_{14}H_{28}$; $Z=O$; $W=C(O)N(CH_2COOH)_2$; $X=H$; $R^1=H$; $R=H$; $V=OH$; $Y=H$; $Q=O$-cellobioside.

In another embodiment, $A=C_{14}H_{28}$; $Z=O$; $W=C(O)CH_2CH_2COOH$; $X=H$; $R^1=$palmitoyl; $R=H$; $V=OH$; $Y=H$; $Q=O$-cellobioside.

In another embodiment, $A=C_{14}H_{28}$; $Z=O$; $W=C(O)CH(CH_2COOH)_2$; $X=H$; $R^1=$palmitoyl; $R=H$; $V=OH$; $Y=H$; $Q=O$-cellobioside.

In another embodiment, $A=C_{14}H_{28}$; $Z=O$; $W=C(O)N(CH_2COOH)_2$; $X=H$; $R^1=$palmitoyl; $R=H$; $V=OH$; $Y=H$; $Q=O$-cellobioside.

In another embodiment, A=$C_{14}H_{28}$; Z=NH; W=C(O)$CH_2CH_2COOH$; X=H; $R^1$=octanoyl; R=H; V=OH; Y=H; Q=O-cellobioside.

In another embodiment, A=$C_{14}H_{28}$; Z=NH; W=C(O)CH($CH_2COOH)_2$; X=H; $R^1$=octanoyl; R=H; V=OH; Y=H; Q=O-cellobioside.

In another embodiment, A=$C_{14}H_{28}$; Z=NH; W=C(O)N($CH_2COOH)_2$; X=H; $R^1$=octanoyl; R=H; V=OH; Y=H; Q=O-cellobioside.

In another embodiment, A=$C_{14}H_{28}$; Z=NH; W=C(O)$CH_2CH_2COOH$; X=H; $R^1$=H; R=H; V=OH; Y=H; Q=O-cellobioside.

In another embodiment, A=$C_{14}H_{28}$; Z=NH; W=C(O)CH($CH_2COOH)_2$; X=H; $R^1$=H; R=H; V=OH; Y=H; Q=O-cellobioside.

In another embodiment, A=$C_{14}H_{28}$; Z=NH; W=C(O)N($CH_2COOH)_2$; X=H; $R^1$=H; R=H; V=OH; Y=H; Q=O-cellobioside.

In another embodiment, A=$C_{14}H_{28}$; Z=NH; W=C(O)$CH_2CH_2COOH$; X=H; $R^1$=palmitoyl; R=H; V=OH; Y=H; Q=O-cellobioside.

In another embodiment, A=$C_{14}H_{28}$; Z=NH; W=C(O)CH($CH_2COOH)_2$; X=H; $R^1$=palmitoyl; R=H; V=OH; Y=H; Q=O-cellobioside.

In another embodiment, A=$C_{14}H_{28}$; Z=NH; W=C(O)N($CH_2COOH)_2$; X=H; $R^1$=palmitoyl; R=H; V=OH; Y=H; Q=O-cellobioside.

In another embodiment, the compound is 1-deoxy-5-hydroxy-sphinganine, wherein at least one $R^2$ is covalently bound to either hydroxyl group or the amino function of the molecule.

Specific examples of suitable compounds for use according to the present invention include, but are not limited to:

Ceramide β-glucuronide; sphinganine β-glucuronide; dihydroceramide β-glucuronide; sphingomyelin β-glucuronide; sphingosine β-glucuronide; ceramide b-D-galactoside; sphinganine b-D-galactoside dihydroceramide b-D-galactoside; sphingomyelin b-D-galactoside; sphingosine b-D-galactoside; ceramide N-acetyl-b-D-glucosamine; sphingomyelin N-acetyl-b-D-glucosamine; dihydroceramide N-acetyl-b-D-glucosamine; sphingomyelin N-acetyl-b-D-glucosamine; sphingosine N-acetyl-b-D-glucosamine; ceramide a-D-mannoside; sphinganine a-D-mannoside; dihydroceramide a-D-mannoside; sphingomyelin a-D-mannoside; sphingosine a-D-mannoside; ceramide b-D-cellobioside; sphinganine b-D-cellobioside; dihydroceramide b-D-cellobioside; sphingomyelin b-D-cellobioside; ceramide b-D-glucopyranosides; sphinganine b-D-glucopyranosides; dihydroceramide b-D-glucopyranosides, sphingomyelin b-D-glucopyranosides; sphingosine b-D-glucopyranosides; ceramide b-D-galactopyranosides; sphinganine b-D-galactopyranosides; dihydroceramide b-D-galactopyranosides; sphingomyelin b-D-galactopyranosides; and sphingosine b-D-galactopyranosides.

Prodrug Activity

As discussed in the Background of the Invention, one problem associated with the administration of sphingolipids as therapeutic agents is that they can be metabolized before they reach the target location. This can be a particular problem if the target location is distant from the site of administration. For example, perhaps only 5–10% of a sphingolipid reaches the lower intestine in the delivered form. Since sphingolipids of milk origin have been determined to have a therapeutic effect on intestinal tumors, the low bioavailability to that region is troublesome.

This problem has been addressed by providing a sphingolipid, or an analog or physiological derivative thereof, alone or in combination, as a prodrug that includes an $R^2$ substituent, including those of Formula I, that is cleaved by an appropriate enzyme in vivo to release a parent sphingolipid moiety for desired therapy. Certain derivatives of Formula I are especially suited for treatment of disorders of the lower intestinal tract, including but not limited to colon cancer, intestinal polyps, intestinal tumors, inflammatory bowel diseases including ulcerative colitis and Crohn's disease, necrotizing enterocolitis, ileocecitis, other inflammations of the lower bowel, and antibiotic associated colitis, as the enzymes which free the sphingolipid from its prodrug form are concentrated in the lower intestine. These prodrugs are resistant to hydrolysis in the upper gastrointestinal tract, and are more readily cleaved in the cecum and the colon. It is not necessary that the compound undergo no metabolism in the upper GI tract, rather, that a sufficient portion survive and be cleaved in the colon. It should also be noted that this same approach can apply to the delivery of prodrug sphingolipids or analogs or physiological derivatives thereof via other routes, including blood circulation.

For example, it has been discovered that the glucuronide of the compounds of Formula I are cleaved by the colonic beta-glucuronidase(s). Phosphodiesterases can cleave the disclosed phosphosphingolipids. Sphingomyelinase can act on sphingomyelin derivatives, as well as ceramide phosphoinositols. The b-D-galactoside derivatives of Formula I can be cleaved by b-D-galactosidase. N-acetyl-b-D-glucosamine derivatives can be acted on by N-acetyl-b-D-glucosaminidase. The a-D-mannoside derivatives of Formula I are substrates for a-D-mannosidase. The organic azo-bond containing moiety can be reduced by an azoreductase. The b-D-cellobiosides, b-D-glucopyranosides, b-D-galactopyranosides, and b-D-glucuronides are substrates for glycosylhydrolases. Multiple enzymes from colonic bacteria are able to digest starch (such as maize starch, amylo-maize starch, pectin and others found in wheat flour, potato and beans). Multiple enzymes of colonic bacteria are also capable of cleaving lactose, raffinose, stachyose, and fructooligosaccharide (such as oligofructose and insulin) derivatives of Formula I. Compounds of Formula I which are amides and esters of b-cyclodextrin or dextrans linked via succinate and glutarate are substrates for amidases and esterases. Derivatives of compounds of Formula I which are poly(L-aspartic acid) and other amino acids and peptides are substrates for peptidases and esterases.

The active compound which is a substrate for the colonic enzyme can be administered by any suitable means, including orally. In one embodiment, the active compound is administered in a way that promotes the intestinal microflora that produce the enzymes that cleave these pro-drugs. In one embodiment, the active compound (such as the β-glucuronide of ceramide) contains a group that is poorly cleaved by enzymes in the upper intestine, but will be acted upon by enzymes produced by microorganisms in the colon.

In another embodiment, the active compound can be co-administered with another sphingolipid analog (such as a fumonisin) that alters the metabolism of the active compound to promote better delivery to the target tissue and/or a longer tissue lifetime.

In another embodiment, a method is provided for the delivery of a biologically active molecule to a specific site, for example, a plasma membrane surface or a nucleus of a particular cell type. In this embodiment, a biologically active molecule is linked to a second "targeting molecule" either directly or through a linking moiety, including, but not limited to A. In a preferred embodiment, the targeting molecule is a moiety that binds to a receptor molecule on the target membrane's surface.

As an example, steroids can be used to deliver chemotherapy to a variety of pathogenic cells. Examples include estrogens or testosterone (for malignant breast and prostate tumors), sex hormones (responsive sebaceous and pilosebaceous units); and corticosteroids (lymphocytes, antigen presenting cells and other immune cells, etc.).

Antibodies and antibody fragments conjugated to sphingolipid metabolism altering compounds The term "antibody," as used herein, includes monoclonal and polyclonal antibodies as well as antibody fragments which bind specifically but reversibly to a desired epitope on a target abnormally proliferating cell. It is preferred that the monoclonal antibody or monoclonal antibody fragment is derived from a monoclonal antibody or antibody fragment. Preparation of monoclonal and polyclonal antibodies to an antigen can be achieved using any known method, and for example, those described in Zola, H., "*Monoclonal Antibodies—A manual of techniques*" CRC Press (1988), and Antibodies: A Laboratory Manual, Harlow & Lane; Cold Spring Harbor (1988), incorporated herein by reference.

In one embodiment, primarily for laboratory use, animals are immunized with the antigen, and preferably an adjuvant. Booster immunizations are optionally continued with antigen in PBS and mixed with adjuvant at periodic intervals. The animals are then bled following the immunizations. After removal of clot and debris, the serum can be assayed by ELISA (enzyme-linked immunosorbent assay). Monthly, or other periodic titers can be obtained after initial immunization.

Alternatively, spleens are harvested from animals immunized with the antigen, and preferably an adjuvant. Spleen cells are separated and fused with immortal myeloma cells using polyethylene glycol. The fused hybridoma cells are selected and cultured in vitro. The hybridoma cell culture fluids are tested for the presence of hybridoma antibodies having the desired specificity. The selection technique for identifying the appropriate monoclonal or polyclonal antibody is an important aspect in obtaining desired immunospecificity. The hybridoma cells can be tested for the presence of antibodies specific for the antigen, for example, with an ELISA conducted by standard methods.

The variable heavy ($V_H$) and variable light ($V_L$) domains of the antibody are involved in antigen recognition, a fact first recognized by early protease digestion experiments. Further confirmation was found by "humanization" of rodent antibodies. Variable domains of rodent origin can be fused to constant domains of human origin such that the resultant antibody retains the antigenic specificity of the rodent parented antibody (Morrison et al., *Proc. Nat. Acad. Sci. USA*, 81:6851–6855, 1984). "CRD grafting" can be used to humanize rodent antibodies. Additionally or alternatively, recombinant monoclonal antibodies may be "primatized," i.e. antibodies formed in which the variable regions are derived from two different primate species, preferably the variable regions of the antibody from the macaque monkey, and the constant regions from human. The advantages of such antibodies include high homology to human immunoglobulin, presence of human effector functions, reduced immunogenicity and longer serum half-life (Newman et al. *Biotechnology*, 10:1455, 1992).

The region specific for the antigen can be expressed as part of a bacteriophage, for example, using the technique of McCafferty et al. *Nature,* 348:552–554, 1990. Antibody-like molecules of the invention can be selected from phage display libraries using the methods described in Griffiths et al. *EMBO J.,* 12:725–734, 1993, in which the antigens are immobilized and used to select phages. Also, appropriate cells grown in monolayers and either fixed with formaldehyde or glutaraldehyde or unfixed can be used to bind phages. Irrelevant phages are washed away and bound phages recovered by disrupting their binding to the antigen and reamplifying in bacteria. This selection and amplification process is done several times to enrich the phage population for those molecules which are the antibody-like molecules of the invention.

Antibody fragments include Fab-like molecules (Better et al. *Science* 240:1041, 1988); Fv molecules (Skerra et al., *Science,* 240:1038 1988); single-chain Fv (ScFv) molecules where the $V_H$ and $V_L$ partner domains are linked via a flexible oligopeptide (Bird et al., *Science.* 242:423, 1988) Huston et al., *Proc. Natl. Acad. Sci. USA.* 85:5879 1988) and single domain antibodies (dAbs) comprising isolated V domains (Ward et al., *Nature.* 341:544 1989). A general review of the techniques involved in the synthesis of antibody fragments which retain their specific binding sites is found in Winter and Milstein, *Nature,* 349:293–299, 1991.

Antibody fragments, including but not limited to Fab, $(Fab)_2$, Fv, scFv and dAb fragments are included in this invention. Antibody-like molecules can be prepared using the recombinant DNA techniques of WO 84/03712, the disclosure of which is herein incorporated by reference.

There can be advantages to using antibody fragments, rather than whole antibodies. Fab, Fv, ScFv and dAb antibody fragments can all be expressed in and secreted from *E. coli*, thus allowing the facile production of large amounts of the fragments.

Whole antibodies, and $F(ab')_2$ fragments are "bivalent." By "bivalent" it is meant that the antibodies and $F(ab')_2$ fragments have two antigen combining sites. In contrast, Fab, Fv, ScFv and dAb fragments are monovalent, having only one antigen combining site.

The art of "antibody engineering" is advancing rapidly, as is described in Tan L. K. and Morrison, S. L., *Adv. Drug Deliv.,* Rev. 2: 129–142 1988, Williams, G., *Tibtech.* 6: 36–42, 1988, and Neuberger, M. S. et al., 8*th International Biotechnology Symposium Part* 2, 792–799, 1988 (all of which are incorporated herein by reference), and is well suited to preparing antibody-like molecules derived from the antibodies of the invention.

The antibody can be coupled, i.e., conjugated, to a sphingolipid or a sphingolipid metabolism altering compound. Such conjugates have a "binding portion," which consists of the antibody of the invention, and a "functional portion," which consists of the sphingolipid or sphingolipid metabolism altering compound. The binding portion and the functional portion can be separated by a linking or spacing moiety.

The binding portion and the functional portion of the conjugate (if a peptide or polypeptide containing sphingolipid metabolism altering compound) can be linked together by any of the conventional ways of cross-linking polypeptides, such as those generally described in O'Sullivan et al., *Anal. Biochem.* 100: 100–108, 1979. For example, one portion can be enriched with thiol groups and the other portion reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulfide bonds.

Alternatively, if the binding portion contains carbohydrates, such as would be the case for an antibody or some antibody fragments, the functional portion can be linked via the carbohydrate portion using the linking technology in EP 0 088 695.

In an alternative embodiment, the functional portion of the conjugate can be or include an enzyme for converting a prodrug into a drug, using technology similar to that described by Bagshawe and his colleagues (Bagshawe, Br. J. Cancer. 56: 531, 1987; Bagshawe et al., Br. J. Cancer. 58: 700, 1988; WO 88/07378). It may not be necessary for the whole enzyme to be present in the conjugate but, of course, the catalytic portion must be present. So-called "abzymes" can be used, in which a monoclonal antibody is raised to a compound involved in the reaction one wishes to catalyze, usually the reactive intermediate state. The resulting antibody can then function as an enzyme for the reaction. Non-limiting examples of enzymes that can be used in this manner include beta-glucuronidase(s), phosphodiesterases, sphingomyelinase, b-D-galactosidase, N-acetyl-b-D-glucosaminidase, α-D-mannosidase, azoreductase, glycosylhydrolases, amidases, peptidases, and esterases.

The conjugate can be purified by size exclusion or affinity chromatography, and tested for dual biological activities. The antigen immunoreactivity can be measured using an enzyme-linked immunosorbent assay (ELISA) with immobilized antigen and in a live cell radio-immunoassay. An enzyme assay can be used for β-glucosidase using a substrate which changes in absorbance when the glucose residues are hydrolyzed, such as o-NPG (o-nitrophenyl-β-D-glucopyranoside), liberating 2-nitrophenol which is measured spectrophotometrically at 405 nm.

Stability of the conjugate can be tested in vitro initially by incubating at 37° C. in serum, followed by size exclusion HPLC analysis. Stability in vivo can be tested in the same way in mice by analyzing the serum at various times after injection of the conjugate. In addition, it is possible to radiolabel the antibody with $^{125}$I, and the enzyme with $^{125}$I before conjugation, and to determine the biodistribution of the conjugate, free antibody and free enzyme in mice.

Alternatively, the conjugate can be produced as a fusion compound by recombinant DNA techniques whereby a length of DNA comprises respective regions encoding the two portions of the conjugate either adjacent to one another or separated by a region encoding a linker peptide which does not destroy the desired properties of the conjugate. Conceivably, the two functional portions of the compound can overlap wholly or partly. The DNA is then expressed in a suitable host in known ways.

The antibody conjugates can be administered in any suitable way, usually parenterally, for example intravenously or intra peritoneally, in standard sterile, non-pyrogenic formulations of diluents and carriers, for example isotonic saline (when administered intraveneously). Once the conjugate has bound to the target cells and been cleared from the bloodstream (if necessary), which typically takes a day or so, if the conjugate is an antibody/enzyme or abzyme conjugate, the sphingolipid prodrug can be administered, usually as a single infused dose. If needed, because the conjugate can be immunogenic, cyclosporin or some other immunosuppressant can be administered to provide a longer period for treatment but usually this will not be necessary.

II. ALTERATION OF SPHINGOSINE METABOLISM AND PATHWAYS

The present invention includes a method of altering the metabolism of sphingolipids in a cell comprising contacting the cell with a metabolism altering amount of a compound of the Formula I, or a pharmaceutically acceptable salt thereof, or with a fumonisin derivative to which is covalently bound, either directly or indirectly, an $R^2$ group, collectively referred to as "sphingosine metabolic altering compounds."

As discussed in the Background of the Invention, sphingolipids mediate a number of fundamental pathways in vivo. The sphingolipid metabolic altering compounds can be used to alter these pathways. One can determine without undue experimentation which of these pathways are affected by carrying out simple assays such as those set out below.

The ability of the analog to alter sphingolipid metabolism can be established by assay of elevations in the pertinent upstream metabolite as described for fumonisins, for example, in U.S. Pat. Nos. 5,232,837 and 5,518,879. Where cellular responsiveness is unknown, this can be ascertained by analysis of the pertinent cells in culture.

In one embodiment, the compounds inhibit "ceramide synthase," which is an enzyme or enzymes which add in N-acyl linkage to sphingosine, sphinganine and other long-chain bases. Thus, both sphinganine N-acyltransferase, which catalyzes in the conversion of sphinganine to dihydroceramide, and sphingosine N-acyltransferase, which catalyzes the conversion of sphingosine to ceramide, are referred to as ceramide synthase herein. As also used herein, "analog of dihydroceramide or ceramide" means a compound which can be catalyzed by a fumonisin or an analog. In another embodiment, the catabolism of sphingosine and other bioactive "sphingoid bases" can be blocked by administration of an inhibitor of sphingosine kinase, the other enzyme(s) that metabolize these compounds.

"Altering the metabolism" as used herein means either an increase or a decrease in the concentration of the metabolites of both the sphingolipid biosynthetic and catabolic pathways. Typically, since ceramide synthase (sphinganine-N-acyltransferase) is generally bound by the sphingolipid metabolism altering compound, including a fumonisin or fumonisin analog, and ceramide synthase (sphinganine-N-acyltransferase), which can also be bound by these compounds, catalyzes the conversion of sphinganine to dihydroceramide in the pathway, the concentration of any compound above the site of action can be increased and the concentration of any compound below the site of action can be decreased using the fumonisin or fumonisin analog. However, the amounts of various compounds of the pathway can depend on the time period after inhibition or their relationship to other related pathways. For example, a fumonisin can bind sphingosine-N-acyltransferase, which would increase the amount of sphingosine by preventing the conversion back to ceramide and a fumonisin can also bind ceramide synthase (sphinganine-N-acyltransferase), which would decrease the amount of sphingosine by decreasing the amount of ceramide which can be converted to sphingosine. Thus, the fumonisin can cause both the increase and/or decrease of sphingosine, depending on which pathway is dominant. Such increases or decreases at various times after fumonisin ingestion can be routinely determined by standard methods.

"Metabolism altering amount" as used herein means a quantity of a sphingolipid metabolism altering compound capable of effecting a change in the sphingolipid metabolism in cells. This amount can vary depending on the environment in which the cells are contained. For in vivo administration, the precise quantity of the compound to elicit the desired effect can be determined by standard administration and monitoring until optimal dosage is determined. Such amounts can vary from subject to subject depending on size and condition of the subject.

As discussed above, the invention also provides a method for treating an abnormal condition in a subject associated with an alteration in sphingolipid metabolism. This method comprises administering a sphingolipid metabolism altering compound, or an analog thereof, to the subject in a metabolism altering amount. The subject can be a human or a non-human animal and the abnormal condition can be caused by numerous disorders in sphingolipid metabolism. For example, the condition can be an access of sphingosine resulting in Neimann-Picks syndrome, Tay-Sachs disease, a neoplastic condition or toxicity. In a given condition, the effect of the sphingolipid metabolism altering compound may be complex. For example, in a neoplastic condition, the sphingolipid metabolism altering compound can, due to its structural similarity to sphingosine, prevent the formation of a sphingolipid required for growth of the cells and can also act as an inducer of differentiation and thus treat the neoplastic condition.

III. TREATMENT OF ABNORMAL CELL PROLIFERATION

The sphingolipid metabolism altering compound can be administered specifically to treat abnormal cell proliferation, and in particular, cell hyperproliferation. Examples of abnormal cell proliferation include, but are not limited to:

benign tumors, including, but not limited to papilloma, adenoma, firoma, chondroma, osteoma, lipoma, hemangioma, lymphangioma, leiomyoma, rhabdomyoma, meningioma, neuroma, ganglioneuroma, nevus, pheochromocytoma, neurilemona, fibroadenoma, teratoma, hydatidiform mole, granuosa-theca, Brenner tumor, arrhenoblastoma, hilar cell tumor, sex cord mesenchyme, interstitial cell tumor, and thyoma as well as proliferation of smooth muscle cells in the course of development of plaques in vascular tissue;

malignant tumors (cancer), including but not limited to carcinoma, including renal cell carcinoma, prostatic adenocarcinoma, bladder carcinoma, and adenocarcinoma, fibrosarcoma, chondrosarcoma, osteosarcoma, liposarcoma, hemangiosarcoma, lymphangiosarcoma, leiomyosarcoma, rhabdomyosarcoma, myelocytic leukemia, erythroleukemia, multiple myeloma, glioma, meningeal sarcoma, thyoma, cystosarcoma phyllodes, nephroblastoma, teratoma choriocarcinoma, cutaneous T-cell lymphoma (CTCL), cutaneous tumors primary to the skin (for example, basal cell carcinoma, squamous cell carcinoma, melanoma, and Bowen's disease), breast and other tumors infiltrating the skin, Kaposi's sarcoma, and premalignant and malignant diseases of mucosal tissues, including oral, bladder, and rectal diseases;

preneoplastic lesions, mycosis fungoides, psoriasis, dermatomyositis, rheumatoid arthritis, viruses (for example, warts, herpes simplex, and condyloma acuminata), molluscum contagiosum, premalignant and malignant disease of the female genital tract (cervix, vagina, and vulva). The compounds can also be used to induce abortion.

In this embodiment, the sphingolipid metabolism altering compound, or its pharmaceutically acceptable salt, is administered in an effective treatment amount to decrease the hyperproliferation of the target cells. The sphingolipid metabolism altering compound can be modified to include a targeting moiety that concentrates the compound at the active site. Targeting moieties can include an antibody or antibody fragment that binds to a protein on the surface of the target cell, including but not limited to epidermal growth factor receptor (EGFR), c-Esb-2 family of receptors and vascular endothelial growth factor (VEGF).

Combination Therapy

In another embodiment, the compounds, when used as an antiproliferative, can be administered in combination with another compound that increases the effectiveness of the therapy, including but not limited to an antifolate, a 5-fluoropyrimidine (including 5-fluorouracil), a cytidine analogue such as β-L-1,3-dioxolanyl cytidine or β-L-1,3-dioxolanyl 5-fluorocytidine, antimetabolites (including purine antimetabolites, cytarabine, fudarabine, floxuridine, 6-mercaptopurine, methotrexate, and 6-thioguanine), hydroxyurea, mitotic inhibitors (including CPT-11, Etoposide (VP-21), taxol, and vinca alkaloids such as vincristine and vinblastine, an alkylating agent (including but not limited to busulfan, chlorambucil, cyclophosphamide, ifofamide, mechlorethamine, melphalan, and thiotepa), non-classical alkylating agents, platinum containing compounds, bleomycin, an anti-tumor antibiotic, an anthracycline such as doxorubicin and dannomycin, an anthracenedione, topoisomerase II inhibitors, hormonal agents (including but not limited to corticosteroids (dexamethasone, prednisone, and methylprednisone), androgens such as fluoxymesterone and methyltestosterone, estrogens such as diethylstilbesterol, antiestrogens such as tamoxifen, LHRH analogues such as leuprolide, antiandrogens such as flutamide, aminoglutethimide, megestrol acetate, and medroxyprogesterone), asparaginase, carmustine, lomustine, hexamethyl-melamine, dacarbazine, mitotane, streptozocin, cisplatin, carboplatin, levamasole, and leucovorin. Because sphingolipid metabolites participate in the signal transduction pathways for these compounds, and modulation of their amounts with these agents can enhance their effectiveness on the target tissues, the compounds of the present invention can also be used in combination with enzyme therapy agents and immune system modulators such as an interferon, interleukin, tumor necrosis factor, macrophage colony-stimulating factor and colony stimulating factor.

IV. RELEASE OF CYTOCHROME C

Certain sphingoid bases are known to induce the DNA fragmentation and morphologic features of apoptosis in cancer and leukemia cells. Apoptosis is the active and gene-directed form of cell death, with well-characterized biochemical and morphologic features. The biochemical features include the generation of lethal and large-sized of endonucleolytic internucleosomal DNA fragmentation. The morphologic features include cell-shrinkage, chromatin condensation and membrane-bound apoptotic bodies. Apoptosis is triggered by the activation of a family of aspartate-specific cysteine proteases designated as caspases. There is a growing list of substrates that are cleaved and degraded by caspases. Among the caspases, the key caspase that is cleaved and activated early in the molecular cascade is caspase-3 (CPP32β/Yama). Caspase activity results in the degradation of lamina, poly (ADP-ribose) polymerase (PARP), PKCδ, Rb protein, DNA-PK, β-actin, fodrin, gel solution, etc., resulting in the morphologic and biochemical features of apoptosis. Recently, it has been demonstrated that caspase-3 cleavage and activity is initiated by the cytosolic accumulation of cytochrome c (cyt c) released from mitochondria, which is triggered by apoptotic stimuli as a pre-apoptotic event. Therefore, promotion of mitochondrial cyt c triggers, while its blockage inhibits, the cleavage and activity of caspase-3 and apoptosis. The gene-product of the anti-apoptotic Bcl-2 gene is localized to the outer mitochondrial membrane, where it blocks the egress of cyt c from mitochondria, thereby preventing the generation of caspase-3 cleavage and activity and resulting apoptosis.

Down-regulation of Bcl-2 levels tilts the balance and sensitizes cells to undergo apoptosis.

It has now been discovered that the sphingoid bases, including the sphingolipid metabolism altering compounds described herein, trigger the release of cytochrome c from mitochondria into the cytosol, resulting in the cleavage and activity of caspase-3 and apoptosis. In addition, treatment with sphingosine has been shown to down-regulate Bcl-2 levels, which further sensitizes cancer cells to apoptosis induced by other apoptotic stimuli including chemotherapeutic drugs, γ-radiation and Fas ligand. Therefore, treatment with sphingosine may sensitize cancer cells simultaneously by promoting the cytosolic accumulation of cytochrome c and by down-regulating Bcl-2, which acts as a barrier to this event.

Figure 2A:
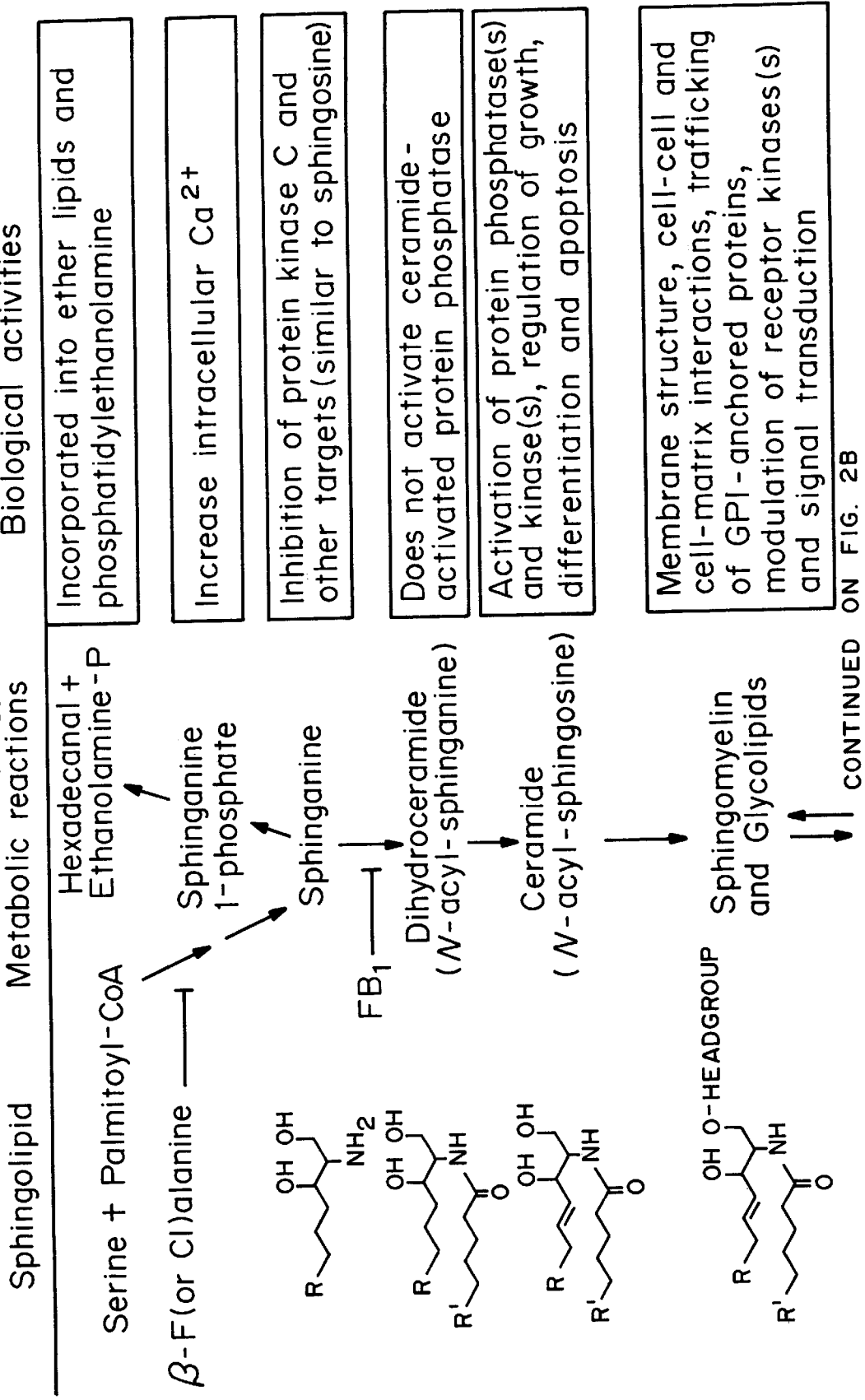
FIG. 2 is an illustration of the structure, metabolic reactions, and biological activities of the representative sphingolipids sphinganine, dihydroceramide, ceramide, sphingomyelin, ceramide, and sphingosine.
Figure 2B:
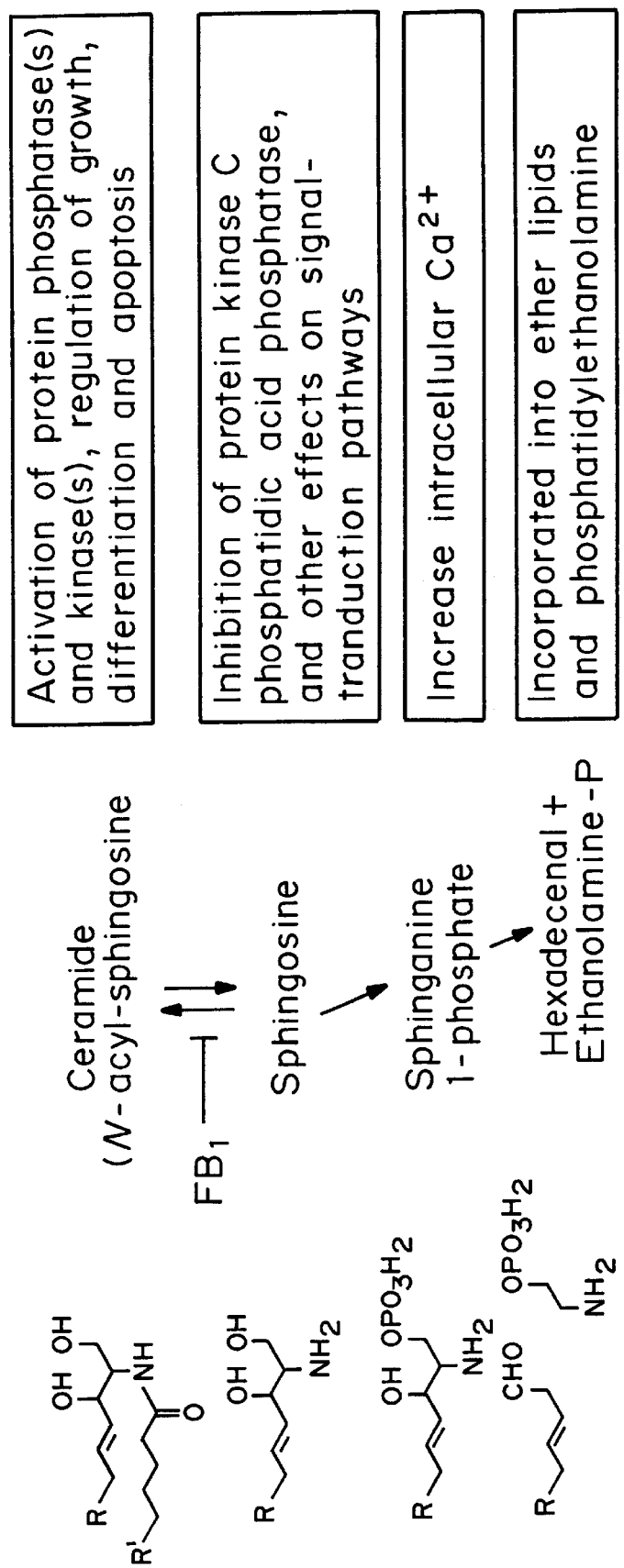
Figure 3B:
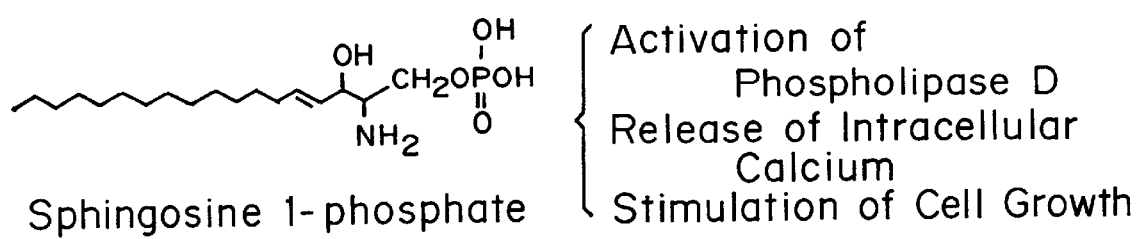
FIG. 3 is an illustration of bioactive sphingolipids, such as ganglioside $G_{M3}$, lactosylceramide, sphingomyelin, ceramide, sphingosine and sphingosine 1-phosphate.
Figure 4:
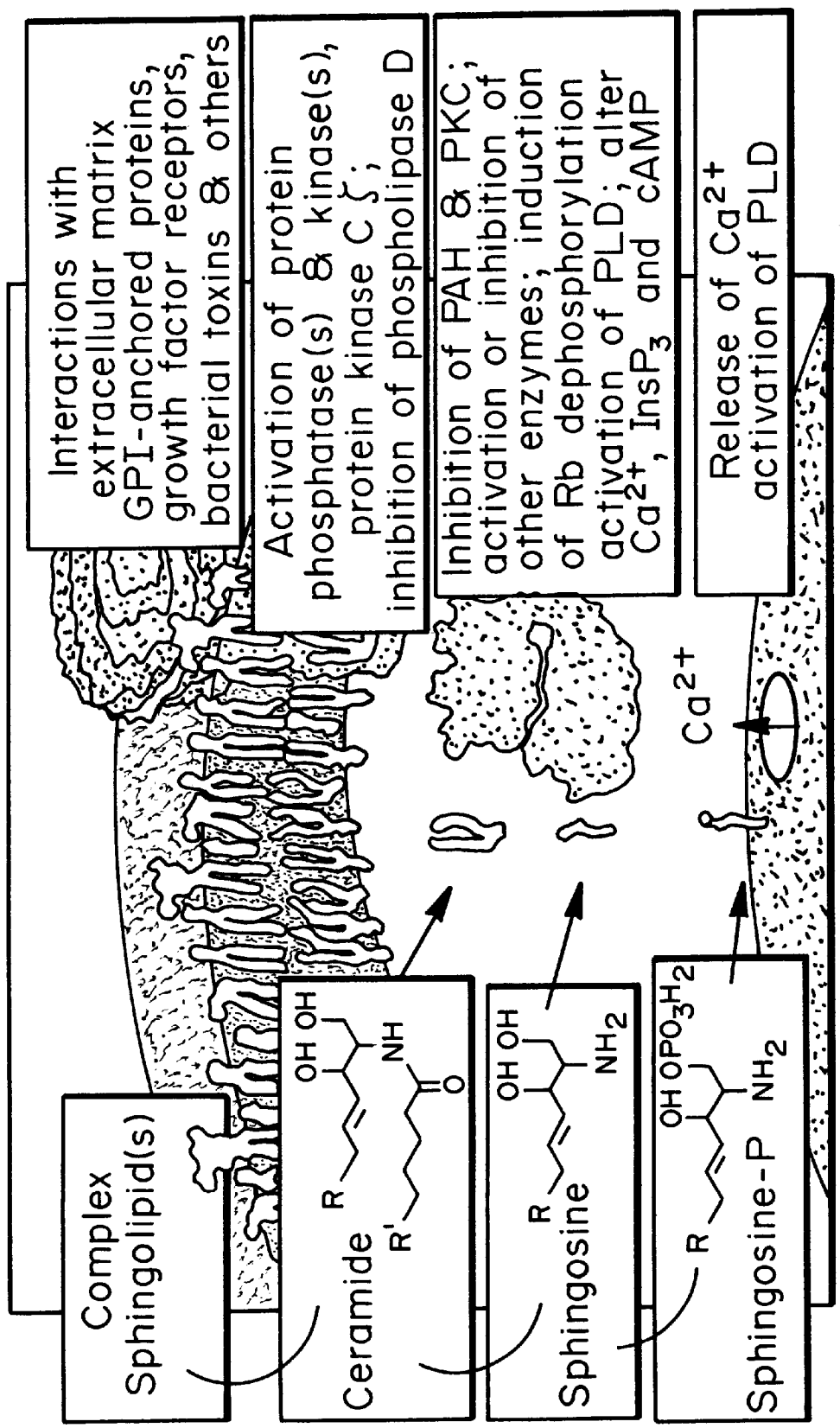
FIG. 4 is an illustration of biological pathways that include sphingolipids.
Figure 5A:
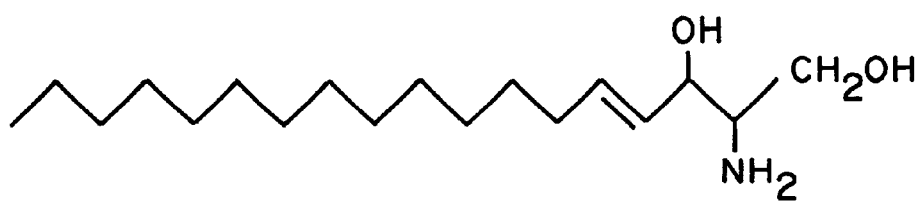
Figure 5A:
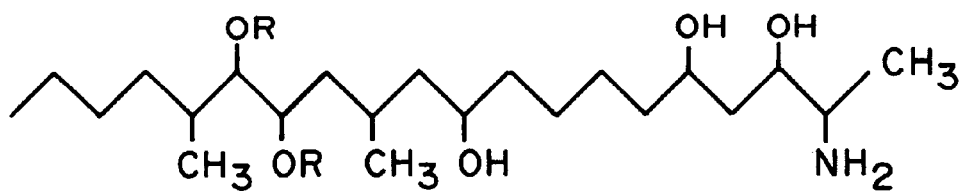
Figure 5A:
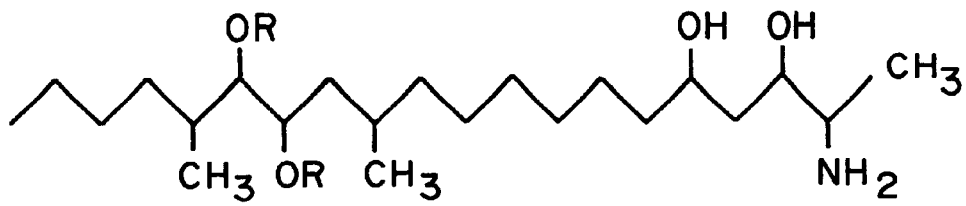
Figure 5A:
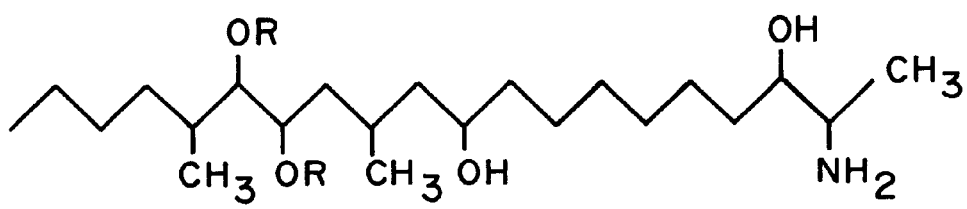

Therefore, the present invention includes a method to trigger the release of cytochrome c that includes administering an effective amount of a sphingolipid (for example those illustrated in FIGS. 1 and 2), or a sphingolipid metabolism altering compound, to a host in need thereof. Cytochrome c accumulation in the cytosol not only mediates apoptosis of cancer cells, but also apoptosis of T-lymphocytes that may be mediating anti-immune diseases or apoptosis of viral infected cells. Therefore, in these cells, cytochrome c accumulation in the cytosol due to sphingolipids such as sphingosine may also result in apoptosis of these cells thereby ameliorating the diseases they cause.

Detailed Background on the Mechanism by which Cytochrome c Triggers Caspase-3 Cleavage and Activity and its Regulation by Bcl-2 Family of Proteins Recent reports have demonstrated that, during taxol-induced apoptosis, caspase-3 is cleaved into subunits with the generation of PARP cleavage activity, and that Bcl-2 activity or Bcl-$x_L$ over expression blocks these events and subsequent apoptosis (Tang, C., et al., *Leukemia,* 8: 1960–1969, 1994; Ibrado, A. M., et al., *Cell Growth & Differ.,* 7:1087–1094, 1996; Ibrado, A. M., et al., *Cancer Res.,* 57: 1109–1115, 1997).

It has been discovered that apoptotic stimuli causes release of cytochrome c from the mitochondrial inner membrane space into the cytosol, where in the presence of dATP, and other cytosolic factors it promotes the cleavage and activity of caspase-3, degradation of a number of substrates and the DNA fragmentation of apoptosis (Liu, X., et al., *Cell,* 86: 147–157, 1996; Yang, J., et al., *Science,* 275: 1129–1132, 1997). In these studies, the loss of mitochondrial cytochrome c due to apoptotic stimuli was noted to precede mitochondrial membrane depolarization and loss of membrane potential ($\Delta\psi m$)(Yang, J., et al., *Science,* 275: 1129–1132, 1997). However, the precise mechanisms by which cytochrome c is released from mitochondria and the cytosolic cleavage of caspase-3 results have not been elucidated. Other reports have suggested that apoptotic stimuli cause mitochondrial permeability transition due to the loss of $\Delta\psi m$ (Zamzami, N., et al., *J. Exp. Med.,* 183: 1533–1544, 1996; Kroemer, G., *J. Exp. Med.,* 182: 367–377, 1995). This results in the release from the mitochondria of a 50 kD protein (not identified, but named AIF-apoptosis inducing factor), which is able to cause chromatin condensation and DNA fragmentation when incubated with nuclei (Kroemer, G., *J. Exp. Med.,* 182: 367–377, 1995; Zamzami, N., et al., *J. Exp. Med.,* 182: 367–377, 1995). However, it is noteworthy that first, cyt c release precedes mitochondrial membrane depolarization; second, cytosolic cyt c participates in activating caspase-3, whereas the 50 kD mitochondrial factor (AIF) directly induces apoptotic changes in the nuclei; and finally, activated caspase-3 induces apoptotic changes in nuclei only in the presence of cytosol, and such changes can be blocked by the presence of sub-micromolar concentrations of the tetrapeptide caspase-3 inhibitor (Yang, J., et al., *Science,* 275: 1129–1132, 1997). In contrast, AIF, once released from mitochondria upon depolarization, functions without cytosol and is insensitive to the caspase-3 inhibitor (Kroemer, G., *J. Exp. Med.,* 182: 367–377, 1995). Despite these differences, it is possible that these two pathways (i.e., cyt c and AIF-mediated) may work together to complete apoptosis. The pre-apoptotic mitochondrial perturbations include a rise in the reactive oxygen species (ROS) as well as the loss of $\Delta\psi m$ (Kim, C. N., et al., *Cancer Res.,* 57: 3115–3120, 1997). Both of these perturbations may be secondary to the mitochondrial loss of cyt c, which is no longer available to donate electrons to cytochrome oxidase (Kim, C. N., et al., *Cancer Res.,* 57: 3115–3120, 1997; Capaldi, R. A., et al., *Ann. Rev. Biochem.,* 59: 569–596, 1990). Consequently, this key Complex IV enzyme of oxidative phosphorylation may be unable to pump protons across inner mitochondrial membrane to preserve $\Delta\psi m$ and completely reduce molecular oxygen to $H_2O$, thereby resulting in the loss of $\Delta\psi m$ and rise of the ROS (Capaldi, R. A., et al., *Ann. Rev. Biochem.,* 59: 569–596, 1990). After accumulation in the cytosol, cyt c promotes the cleavage of caspase-3 in the presence of dATP and two additional apoptotic protease activation factors (APAF-1 and APAF-3) (Liu, X., et al., *Cell,* 86: 147–157, 1996). Therefore, down-regulation of intracellular Bcl-2 levels by sphingosine may abrogate the antiapoptotic activity of a number of proteins that exert their effects through Bcl-2. Also, the lowering of Bcl-2 levels may allow the proapoptotic Bax, Bak and Bcl-$X_S$ to exact their proapoptotic effects more efficiently. Caspase-3 activity has also been shown to cleave and activate a recently cloned DNA fragmentation factor (DFF), which results in the DNA fragmentation of apoptosis (Liu, X., et al., *Cell,* 89: 175, 1997). More recently, the gene encoding the human APAF-1 has been cloned and shown to posses, in its N terminus domains, sequence homology to the ced-4 and ced-3 genes of *c. elegans,* the latter gene being homologous to caspase-3 (Zou, H., *Cell,* in press).

Regulations of Apoptosis by Bcl-2 and Other Bcl-X Family Members

Among the growing list of genes that regulate apoptosis is the Bcl-2 family of genes (Yang, E., et al., *Blood,* 88: 386–401, 1996). The prototype Bcl-2 gene encodes for p26Bcl-2 protein which inhibits apoptosis (Reed, J. C., *Nature,* 387: 773, 1997). Several studies have demonstrated that over expression of Bcl-2 confers resistance against apoptosis due to a variety of chemotherapeutic agents as well as Fas death receptor apoptotic signaling (Tang, C., *Leukemia,* 8: 1960–1969, 1994; Kroemer, G., *Nature Med.,* 3: 614–620, 1997). Bax is a member of the Bcl-2 family (Yang, E., et al., *Blood,* 88: 386–401, 1996). Bax dimerizes with Bcl-2, and the formation of Bax homodimers promotes apoptosis due to death signals (Yin, X. M., et al., *Nature,* 369: 321–323, 1994). Recent reports indicate that selected mutations within the conserved BH1 and BH2 regions of Bcl-2 disrupt its heterodimerization with Bax and abrogate the ability of Bcl-2 to inhibit apoptosis (Yin, X. M., et al., *Nature,* 369: 321–323, 1994; Zha, H., *J. Biol. Chem.,* 271: 7440–7444, 1996). Bax homodimerization and its heterodimerization with Bcl-2 has also been shown to occur via a novel domain (BH3), distinct from BH1 and BH2 (Zha, H., *J. Biol. Chem.,* 271: 7440–7444, 1996). Analogous to a rheostat switch, the balance between free Bax that favors death and Bcl-2/Bax heterodimers that inhibit cell death is critical (Oltvai, Z. N., et al., *Cell,* 79: 189–192, 1994).

Although, Bcl-2/Bax ratio is inherent to the cell, drugs—including taxanes—or other apoptotic stimuli may be able to reset this rheostat (Ibrado, A. M., et al., *Cancer Res.,* 57: 1109–1115, 1997; Oltvai, Z. N., et al., *Cell,* 79: 189–192, 1994). For example, a low ratio of Bcl-2 to Bax, by increasing free Bax, promotes cell death due to taxanes (Oltvai, Z. N., et al., *Cell,* 79: 189–192, 1994; Strobel, T., et al., *Proc. Natl. Acad. Sci. USA,* 93: 14094–14099, 1996). The loss or low levels of Bax have also been correlated with poor response to chemotherapy and shorter survival in women with metastatic breast cancer (Krajewski, S., et al., *Cancer Res.,* 55: 4471–4478, 1995). It is now well-established that the wild-type tumor suppressor gene-product p53$^{wt}$ can induce apoptosis, while mutations or deletion of p53 cause resistance to apoptosis, especially due to DNA-damaging drugs, but not taxol (Oren, M., *Semin. Cancer Biol.,* 5: 221–227, 1994; Lowe, S. W., et al., *Science,* 266: 807–810, 194; Wahl, A. F., et al., *Nature Med.,* 2: 72–79, 1996). Furthermore, p53$^{wt}$ has been demonstrated to transcriptionally up-regulate Bax and decrease Bcl-2, thereby reducing Bcl-2/Bax ratio, and inducing apoptosis (Miyashita, T., et al., *Oncogene,* 9: 1799–1805, 1994; Miyashita, T., *Cell,* 80: 293–299, 1995).

Bcl-x is another member of the Bcl-2 family and shares sequence homology with the conserved BH1 and BH2 regions of the Bcl-2 gene (Boise, L., *Cell,* 74: 597–608, 1993). By alternate mRNA splicing, Bcl-x encodes for two important protein isoforms of which the longer p28Bcl-$x_L$ inhibits apoptosis (Boise, L., *Cell,* 74: 597–608, 1993). The in vivo pattern of Bcl-$x_L$ expression is distinct from the Bcl-2 (Boise, L., *Cell,* 74: 597–608, 1993). p29Bcl-$x_L$ also renders cancer cells resistant to a variety of anticancer agents, including taxanes, Fas signaling, oxidants and radiation (Ibrado, A. M., et al., *Cell Growth & Differ.* 7: 1087–1094, 1996; Ibrado, A. M., et al., *Cancer Res.,* 57: 1109–1115, 1997; Minn, A. J., et al., *Blood* 86: 1903–1910, 1995; Datta, R., et al., *Cell Growth & Differ.* 6: 363–370, 1995; Ibrado, A. M., *Cancer Res.,* 56: 4743–4748, 1996). Bcl-$x_L$ has also been shown to block apoptosis where Bcl-2 is ineffectual (Gottschalk, A. R., et al., *Proc. Natl. Acad. Sci. USA,* 91: 7350–7354, 1994). In addition, a new member of the Bcl-2 family called Bak has also been isolated which like Bax promotes apoptosis (Keifer, M. C., et al., *Nature,* 374: 736–739, 1995). Bak heterodimerizes with Bcl-$x_L$ but not Bcl-2, and may also facilitate the generation of free Bax resulting in the formation of Bax homodimers (Keifer, M. C., et al., *Nature,* 374: 736–739, 1995). A novel protein, Bag-1, which binds to Bcl-2 but is not its homolog, synergizes with Bcl-2 to inhibit apoptosis (Takayama, S., *Cell,* 80: 275–284, 1995).

Bcl-2 and Bcl-$x_L$ as Membrane Channel Proteins

Recently, the three-dimensional structure of Bcl-$x_L$ has been shown to have two central hydrophobic helices surrounded by five amphipathic helices, as well as a 60-residue flexible loop domain (Muchmore, S. W., et al., *Nature,* 381: 335–341, 1996). This structure has homology to the pore-forming domains of bacterial toxins. Similarly, in the membranes, Bcl-$x_L$ forms an ion-conducting channel that displays multiple conductance states (Minn, A. J., et al., *Nature,* 385: 353–357, 1997). These conductance states of Bcl-$x_L$, including a more complex large conductance channel, could result either from interaction with the other members of the pore-forming Bcl-2 families of proteins or from the distinct conformations that Bcl-$x_L$ may adopt (Minn, A. J., et al., *Nature,* 385: 353–357, 1997). The channel property of Bcl-$x_L$ may influence the mitochondrial permeability transition and other important mitochondrial functions (Zoratti, M., et al., *Biochimica et Biophysica Acta,* 1241: 139–176, 1994). In addition to being an ion-selective channel, Bcl-$x_L$ may facilitate the passage of other important proteins, such as cyt c, that trigger the cleavage and activity of caspase-3 and apoptosis (Golstein, P., *Science,* 275: 1081–1082, 1997). Interaction of Bcl-$x_L$ with Bax or other Bcl-2-related proteins could also influence the channel function of Bcl-$x_L$ for cyt c (Gajewski, T. F., et al., *Cell,* 87: 589–592, 1996). Furthermore, the post-translational modification of Bcl-2 and Bcl-$x_L$ by phosphorylation may also modulate its channel function, because Bcl-2 phosphorylation has been shown to be associated with an increase in free Bax levels and induction of apoptosis (Ibrado, A. M., et al., *Cancer Res.* 57: 1109–1115, 1997; Halder S., et al., *Proc. Natl. Acad. Sci USA,* 92: 4507–4511, 1995; Blagosklonny, M. V., et al., *Cancer Res.,* 57: 130, 1997). Collectively, these observations help explain and are consistent with the finding that the over expressed Bcl-2 or Bcl-$x_L$ dimerized with Bax inhibits mitochondrial release of cyt c, which appears to precede the $\Delta\psi$m collapse and increase in the ROS (Kim, C. N., et al., *Cancer Res.,* 57: 3115–3120, 1997).

V. INHIBITION OF PROTEIN KINASE C

Protein Kinase C (calcium/phospholipid protein kinase; referred to below as PKC) catalyzes the phosphorylation of the amino acids serine and threonine (Edelman, A., et al., *Ann. Rev. Biochem.* 56: 567, 1987). The enzyme was first characterized from brain tissue (Takei, et al., *J. Biol. Chem.* 252: 3692, 1997) and is now known to occur in virtually all tissues of the body (Kuo, et al., *Proc. Natl. Acad. Sci. USA.* 97: 7039, 1980). At least seven isozymes of PKC have been purified, cloned, and expressed. The distribution of the known isozymes of PKC varies significantly among different tissues (Huang, F., et al., *J. Biol. Chem.* 262: 15714, 1987), suggesting that different isozymes may have different functions (Coussens, L., et al., *Science* 233: 859, 1986; Ono, Y. and Kikkawa, U., *Trends Biochem. Sci.*12: 421, 1987).

The isozymes of PKC have been shown to have a varying dependency on three allosteric modulators: $Ca^{2+}$, phosphatidylserine, and diacylglycerol (Nishizuka, Y., *Nature* 334: 661, 1988). The mechanism of PKC activation by diacylglycerol, $Ca^{2+}$, and phospholipid is complex and not entirely understood.

The binding of a wide variety of extracellular hormones, neurotransmitters, and growth factors to their extracellular receptors stimulates the hydrolysis of phosphatidylinositols (Berridge, M., *Ann. Rev. Biochem.* 56: 159, 1987), phosphatidylcholines (Besterman, J., et al., *Proc. Natl. Acad. Sci. USA.* 83: 6785, 1986), and phosphatidylethanolamines (Kester, M., et al., *J. Clin. Invest.* 83: 718, 1989) to yield diacylglycerol. Production of diacylglycerol in turn stimulates protein phosphorylation by PKC. These pathways suggest that PKC may play an important role in signal transduction, cellular proliferation and differentiation, tumor promotion, and neurotransmission.

The importance of PKC in cellular regulation is highlighted by the observation that phorbol diesters, which initiate cell proliferation, differentiation, arachidonate metabolism, oxygen metabolism, tumor promotion, and intense inflammation, bind to PKC at the same site as diacylglycerol and activate the enzyme (Niedel, et al., *Proc. Natl. Acad. Sci. USA.* 80: 36, 1983). Phorbol esters are derivatives of cyclopropabenzazulene. PKC is now thought to mediate most, if not all, of the biological effects of the diesters.

Inactive PKC is largely cytosolic, and upon activation, is rapidly translocated to biological membranes. Phosphatidylserine is the most effective phospholipid in activating PKC when added with diacylglycerol and probably serves to mimic a biological membrane to which active PKC always binds.

Many studies have suggested that diacylglycerol (DAG) has an important role in stimulating leukocytes. Stimulants of PKC, such as phorbol esters, cause redistribution of PKC from the cytosol to particulate fraction in neutrophils and monocytes (Snyderman, R. and Uhing, R., In: *Inflammation: Basic Principles and Clinical Correlates*, 309, edited by Gallin J. I., et al. (New York: Raven Press, Ltd. 1988). In addition, phorbol myristate acetate, in the presence of cytochalasin B, stimulates neutrophil degranulation (Goldstein, I., *Contemp. Top. Immunobiol.* 14: 189, 1984). The relative potencies of various phorbol esters to cause PKC translocation are similar to their stimulatory effects on white cell superoxide production (Myers, M., et al., *J. Immunol.* 135: 3411, 1985). The bacterial cell wall-derived peptide, formyl-Met-Leu-Phe (fMLP), a very potent chemotactic factor for leukocytes, increases membrane-associated PKC at concentrations that also stimulate respiratory burst (Pike, M., et al. *Blood* 67: 909, 1986; McPhail, L., et al. *Fed. Proc.* 43: 1661, 1984). Agents that inhibit chemoattractant activation of neutrophil respiratory burst specifically inhibit the translocation of PKC to the plasma membrane (Pike, M., et al., *Blood.* 67: 909, 1986). Thus, translocation of PKC to the plasma membrane appears to be crucial for activation of the respiratory burst induced in neutrophils by fMLP. Evidence indicates that both neutrophil secretion and respiratory burst may be regulated either by different compartments of PKC, or different isozymes of PKC (Cox, C., et al., *J. Immunol.* 136: 4611, 1986). There is also data to suggest that the differentiation of monocytes to macrophages is mediated by PKC (Snyderman, R. and Uhing, R., In: *Inflammation: Basic Principles and Clinical Correlates*, edited by Gallin, J., et al. (New York: Raven Press, Ltd., 309, 1988)).

In light of the wide ranging biological functions of PKC, it would be of great therapeutic value to have specific modulators of the enzyme. For example, interleukin-1 is a primary mediator of inflammatory diseases such as rheumatoid arthritis, and evidence exists to suggest that PKC mediates some of the effects of interleukin-1. Thus, a PKC inhibitor may be useful for treatment of inflammatory disease, blocking the effects of interleukin-1 as well as other inflammatory mediators such as bradykinin and substance P. Since activation of PKC serves as a power proliferative signal in many tissues, a PKC inhibitor may also be of utility in proliferative diseases such as psoriasis, cancer and other metastatic illnesses. In addition, the brain and several endocrine organs contain large amounts of protein kinase C. As a result, a PKC inhibitor may find utility in certain neurological or endocrine diseases. In addition, a vascular PKC inhibitor may have utility as a therapy for essential hypertension.

PKC inhibitors include sphingosine and certain related sphingolipids. (Bell, R., et al. *Cold Spr. Harbor Sym. Quant. Biol.* 53: 103, 1988). This groups of compounds compete with the phorbol ester binding site and thus have the potential for specificity. However, not only has sphingosine also been reported to inhibit $Ca^{2+}$/calmodulin protein kinase (Jefferson, A. and Schulman, H., *J. Biol. Chem.* 263: 15241, 1988), but sphingosines may inhibit other biological processes in a nonselective manner (Pittet, D., et al., *J. Biol. Chem.* 262: 10072, 1987; Winicov, I. and Gershengorn, M., *J. Biol. Chem.* 263: 12179, 1988).

As one embodiment of the invention disclosed herein, a sphingolipid metabolic altering compound is administered in an effective treatment amount to inhibit protein kinase C in a host in need of treatment. By administering the sphingolipid in this type of prodrug state, wherein $R^2$ is either one of the listed groups that can be cleaved by an enzyme in vivo, or wherein $R^2$ is a targeting moiety, one can ameliorate problems associated with nonselective responses. An example of this targeting would be the feeding of complex sphingolipids that are digested in the colon to release the sphingoid base (for example, sphingosine) backbone, to inhibit protein kinase C in colon tumors.

As one aspect of this invention, inflammatory disorders that are mediated by PKC can be treated by administration of an antiinflammatory treatment amount of a sphingolipid metabolism altering compound, or its pharmaceutically acceptable salt. An inflammatory response is a pathologic condition that can occur in response to immunologically non-specific injury, either from physical (such as trauma), chemical, or biologic agents. An inflammatory response is characterized by increased blood flow and redness in the inflamed area, increased capillary permeability and edema, and recruitment of immunologically non-specific white blood cells, especially neutrophils, that remove injurious material and promote repair. Cellular products of lymphocytes may contribute to or induce an inflammatory response. Examples of inflammatory disorders that may be treated by the sphingolipid metabolism altering compound include but are not limited to inflammatory bowel disease, psoriasis, proliferation of smooth muscle cells in the course of development of plaques in vascular tissue.

In one example, the initial phase of anaphylaxis, including attacks of allergic asthma, is due largely to degranulation and mediator release from mast cells (Friedman, M. and Kaliner, M., *Am. Rev. Respir. Dis.* 135: 1157, 1987; Kaplan, A. and Silverberg, M., *Methods Enzymol.* 163: 3, 1988). These mediators, including histamine and several eicosanoids, cause airway smooth muscle spasm, vasodilation and plasma extravasation, and are the major culprits in acute allergic inflammation. The biochemical mechanisms leading to cell activation subsequent to IgE binding to and cross-linking of its receptors on the mast cell surface are not completely understood. However, mast cell mediator release is calcium-dependent (Pearce, F., I. *Asthma Reviews*, 1: 95; edited by Morley J. (London: Academic Press Ltd., 1987); (Siraganian, R., *Inflammation: Basic Principles and Clinical Correlates*, edited by Gallin, J., et al. (New York: Raven Press Ltd., 513, 1988)). Increased turnover of mast cell phosphoinositides (PI), following both IgE-mediated and pharmacological stimulation has been established (Pearce, F., I. *Asthma Reviews, Volume* 1, edited by Morley J. London: Academic Press Ltd., 95, 1987), and PI turnover closely correlates with histamine secretion. It has also bee suggested that the PI response generates arachidonic acid, that is metabolized further to produce thromboxane, prostanoids and leukotrienes. In addition, the PI cycle generates DAG which, as has already been discussed, stimulates PKC. PKC acts synergistically in many cells to evoke the secretory response (Drummond, A. and MacIntyre, D., *Trends Pharmacol. Sci.* 6: 233, 1985). Indeed, phorbol esters, by activating PKC, stimulate mediator secretion both from mast cells and basophils (Siraganian, R., *Inflammation: Basic Principles and Clinical Correlates,* 513, edited by Gallin, J., et al. (New York: Raven Press Ltd., 1988); Schleimer, R., et al., *J. Immunol.* 126: 570, 1981.) Further, during mast cell activation there is an increase in membrane-associated PKC. (White, J., et al., *Proc. Natl. Acad. Sci. USA.* 82: 8193, 1985).

VI. MODIFICATION OF THE COLONIZATION OF MICROFORA

Many microorganisms, microbial toxins, bacteria and viruses have receptors which bind to cells via sphingolipids. Therefore, populating the binding site with sphingolipid analogs, including but not limited to the compounds described herein, in the prodrug state or as metabolized, serves to (i) decrease the colonization of the microorganism, and (ii) modify the colonization of microfora that influence colon caner and other disorders of the intestine. The compound binds to the sphingolipid receptor of the microorganism, saturating the receptor and facilitating elimination of the organisms and toxins.

In an additional embodiment of the present invention, a process for modifying the colonization of microfora that influence colon cancer and other intestinal disorders is provided that comprises administering an effective amount of a sphingolipid derivative to a host.

These compounds can in particular be used to treat infections caused by bacteria (gram negative and gram positive) and viruses which have receptors for sphingolipids as anchoring means for colonization. Nonlimiting examples of microorganisms that can be treated using this method include cholera toxin, verotoxin, Shiga-like toxin 2e, *Clostridium botulinum* type B neurotoxin, *Escherichia coli, Haemophilus influenzae; Helicobacter pylori; Borrelia burgdorferi, Pseudomonas aeruginosa, Candida albicans,* HIV, Sendai virus, and influenza viruses. In this embodiment, an effective amount of a selected compound falling within the above formula is administered to decrease or prevent colonization of the selected microorganism.

VII. PREPARATION OF ACTIVE COMPOUNDS

Compounds described herein can be prepared using literature methods, including for example, in U.S. Pat. Nos. 5,232,837, 5,518,147, and 5,110,987, or routine modifications of these methods. The addition of the $R^2$ groups can be accomplished using the method described below or a modification thereof.

Additional information concerning the synthesis of compounds described herein can be obtained from the following references: Bruzik, K. S. The synthesis and absolute configuration of thiosphingomyelins (*Journal of the Chemical Society. Chemical Communication,* 329–331, 1986.) Synthesis and spectral properties of chemically and stereochemically homogenous sphingomyelin and its analogues (Bruzik, K. S., et al., *Journal of Chemical Society. Perkin Trans.* 1: 423–431, 1998.) H-Phosphonate and phosphoramidite methods for the synthesis of sphingophospholipids (Frantova, A. Y., et al., *Bioorganicheskaya Khimiya.;* 17: 1562–1573, 1991.) Facile synthesis of α- and β-O-glycosyl imidates; preparation of glycosides and disaccharides (Schmidt, R. R., et al., *Angewandte Chemie, Int. Ed. Engl.;* 19: 731–732, 1980); Short Synthesis of Cerebrosides, (Schmidt, R. R., et al., *Angewandte Chemie. Int. Ed. Engl.,* 24(1): 65–66, 1985); Selective Synthesis of Cerebrosides; (2S, 3R, 4E)-1-O-β-D-galactopyranosyl-N-(2'-hydroxytetracosanoyl-sphingenine (Koike, K. et al., *Glycoconjugate Journal,;* 2: 105–108, 1985); The synthesis of aryl-D-β-glucopyranosiduronic acids, (Bollenback, G. N., et al., *Journal of the American Chemical Society.* 77: 3310–3315, 1955); Stereoselective total synthesis of wheat flour ceramide dihexoside. (Koike, K., et al., *Agricultural and Biological Chemistry,* 54: 2931–2939, 1990); Einfache Synthese von, β-D-Glucopyranosyluronaten. (Schmidt, R. R., et al., *Synthesis,* 885–887, 1981); The Synthesis and Configurational Stability of Differentially Protected β-Hydroxy-α-amino Aldehydes. (Garner, P., et al., *Journal of Organic Chemistry;* 52: 2361–2364, 1987); 1,1-Dimethylethyl (S)- or (R)-4-formyl-2,2-dimethyl-3-oxazolidinecarboxylate: a useful serinal derivative. (Garner, P. et al., *Organic Synthesis,* 70: 18–28, 1991); Synthesis of D-erythro- and D-threo-sphingosine derivatives from L-serine. (Herold, P., *Helvetica Chimica Acta,* 71: 34–362, 1988); A stereodivergent synthesis of D-erithro-sphingosine and D-threo-sphingosine from L-serine. (Garner, P. et al., *Journal of Organic Chemistry,* 53: 4395–4398, 1988); Total Synthesis of Symbioramide, a Novel Ca-2+-ATPase Activator from Symbiodinium-Sp. (Yoshida, J. et al., *Journal of the Chemical Society. Perkin Transaction,* 1: 343–350, 1992); Synthesis of Sphingosine Relatives, XIV. A New Synthesis of Symbioramide, a Ca++-ATPase Activator from Symbiodinium sp. (Mori, K. et al., Liebigs Annalen der Chemie, 41–48, 1994); Shapiro, D., *Chemistry of sphingolipids.* Paris, 1969); Synthesis of D-Erythro-Sphingomyelin and D-Erythro-Ceramide-1-Phosphoinositol. (Kratzer, B. et al., *Tetrahedron Letters,* 34: 6881–6884, 1993); Efficient Synthesis of Sphingosine-1-phosphate, Ceramid-1-phosphate, Lysosphingomyelin, and Sphingomyelin. (Kratzer, B., et al., *Liebigs Ann.,* 957–963, 1995).

EXAMPLE 1

The Total Chemical Synthesis of N-Palmitoylsphingomyelins and 1-O-β-D-Glucoronoyl-2-N-Palmitoylsphingosine (Glucoronocerebroside)

Figure 6:
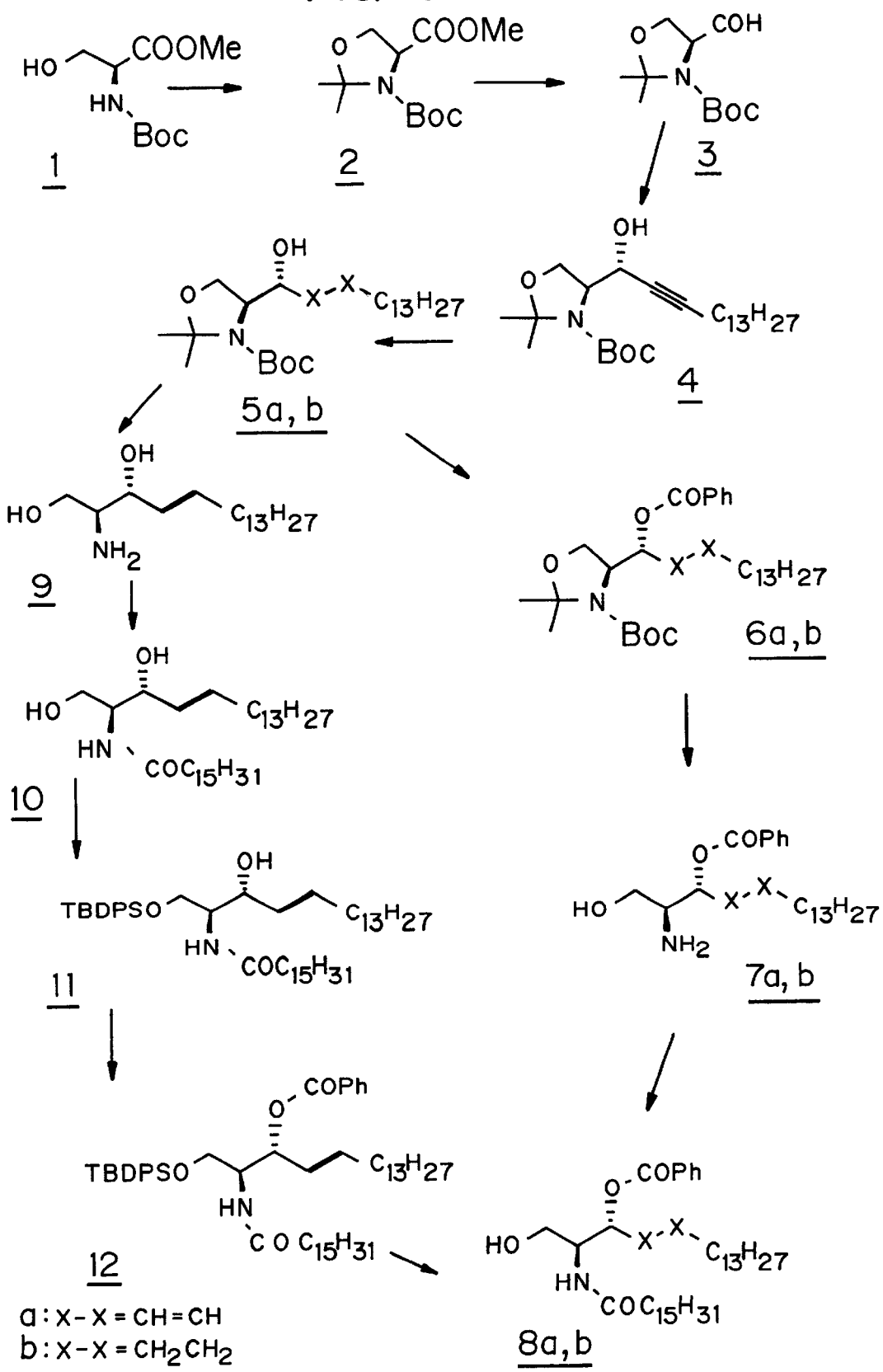
FIG. 6 is a schematic of one example of a synthesis of saturated and unsaturated 3-O-benzoylceramides (8a,b), key intermediates in the syntheses of glyco- and phosphosphingolipids. This process can be adapted for the preparation of other 3-O-protected ceramides (Acetyl, Pivaloyl, t-Butyldimethylsilyl, t-Butyl-diphenylsilyl), commonly used in the syntheses of sphingomyelins and glycosphingolipids.
Figure 7:
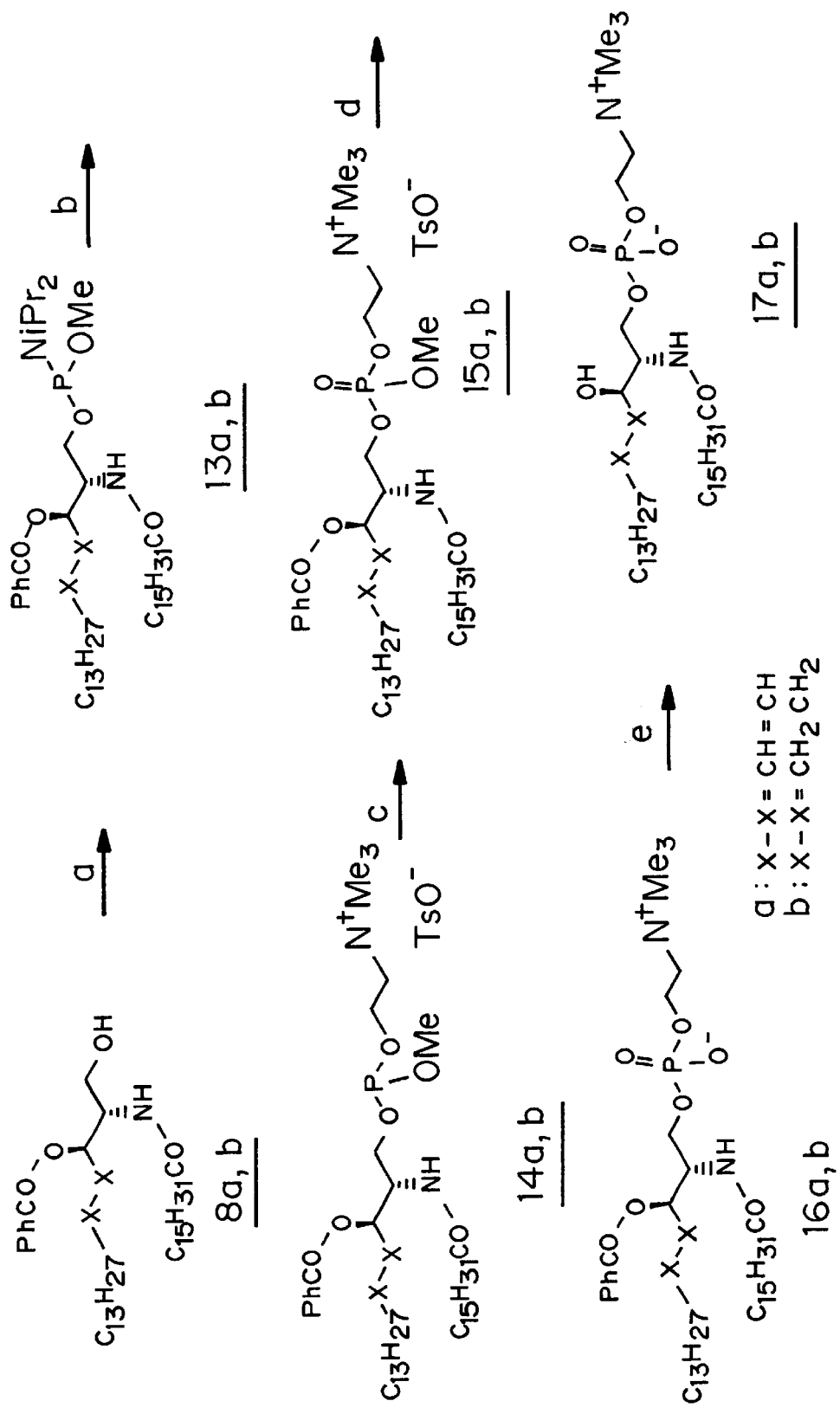
FIG. 7 is a schematic of a synthesis of sphingomyelins that involves a phosphite triester. The scheme includes the steps of phosphitilation of 3-O-benzoylceramides (8a,b) with chloro(N,N-diisopropylamino)-methoxyphosphine in the presence of triethylamine, the condensation of the crude amidites (13a,b) with 4–5 times excess of tosylate choline in the presence of 1H-tetrazole, oxidation with tert-butylhydroxyperoxide and removing of the blocking groups in the phosphoric acid residue with tert-butylamine and hydroxy group at C3 with sodium methoxide.
Figure 8:
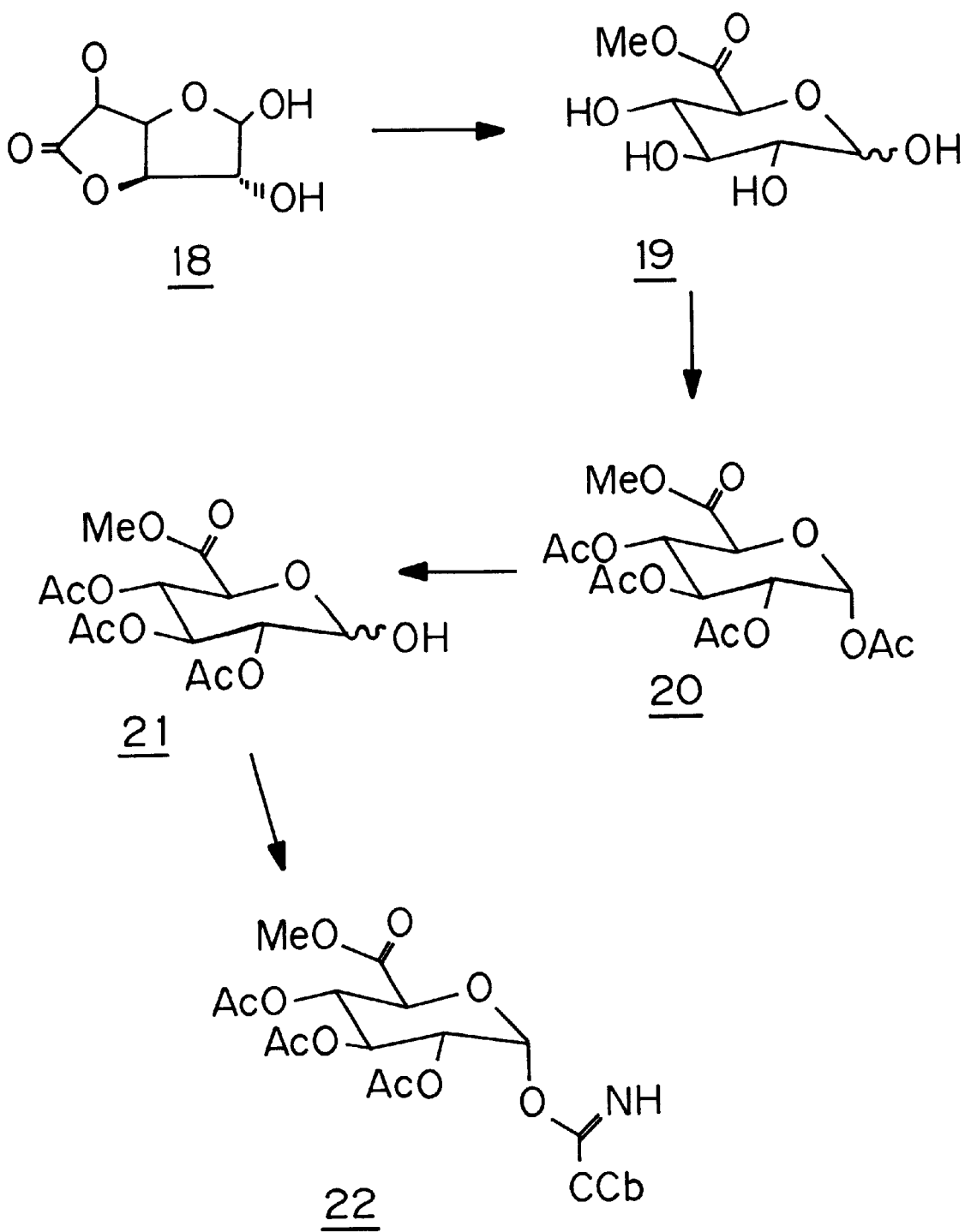
FIGS. 8 and 9 together are a schematic of a synthesis of β-D-glucuronylceramide (23).
Figure 9:
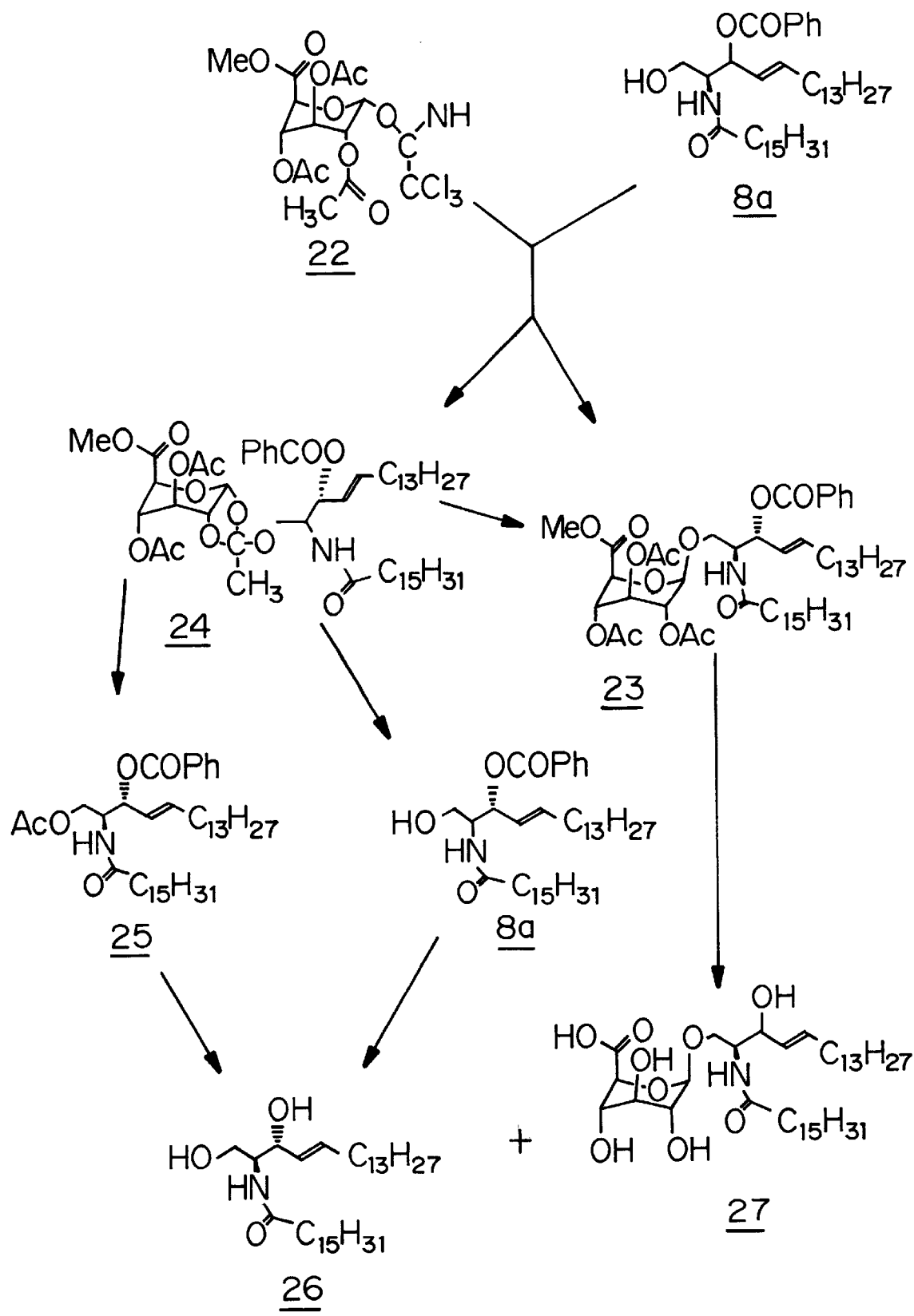

FIG. 6 illustrates a short seven-step synthesis of D-erythro-3-O-benzoylceramides (8a,b), that includes use of commercially available N-Boc-L-Ser-OMe (1) as the starting material. The synthesis provided yields of 27 and 31%, respectively. Phosphytilation with O-methyl-N,N-diisopropylaminophosphorochloridite was employed for the introduction of the phosphoryl choline moiety into (8a,b). This allowed for the preparation of D-erythro-N-palmitoylsphingomyelin (17a) and D-erythro-N-palmitoyldihydrosphingomyelin (17b) in total yields 15 and 20%, respectively. Coupling of 3-O-benzoylceramide (8a) and glucuronylimidate (22) in methylene dichloride in the presence of borontrifluoride etherate and 4 Å molecular sieves resulted in the formation of all-protected β-D-glucoronoylceramide (23). Hydrolysis of the glycosylation product (23) with methanolic potassium hydroxide in the presence of water resulted in the one-step deprotection of hydroxy and carboxylic functions and led to the target compound, β-D-glucoronocerebroside (27).

Materials and Analytical Procedures.

Palmitoyl chloride, benzoyl chloride, N-Boc-L-serine methylate (1), chloro (N,N-diisopropylamino)-methoxyphosphine, D-gluronolactone (18), borontrifluoride etherate, 2,2-dimethoxypropane, 1H-tetrazole (sublimated), hydrazine acetate, triethylamine were purchased from Aldrich and used without further purification. tert-Butylhydroperoxide, DIBAL-H, n-BuLi (1.6 M solution in hexanes), LAH (1.0 M solution in THF), were purchased from Aldrich,. Pentadecyne was purchased from Lancaster. Choline tosylate was purchased from Sigma or prepared from choline hydroxide (from Aldrich) and p-toluenesulfonic acid monohydrate. All melting points are uncorrected. Unless otherwise stated, IR spectra were recorded as a film with mineral oil on sodium chloride discs using an Impact 400 IR spectrometer and only the structurally important peaks are listed. $^1H$ and $^{13}C$ NMR spectra were recorded on a General Electric QE-300 (300 MHZ 1H, 75.5 MHZ $^{13}C$) spectrometer in deuteromethanol and/or deuterochloroform. The positive and negative ion FAB mass spectra were taken on JEOL spectrometer. Merck Silica Gel 60 TLC plates of 0.25 mm thickness were used to monitor the reactions, with visualization by heating with the Sigma spray reagent molybedenum blue (for phosphorus containing compounds) and Horcinol spray reagent. Flash column chromatographies were performed using Silica Gel 60 (Merck, 230–400 mesh ASTM). Elemental analyses were performed by Atlantic Microlab, Inc., Norcross, Ga. Optical rotations were measured in 1 dm tube with a Perkin-Elmer Polarimeter 241MC (USA).

Experimental procedures.

The synthesis of 3-O-benzoylceramides (8a,b).

According to the methods given in Garner, P. et al., (*J. Org. Chem.* 52: 2361–2364, 1987; *Orgainic Synthesis*, 70: 18–28, 1991), the synthesis of 3-(1,1-dimethylethyl)-4-methyl-(S)-2,2-dimethyl-3,4-oxazolidinedi-carboxylate from N-Boc-L-Ser-OMe was carried out in a yield of 76–78%, $[a]_D^{25}$ –57.63° (c=1.30, $CHCl_3$). Lit. $[\alpha]_D$ –46.7° (c=1.30, $CHCl_3$). the reduction of isopropylidene derivative with DIBAL leads to the aldehyde in a yield of 84–85%. $[\alpha]_D^{25}$ –96.40° (c=1.34, $CHCl_3$). Lit. $[\alpha]_D$ –91.7° (c=1.34, $CHCl_3$). The condensation of pentadecyne to aldehyde lead to the formation of 1,1-dimethyl [R-(R*,S*)]-2,2-dimethyl-4-(1-hydroxy-2-hexadecynyl)-3-oxazolidinecarboxylate as described in Harold, P., *Helvetica Chimica Acta* 71: 354–362, 1988; and Garner, P., et al., *J. Org. Chem.* 53: 4395–4398, 1988.

Yield 58.0%, $[\alpha]_D^{23}$ –39.0° (c=1.43, $CHCl_3$). Mass-spectrum, m/z: 438.36. $(M+H)^+$ $C_{26}H_{48}NO_4$ requires 438.36. Lit. $[\alpha]_D$ –39.7° (c=1.41, $CHCl_3$).

1,1-Dimethyl [R-(R*,S*)]-2,2-dimethyl-4-(1-benzoyloxy-2-hexadecynyl)-3-oxazolidinecarboxylate (6a). A solution of hexadecyne derivative (4) (6.30 g, 14.39 mmol) in THF (500 mL) was added dropwise to a solution of Li (5.2 g) in liquid ammonia (500 mL) at –75° C. for 6 h, after which ammonium chloride (125 g), ethylacetate (650 mL), and water (400 mL) were sequentially added. The organic layer was separated and the aqueous layer was washed with EtOAc (2×500 mL). The organic solutions were combined, dried with magnesium sulfate, and concentrated in vacuo. The residue, 1,1-dimethyl [R-(R*,S*)]-2,2-dimethyl-4-(1-hydroxy-2-hexadecenyl)-3-oxazolidinecarboxylate (5a) (6.3 g, ~100%, homogeneous by TLC analysis using hexane-EtOAc, 3:1; $R_f$ 0.37) was taken up by a mixture of methylene dichloride (70 mL) and pyridine (8 mL) and to this was added benzoyl chloride (5.0 mL, 6.1 g, 43 mmol) at 0° C. over a period of 15–20 min. The reaction mixture was allowed to warm to room temperature over a period of 5 h. Water (3 mL) was then added and stirring was continued overnight. The reaction mixture was diluted with ether (1 L) and the ether solution was washed sequentially with 10% sodium bicarbonate solution (2×100 mL), brine (2×100 mL), dried over magnesium sulfate, and concentrated in vacuo. The residue was chromatographed on silica gel (270 g) using hexane-EtOAc, 9:1 as the eluent.

Yield 6.75 g (86.3%). $R_f$ 0.50 (Hexane-EtOAc, 6:1), $[\alpha]_D^{23}$ –30.2° (c=1.49, $CHCl_3$), IR (neat): 1723, 1702, 1268, 1175, 1107, 1069 ($cm^{-1}$). Calculated %: C, 72.89; H, 9.82; N, 2.58 for $C_{33}H_{53}NO_5$. Found %: C, 72.84; H, 9.85; N, 2.55. Mass-spectrum, m/z: 550.41, $(M+Li)^+$ $C_{33}H_{53}NO_5Li$ requires 550.41.

1,1-Dimethyl [R-(R*,S*)]-2,2-dimethyl-4-(1-benzoyloxy-2-hexadecynyl)-3-oxazolidinecarboxylate (6b). According to the method described in Yoshida, J., et al., *J. of the Chemical Society. Perkin Transaction I* 343–350, 1992, alkyne derivative (4) (16.82 g, 38,43 mmol) was hydrogenated at room temperature in ethyl acetate (200 mL) over platinum oxide with hydrogen at atmospheric pressure for 2 h (yield~100%). The product 5b exhibited the following characteristics:

$R_f$ 0.46 (Hexane-EtOAc, 9:2), $[\alpha]_D^{25}$ –13.74° (c=0.84, $CHCl_3$), IR (neat): 3434, 1697, 1675, 1459, 1381, 1252, 1170, 1092, 1066, 841 ($cm^{-1}$). Mass-spectrum: m/z: 442.39. $(M+H)^+$ $C_{26}H_{52}NO_4$ requires 442.39. Lit. $[\alpha]_D^{21}$ –13.0° (c=1.03, $CHCl_3$) [15]. The product 5b was transformed to 6b using the procedure employed for the conversion of 5a to 6a [yield 95–98%, $R_f$ 0.55 (Hexane-EtOAc, 6:1), IR (neat): 2916, 2851, 1722, 1699, 1454, 1389, 1269, 1172, 1103, 849, 706 ($cm^{-1}$). Mass-spectrum: m/z: 546.41. $(M+H)^+$ ($C_{33}H_{56}NO_5$ requires 546.41).

D-erythro-3-Benzoyl-2-N-palmitoyl-sphingosine (3-O-benzoylceramide) (8a). To a solution of a benzoyl derivative 6a (6.75 g, 12.4 mmol) in methylene dichloride (150 mL) was added trimethylsilyl iodide (2.2 mL, 3.1 g, 15.5 mmol), and reaction mixture was stirred at 20–25° C. for 2–3 h. A water methanol mixture (1:4, 10 mL) was added and after 15 min the reaction mixture was concentrated in vacuo. The residue [crude 3-O-benzoylsphingenine (7a), $R_f$ 0.58, chloroform-methanol-25% ammonium hydroxide, 7:1:0.1] was taken up in a mixture of THF (160 mL) and 1M acetic acid (60 mL) and a solution of palmitoyl chloride (3.70 g, 13.5 mmol) in THF (30 mL) and saturated solution of sodium acetate (160 mL) were added simultaneously. The reaction mixture was allowed to stir at 20–25° C. for 2 h, after which the mixture was diluted with water (250–300 mL). The precipitate was separated by filtration, washed sequentially with 5% sodium bicarbonate and water, dried in air, and crystallized from ethanol (150 mL).

The yield was 5.71 g (71.7%). Mp 88.0–88.5° C., $[\alpha]_D^{25}$ +21.0° (c=1.07, $CHCl_3$). Lit. Mp 88–90° C., $[\alpha]_D$+13.0° [Shapiro, D. *Chemistry of Sphingolipids, Paris*, 1969].

D-erythro-3-Benzoyl-2-N-palmitoyldihydrosphingosine (3-O-benzoyldihydroceramide) (8b). Starting from 3-O-benzoyl derivative (6b) (4.63 g, 8.48 mmol) 3-benzoylceramide (8b) as prepared with the yield 82–83%. Mp 75.0–75.5° C. (MeOH), $[\alpha]_D^{25}$+32.56° (c=1.26, $CHCl_3$).

IR (in mineral oil): 3427 (OH), 3300 (NH), 1717 and 1693 (C=O of benzoate), 1638 (amide I), 1537 (amide II), 1276 (C-O of benzoate) ($cm^{-1}$). Lit. Mp. 78–80° C., $[\alpha]_D$+26.0° [Shapiro, D. *Chemistry of Sphingolipids, Paris*, 1969].

The synthesis of sphingomyelins (17 a,b).

D-erythro-3-O-Benzoyl-2-N-palmitoylsphingenine-1-phosphorylcholine (3-O-benzoyl-sphingomyelin) (16a). To a solution of 3-O-benzoylceramide (8a) (2.79 g, 4.34 mmol) in methylene dichloride (25 mL) were added triethylamine (1.4 mL, 1.02 g, 10.08 mmol) and chloro (N,N-diisopropylamino)methoxyphosphine (1.20 g, 1.18 mL, 6.1 mmol), and the resulting reaction mixture was allowed to stir at 20–25° C. for 1 h. After this time the reaction appeared to be complete (TLC control, hexane-ether-$Et_3N$, 20:40:1) and so the reaction mixture was concentrated in vacuo, dried by reevaporation with toluene. The residue (crude amidite 13a), was dissolved in THF (20 mL) and to the solution were added choline tosylate (4.60 g, 16.7 mmol) in acetonitrile (35 mL) and 1H-tetrazole (1.20 g, 16.9 mmol) in acetonitrile (25 mL). the reaction mixture was allowed to stir at 20–25° C. for 2.5 h. After the reaction appeared to be complete (TLC control, hexane-$Et_3N$, 20:1), tert-butyl hydroperoxide (5.0–6.0 M solution in 2,2,4-trimethylpentane) (25 mL) was added and the reaction mixture was allowed to stir at 20–25° C. for 2 h. After the oxidation of phosphite triester (14a) to its corresponding phosphate triester (15a) appeared to be complete (TLC control, chloroform-methanol-ammonium hydroxide, 25%, 7:1:0.1), the reaction mixture was concentrated in vacuo and the residue was dissolved in methylene dichloride (20 mL). tert-Butylamine (10 mL) was then added and the reaction mixture was allowed to stir at 20–25° C. overnight. The reaction mixture was concentrated in vacuo and the residue was chromatographed on silica gel (175 g) using a mixture chloroform-methanol-water, 65:35:4, yielding 2.35 g (67.1%) of 3-O-benzoylsphingomyelin (16a), amorphous solid, $R_f$ 0.51 (chloroform-methanol-acetic acid-water, 100:50:16:8). $[\alpha]_D^{23}$+6.08° (c=1.15, $CHCl_3$).

IR (in mineral oil): 3500, 3300, 1715 (C=O of benzoate), 1645 (amide I), 1540 (amide II), 1262 (C-O of benzoate), 1119–1034 (PO$_3$), 966, 716 (cm$^{-1}$). Mass-spectrum: m/z: 807.60 (M+H)$^+$ (C$_{46}$H$_{84}$N$_2$O$_7$ requires 807.60).

D-erythro-2-N-Palmitoylsphingenine-1-phosphorylcholine (N-Palmitoylsphingomyelin) (17a). To a solution of 3-O-benzoylsphingomyelin (16a) (2.06 g, 2.55 mmol) in methanol (25 mL) was added 2M sodium methoxide solution in methanol (2.5 mL), and the reaction mixture was allowed to stir at 20–25° C. for 2 h. The reaction mixture was neutralized with acetic acid, concentrated in vacuo and the residue was chromatographed on silica gel using a mixture chloroform-methanol-water (65:35:4) yielding 1.74 g (97.2%) of sphingomyelin (17a) (monohydrate). Mp~190° C., R$_f$=0.36 (chloroform-methanol-acetic acid-water, 100:50:16:8). [α]$_D^{22}$+5.6° (c=1.02, CHCl$_3$-MeOH, 1:1) or +4.3° (c=1.07, CHCl$_3$-MeOH-H$_2$O, 65:35:4).

Mass spectrum: m/z: 703.58 (M+H)$^+$ (C$_{39}$H$_8$N$_2$O$_6$P requires 703.58). Lit. mp 215–217° C., [α]$_D^{25}$+6.1°, or [α]$_D$+6° [c=1, CHCl$_3$-MeOH, 1:1] [Kratzer, B., *Tetrahedron Letters*, 34: 6881–6884, 1993; and Kratzer, B., et al., *Liebigs Ann*. 957–963, 1995].

D-erythro-3-O-Benzoyl-2-N-palmitoylsphinganine-1-phosphorylcholine (3-O-benzoyl-dihydrosphingomyelin) (16b). To a solution of 3-O-benzoyldihydroceramide (8b) (4.84 g, 7.51 mmol) in methylene dichloride (40 mL) were added triethylamine (2.42 mL) and chloro (N,N-diisopropylamino) methoxyphosphine (2.07 g, 2.03 mL, 10.5 mmol), and the reaction mixture was allowed to stir at 20–25° C. for 1 h. After the reaction appeared to reach completion (TLC control, hexane-ether-Et$_3$N, 20:40:1), the reaction mixture was concentrated in vacuo and dried by reevaporation with toluene. The residue (crude amidite 13b), was dissolved in THF (36 mL) and choline tosylate (7.90 g, 28.7 mmol) in acetonitrile (86 mL) and 1H-tetrazole (2.02 g) in acetonitrile (50 mL) were added. The reaction mixture was allowed to stir at 20–25° C. for 4.5 h. After reaction appeared to reach completion (TLC control, hexane-Et$_3$N, 20:1), tert-butyl hydroperoxide (5.0–6.0 M solution in 2,2,4-trimethylpentane) (8.0 mL) was added and the reaction mixture was allowed to stir at 20–25° C. for 1.5 h. After oxidation of phosphite triester (14b) to the corresponding phosphate triester (15b) appeared to be completed (TLC control, chloroform-methanol-ammonium hydroxide, 25%, 7:1:0.1), the reaction mixture was concentrated in vacuo and the residue was dissolved in methylene dichloride (50 mL). tert-Butylamine (50 mL) was added and the reaction mixture was allowed to stir at 20–25° C. for ~20 h. The reaction mixture was concentrated in vacuo and the residue was chromatographed on silica gel (175 g) using a mixture chloroform-methanol-water (165:35:4). The resulting product was further purified via an Amberlite MB-3 column by using a mixture of chloroform-methanol-water (7:7:1) as the eluent.

Yield=4.39 g (71.9%), amorphous product 16b (as monohydrate), R$_f$=0.51 (CHCl$_3$-methanol-acetic acid-water, 100:50:16:8), IR (in mineral oil): 3343, 1704 (C=O), 1651 (amide I), 1531 (amide II), 1277, 1180, 1117, 976, 720 cm–1. Mass-spectrum: m/z: 809.62. (M+H)$^+$ (C$_{46}$H$_{86}$N$_2$O$_7$P requires 809.62).

D-erythro-2-N-Palmitoylsphinganine-1-phosphorylcholine-(N-Palmitoyl-dihydro-sphingomyelin) (17b). To a solution of 3-O-benzoyldihydrosphingomyelin (16b) (1.97 g, 2.38 mmol) in methanol (35 mL) was added a 2M sodium methoxide solution in methanol (3.5 mL). The reaction mixture was allowed to stir at 20–25° C. for 2–3 h, then neutralized with acetic acid and concentrated in vacuo. The residue was washed with acetone and the crude product was purified via an Amberlite MB-3 column using a mixture of chloroform-methanol-water (7:7:1 (50 mL)).

Yield=1.58 g (91.9%), monohydrate of (17b). Mp 220–221° C., R$_f$=0.36 (CHCl$_3$-methanol-acetic acid-water, 100:50:16:8). [α]$_D^{25}$+24.04° (c=0.92, CHCl$_3$-MeOH, 1:1).

IR (in mineral oil): 3286 (NH and OH), 1641 (amide I), 1549 (amide II), 1229 (C-O of benzoate), 1087 and 1059 (PO$_3^-$), 970, 830, 721 cm$^{-1}$. Mass spectrum: m/z: 705.59. (M+H)$^+$ (C$_{39}$H$_{82}$N$_2$O$_6$P requires 705.59). Lit. mp 222–222° C., [α]$_D^{25}$+22.5° [Shapiro, D. *Chemistry of Sphingolipids*, Paris, 1969].

The synthesis of B-D-Glucuronocerebroside (27).

According to the procedure provided in Bollenback, G. N., et al., *J. of the American Chemical Society* 77: 3310–3315, the synthesis of B-D-tetra-O-acetylglucoronic acid methyl ester (20) was performed from D-glucoronolactone (18) in a yield of 32.4%, [α]$_D^{25}$+8.3° (c=2.26, CHCl$_3$). M.p. 175.0° C.

Mass spectrum: m/z: 377.11. (M+H)$^+$ (C$_{15}$H$_{21}$O$_{11}$ requires 377.11). Lit.: [α]$_D^{25}$+8.7° (c=1, CHCl$_3$), m.p. 176.5–178° C.

2,3,4-Tri-O-acetyl-D-glucoronic acid methyl ester (21). A mixture of β-acetoxy-glucuronic acid methyl ester (20) (4.9 g, 13.0 mmol) and hydrazine acetate (2.1 g, 22.8 mmol) in DMFA (100 mL) was stirred at room temperature for 1.5 h. The mixture was diluted with ethyl acetate (1 L, washed with brine, dried over magnesium sulfate, and concentrated in vacuo. The residue was chromatographed on silica gel (hexane-ether, 1:4, then ether), to give compound (21).

Yield=4.2 g (96.5%). R$_f$=0.40 (hexane-THF, 3:2). [α]$_D^{22}$+85.2° (c=1.01, chloroform). IR (in mineral oil): 3450, 1760, 890 (cm$^{-1}$). Mass spectrum: m/z: 341.11 (M+Li)$^+$ (C$_{13}$H$_{18}$O$_{10}$Li requires 341.11).

O-(2,3,4-Tri-O-acetyl-a-D-glucuronopyranosyl methylate)-trichloroacetimidate (22). To a solution of hemiacetal (21) (6.3 g, 18.9 mmol) in methylene dichloride (130 mL) were added trichloroacetonitrile (19.0 mL, 190 mmol) and potassium hydride (0.74 g, 72 mmol) and resulting reaction mixture was allowed to stir at room temperature. In 2–3 h the reaction mixture was filtered through Celite 500 and the filtrate was concentrated in vacuo. The residue was passed through short column of silica gel using ether as the eluent to give compound (21).

Yield=7.6 g (84.3%). R$_f$0.75 (ether). [a]$_D^{22}$+93.6° (c=1.0, chloroform). Mass spectrum: m/z: 484.02. (M+Li)$^+$ C$_{15}$H$_{18}$NO$_{10}$Li requires 484.02

1-O-B-D-Glucuronoyl-2N-palmitoylsphingosine (27). A mixture of 3-O-benzoylceramide (8a) (1.62 g, 2.52 mmol), imidate (22) (2.43 g, 5.07 mmol) and molecular sieves 4 Å (11.7 g) was dried in vacuo for 36–40 h. This mixture was taken up into methylene dichloride (75 mL), and a solution of borontrifluoride etherate in methylene dichloride (1:9, 8 mL, ~5 mmol) was added in 1 mL portions for 30 min at –50° C. The reaction mixture was allowed to stir at the same temperature for 5–6 h and stored in a refrigerator overnight. The next morning 2 g of sodium bicarbonate was added and in 15–20 minutes the reaction mixture was filtered through Celite 500 and the filtrate concentrated in vacuo. The residue was chromatographed on silica gel using a mixture hexane-ethyl acetate (2:1) to yield compound 23 [R$_f$ 0.40 (chloroform-methanol, 20:0.5).

Mass Spectrum, m/z: 964.63. (M+Li)$^+$ C$_{54}$H$_{87}$NO$_{13}$Li requires 964.63. Calculated %: C, 67.68; H, 9.15; N, 1.46. Found %: C, 67.46; H, 9.21; N, 1.43.], contaminated with 1-O-acetyl-3-O-benzoylceramide (25) [R$_f$ 0.50 (chloroform-methanol, 20:0.5. Mass spectrum, m/z: 690.57;] and 3-O-benzoylceramide (8a) (2.15 g). This mixture was dissolved in chloroform-methanol-water (7:7:1, 100 mL) and a 0.5 M solution of potassium hydroxide in methanol (40 mL) was added. The reaction mixture was allowed to stir at room temperature for 20–24 h. The potassium salt of compound (27) was separated by filtration, dissolved in a mixture of chloroform-methanol-water (7:7:1, 150 mL) and was shaken with Amberlyst 15 (500 mg) for 25–30 minutes. The resin was removed by the filtration, the filtrate was washed with water (3×50 mL) and concentrated in vacuo. The residue was chromatographed on silica gel using a mixture chloroform-methanol-acetic acid-water (100:20:12:5) as the eluent to yield 0.50 g (27.8%) of β-D-glucuronylceramide (27) as white solid. $R_f$=0.35 (chloroform-methanol-acetic acid-water, 100:20:12:5).

Mass spectrum: m/z: 712.54. (M−H)⁻ ($C_{40}H_{74}O_9$ requires 712.54).

EXAMPLE 2

Experimental Procedures for the Preparation of Terminally Polar Sphingolipids Coupling a protected alkynyl derivative to an oxazolidine aldehyde is an efficient and versatile preparation of sphingolipids with a polar terminus, such as an amine, hydroxyl, or carboxyl group. After the addition reaction, a terminal hydroxyl group is available for conversion into a variety of other functionality. These terminally polar sphingolipids are an important class of molecules because they can attach to a solid support creating an affinity column for enzymes (Raun, F., et al., *Tetrahedron Lett.*, 36: 6615, 1995; and Kozikowski, A., et al., *Tetrahedron Lett.*, 37: 3279, 1996). They are also interesting because they are structurally similar to a class of mycotoxins called the Fumonisins.

Figure 10:
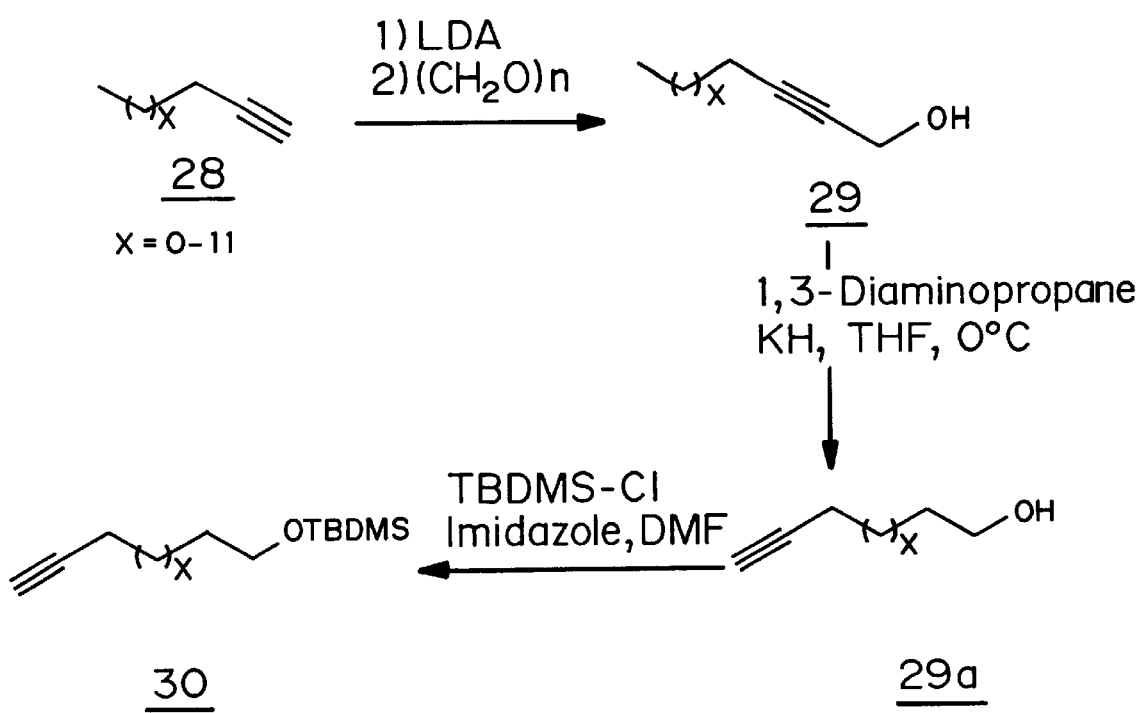
FIG. 10 is a schematic of one example of the preparation of an intermediate 4-pentyn-1-(1,1-dimethylethyl)-dimethylsilyl ether (30) which can be used in the synthesis of polar sphingolipids.

The synthesis of these molecules began with readily available alkynes (28), (FIG. 10). The treatment of the alkyne with lithium diisopropylamide (LDA) generated the alkynyllitheate which was then reacted with paraformaldyhyde to produce the propargyl alcohol (29). A contra thermodynamic acetylene-zipper reaction migrated the triple bond away from the hydroxyl group (29a)(Brown, C. A., et al., *J. Am. Chem. Soc.* 1975, 97, 891). Then 1,1-dimethylethyl-dimethyl-silyl (TBDMS) protection of the alcohol completed the preparation of the alkynol segment (Corey, E. J., et al., *J. Am. Chem. Soc.* 1972, 94, 6190). In a few instances, analogs of (30) were purchased directly.

Figure 11:
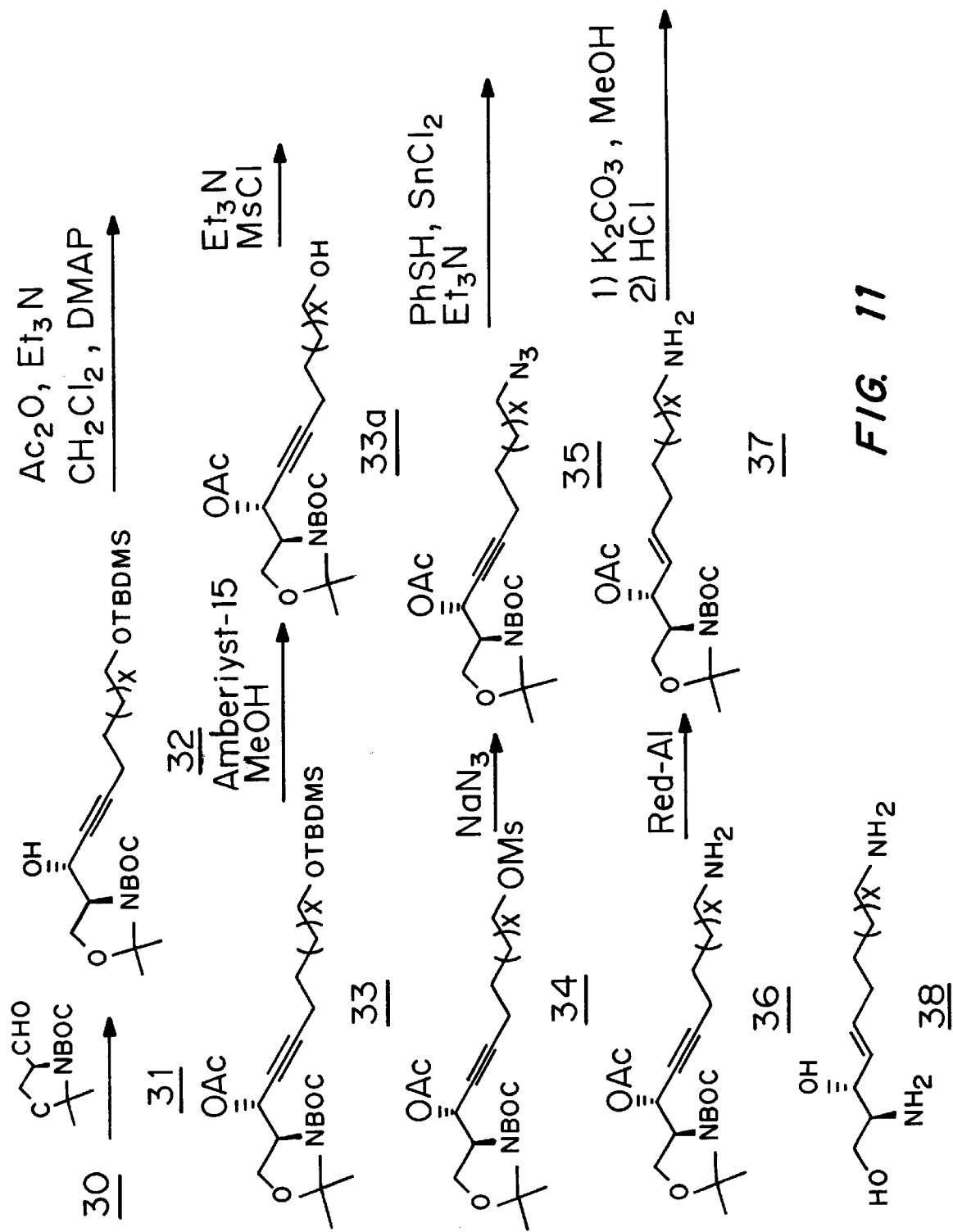
FIG. 11 is a schematic of the synthesis of sphingosine from key intermediate 4-pentyn-1-(1,1-dimethylethyl)-dimethylsilyl ether (30).

The oxazolidine aldehyde (31) was prepared according to a procedure by Garner (Garner, P. et al., *J. Org. Chem.*, 52: 2361, 1987). The coupling of protected alkynyl derivatives to (31) was accomplished by first producing the litheate of the alkyne with LDA and then slowly adding (31). The propargyl alcohol (32) was protected as the acetate by treating with triethylamine and acetic anhydride. The silyl ether was cleaved by stirring (33) in the presence of an acidic resin, Amberlyst-15. At this point, the compound (33a) may be modified in several ways: oxidation to produce the acid or ester, fluorination, elimination, or substitution. In order to attach the sphingolipid to a solid support, an amine terminus was desired. This functionality was introduced by first preparing the mesylate of (34) by adding triethylamine and methansulfonyl chloride. Displacement of the mesylate with sodium azide in DMF produced compound (35). Azide reduction with thiophenol, tin chloride, and triethylamine gives (36). Reduction of the triple bond with Red-Al efficiently produces the E isomer (37). The final steps in this synthesis were deprotection of the acetate with potassium carbonate in methanol (Plattner, J. J.; Gless, R. D.,; Rapoport, H., *J. Am. Chem. Soc.*, 94: 8613, 1972), and then removal of the acetonide and t-butoxy carbonyl (BOC) group with HCL to yield (38). This synthesis is illustrated in FIG. 11.

Experimental Procedures 2-nonyn-1-ol (40) (compound 29 where x=4). In a 250-mL flask equipped with a stir bar, I-Pr₂NH (7.34 g, 72.5 mmol) and THF (20 mL) were stirred under argon and cooled to 0° C. A 2.5-M solution of n-BuLi in toluene (29.0 mL, 72.5 mmol) was added slowly to the stirring solution. The reaction was stirred for 30 min at 0° C. and then cooled to −78° C. in a dry ice/acetone bath. Then 1-octyne was added slowly via syringe to the reaction and a white precipitate formed. To dissolve the precipitate, HMPA (23.6 g, 132 mmol) was added in one portion. The cloudy solution was stirred under argon at −78° C. for 30 minutes before warming to 0° C. when the precipitate dissolved. A solution of paraformaldehyde $(CH_2O)_n$ (5.94 g, 198 mmol) in THF (60 mL) was stirred under argon at −78° C. The alkynyl-litheate was then added via cannula with positive argon pressure to the $(CH_2O)_n$ solution. The reaction was then allowed to warm slowly to room temperature. The reaction was quenched with water and extracted with $Et_2O$. The organic layers were combined, washed with water and brine, dried with $MgSO_4$, and concentrated. This produced 24.4 g of orange oil. The product was purified with flash column chromatography on silica gel (10% $Et_2O$ in hexane) to give 5.07 g of amber oil (55%):

IR (neat) ν 3331, 2933, 2224 cm⁻¹, ¹H-NMR δ4.22 (t, 2H, J=2.0 Hz), 2.18 (m, 2H), 2.07 (s, 1H), 1.45 (m, 2H), 1.27 (m, 8H), 0.87 (t, 3H, J=6.9 Hz); ¹³C-NMRδ86.5, 78.3, 51.2 31.3, 28.5 (2C), 22.5 18.7, 14.0; MS m/z 147.08 (M⁺+Li). Anal. Calcd for $C_9H_{16}O$: C, 77.09; H, 11.50. Found: C, 76.93; H, 11.41.

2-pentadecyn-1-ol (41) (compound 29 where x=10). The same procedure for 2-nonyn-1-ol was followed with 1-tetradecyne (7.38 g, 38.0 mmol), I-Pr₂NH (4.23 g, 41.8 mmol), n-BuLi (16.7 mL of a 2.5-M solution, 41.8 mmol), HMPA (13.6 g, 76.0 mmol), and $(CH_2O)_n$ (3.42 g, 114 mmol). This produced 12.8 g of crude orange oil. The product was crystallized from hexane to yield 4.51 g of white solid (62%):

mp 40–42° C. IR (KBr) ν 3200, 2917, 2260 cm⁻¹; ¹H NMR δ 4.23 (t, 2H, J=2.0 Hz), 2.18 (m, 2H), 1.47–1.24 (m, bm, 20H), 0.86 (t, 3H, J=6.4 Hz); ¹³C-NMR δ 86.6, 78.2, 51.4, 31.9, 29.4 (2C), 29.3, 29.2, 28.5, 28.4(2C), 26.6, 22.7, 18.7, 14.1; MS m/z 231.19 (M⁺+Li). Anal. Calcd for $C_{15}H_{28}O$: C, 80.29; H, 12.58. Found: C, 80.36; H, 12.52.

8-nonyn-1-ol (42) (compound 30 where x=4). In a round-bottom flask equipped with a stir bar and under an atmosphere of argon was added KH (4.46 g, 111 mmol). The flask was cooled to 0° C. and 1,3-diaminopropane (50 mL) was added slowly via syringe. The solution was stirred for 45 min. Then 2-nonyn-1-ol, dissolved in of 1,3-diaminopropane (30 mL), was added dropwise via syringe to the stirring solution. The reaction was stirred for an additional 30 min at 0° C. before warming to room temperature overnight. The reaction was again cooled to 0° C. before quenching with water. The compound was extracted with $Et_2O$, washed with HCL, water, and brine, dried with $MgSO_4$, and concentrated. This produced 4.94 g of dark orange oil which was purified by flash column chromatography on silica gel (2.5% $Et_2O$ in hexane to 50% $Et_2O$ in hexane) to give 3.21 g of clear oil (67%): IR (near) ν 3409, 2931, 2242 cm⁻¹, ¹H—NMR δ 3.59 (t, 2H, J=7.0 Hz), 2.14 (td, 2H, J=3.0 Hz, 7.0 Hz), 2.10 (s, 1H), 1.91 (t, 1H, J=3.0 Hz), 1.50 (bm, 4H), 1.30 (bm, 6H); ¹³C—NMR δ 84.6, 68.1, 62.8, 32.6, 28.8, 28.6, 28.3, 25.6, 18.3; MS m/z 147.10 (M⁺+Li). Anal. Calcd for $C_9H_{16}O$: C, 77.09; H, 11.46. Found: C, 77.00; H, 11.46.

6-heptyn-1-ol (43)(compound 30 where x=2). The same procedure for 8-nonyn-1-ol was followed with 3-heptyn-1-ol (7.96 g, 71.0 mmol), KH (8.54 g, 21.3 mmol), and 1,3-diaminopropane (70 mL). It produced 5.86 g of clear yellowish liquid (74%): IR (neat) ν 3300, 2940, 2116 cm⁻¹; ¹H—NMR δ 3.52 (t, 2H, J=6.5 Hz), 2.93 (s, 1H), 2.11 (td, 2H, J=2.6 Hz, 6.8 Hz), 1.88 (t, 1H, J=2.6), 1.40–1.50 (bm, 6H); ¹³C—NMR δ 84.4, 68.3, 62.2, 32.0, 28.2, 24.8, 18.3

7-octyn-1-ol (44) (compound 30 where x=3). The same procedure for 8-nonyn-1-ol was followed with 3-octyn-1-ol (6.89 g, 54.6 mmol), KH (6.57 g, 16.4 mmol), and 1,3-diaminopropane (60 mL). This produced 6.09 g of clear yellowish liquid (88%): IR (neat)ν 3360, 2896, 2116 cm⁻¹; ¹H—NMR δ 3.44 (t, 2H, J=6.6 Hz), 3.27 (bs, 1H), 2.04 (td, 2H, J=2.6 Hz, 6.6 Hz), 1.83 (t, 1H, J=2.6 Hz), 1.39 (m, 4H), 1.25 (m, 4H); $^{13}$C NMR δ 84.5, 68.3, 62.2, 32.3, 28.3, 25.2, (2C), 18.2; MS m/z 136.00 (m$^+$+Li). Anal. Calcd for $C_8H_{14}O$: C, 76.14; H, 11.18. Found: C, 76.04; H, 11.16.

11-dodecyn-1-ol (45) (compound 30 where x=7). The same procedure for 8-nonyn-1-ol was followed with 9-dodecyn-1-ol (4.68 g, 25.7 mmol), KH(3.09 g, 77.0 mmol), and 1,3-diaminopropane (70 mL). This produced 4.33 g of yellow oil (93%): IR (neat) v 3317,2930, 2121 cm$^{-1}$; $^1$H—NMR δ 3.62 (t, 2H, J=6.6 Hz), 2.17 (td, 2H, J=2.6 Hz, 7.1 Hz), 1.93 (t, 1H, J=2.6 Hz), 1.76 (bs, 1H), 1.55 (m, 4H), 1.28 bm, 12H); $^{13}$C—NMR δ 84.8, 68.0, 63.0, 32.7, 29.5, 29.4 (2C), 29.0, 28.7, 28.4, 25.7, 18.4; MS m/z 189.18 (M$^+$+Li).

14-pentadecyn-1-ol (46) (compound 30 where x=10). The same procedure for 8-nonyn-1-ol was followed with 2-pentadecyn-1-ol (4.51 g, 20.1 mmol), KH (2.38 g, 59.4 mmol), and 1,3-diaminopropane (65 mL). This produced 3.18 g of white solid (70%): mp 42–44° C. IR (thin film( v 3430, 2926, 2252 cm$^{-1}$: $^1$H—NMR δ4.30 (t, 1H, J=5.0 Hz), 3.64 (t, 2H, J=6.6 Hz), 2.18 (td, 2H, J=2.6 Hz, 6.6 Hz), 1.94 (t, 1H, J=2.6 Hz), 1.49–1.26 (bm, 22H); $^{13}$C—NMR δ 84.8, 68.0, 63.1, 32.8, 29.6, (2C), 29.5 (2C), 29.4, 28.9, 28.5, 28.7, 28.0, 25.7, 18.4; MS m/z 231.53 (M$^+$+Li). Anal. Calcd for $C_{15}H_{28}O$: C, 80.29; H, 12.58. Found: C, 18.20; H, 12.50.

4-pentyn-1-(1,1-dimethylethyl)-dimethylsilyl ether (47) (compound 30 where x=0). A 100-mL flask equipped with a stir bar and septum was charged with 4-pentyn-1-ol (5.32 g, 63.2 mmol) and DMF (25 mL). The solution was stirred under argon and imidazole (10.8 g, 158 mmol), and then TBDMS-Cl (11.4 g, 75.8 mmol), was added. The reaction mixture was poured into water and extracted with Et$_2$O. The organic layers were combined, washed with water and brine, dried with MgSO$_4$, and concentrated. This produced 12.5 g of a yellow liquid. The compound was then vacuum distilled and yielded 9.21 g of clear liquid (74): IR (neat) v 3307, 2955, 2116 cm$^{-1}$; $^1$H—NMR δ 3.67 (t, 2H, J=5.8 Hz), 2.24 (td, 2H, J=2.6 Hz, 6.5 Hz), 1.90 (t, 1H, J=2.6 Hz), 0.86 (s, 9H), 0.03 (s, 6H); $^{13}$C—NMR δ 84.2, 68.2, 61.4, 31.5, 25.9, 25.7, 14.8, −5.4. Anal. Calcd for $C_{11}H_{22}OSi$: C, 66.60; H, 11.18. Found: C, 66.50; H, 11.10.5-hexyn-1-(1,1-dimethylethyl)-dimethylsilyl ether (48) (compound where x =1). The same procedure for 4-pentyn-1-(1,1-dimethylethyl)-dimethylsilyl ether was followed with 5-hexyn-1-ol (5.69 g, 58.0 mmol), imidazole (9.87 g, 145 mmol), and TBDMS-Cl (10.5, g, 69.6 mmol). This produced 9.44 g of clear liquid (77%): IR (neat) v 3314, 2944, 2125 cm$^{-1}$; $^1$H—NMR δ 3.62 (t, 2H, J=5.8 Hz), 2.20 (m, 2H), 1.92 (t, 1H, J=2.6 Hz), 1.60 (m, 4H), 0.88 (s, 9H), 0.04 (2, 6H); $^{13}$C—NMR δ 84.4,68.2, 62.5, 31.8, 25.9, 25.6, 24.9, 18.2, −5.3. Anal. Calcd for $C_{12}H_{24}OSi$: C, 67.86; H, 11.39. Found: C, 68.05; H, 11.38.

6-heptyn-1-(1,1-dimethylethyl)-dimethylsilyl ether (49) (compound 30 where x=2). The same procedure for 4-pentyn-1-(1,1-dimethylethyl)-dimethylsilyl ether was followed with 5-heptyn-1-ol (t, 5.86 g, 52.2 mmol), imidazole (8.89 g, 131 mmol), and TBDMS-Cl (9.44 g, 62.7 mmol). This produced 8.16 g of clear liquid (69%): IR (neat) v 3311, 2926, 2116 cm$^{-1}$; $^1$H—NMR δ 3.59 (t, 2H, J=5.8 Hz), 2.16 (td, 2H, J=2.6 Hz, 6.6 Hz), 1.90 (t, 1H, J=2.6 Hz), 1.50 (bm, 6H), 0.87 (s, 9H), 0.02 (s, 6H); $^{13}$C—NMR δ 84.4, 68.2, 62.9, 62.2, 32.3, 28.3, 26.0, 25.8, 25.0, 18.4, −5.5; MS m/z 227.93 (M$^+$+H). Anal. Calcd for $C_{13}H_{26}OSi$: C, 68.96; H, 11.57. Found: C, 68.92; H, 11.46.

7-octyn-1-(1,1-dimethylethyl)-dimethylsilyl ether (50) (compound 30 where x=3). The same procedure for 4-pentyn-1-(1,1-dimethylethyl)-dimethylsilyl ether was followed with 7-octyn-1-ol (5.77 g, 45.7 mmol), imidazole (7.79 g, 114 mmol), TBDMS-Cl (8.27 g, 54.9 mmol). The compound was purified by flash column chromatography on silica gel (25% Et$_2$O in hexane to 50% Et$_2$O in hexane) to give 10.73 g of clear liquid (98%): IR (neat) v 3310, 2926, 2119 cm$^{-1}$; $^1$H—NMR δ 3.60 (t, 2H, J=7.5 Hz), 2.17 (td, 2H, J=2.6 Hz, 6.8 Hz), 1.91 (t, 1H, J=2.6 Hz), 1.51 (bm, 4H), 1.35 (bm, 4H), 0.88 (s, 9H), 0.03 (s, 6H); $^{13}$C—NMR δ 84.6, 68.1, 63.1, 32.7, 28.5, 26.0, 25.9, 25.7, 25.3, 18.3 −5.4; MS m/z 241.37 (M$^+$+H). Anal. Calcd for $C_{14}H_{28}OSi$: C, 69.93; H, 11.74. Found: C, 69.76; H, 11.60.

8-nonyn-1-(1,1-dimethylethyl)-dimethylsilyl ether (52) (compound 30 where x=4). The same procedure for 4-pentyn-1-(1,1-dimethylethyl)-dimethylsilyl ether was followed with 8-nonyn-1-ol (2.99 g, 21.33 mmol), imidazole (3.63 g, 53.3 mmol), and TBDMS-Cl (38.6 g, 25.6 mmol). The compound was purified by flash column chromatography on silica gel (10% Et$_2$O in hexane) to give 4.53 g of pale yellow oil (83%): IR (neat) v 3313, 2930, 2217 cm$^{-1}$; $^1$H—NMR δ 3.59 (t, 2H, J=6.6 Hz), 2.17 (td, 2H, J=2.6 Hz, 7.0 Hz, 7.0 Hz)), 1.92 (t, 1H, J=2.6 Hz), 1.50 (m, 4H), 1.30 (bm, 6H), 0.88 (s, 9H), 0.04 (s, 6H); $^{13}$C—NMR δ 84.8, 68.2, 63.2, 32.8, 28.9, 28.7, 28.4, 26.1, 25.9, 25.7, 18.4, −5.3. Anal. Calcd for $C_{15}H_{30}OSi$: C, 70.80; H, 11.88. Found: C, 70.69; H, 11.76.

10-undecyn-1-(1,1-dimethylethyl)-dimethylsilyl ether (52) (compound 30 where x=6). The same procedure for 7-octyn-1-(1,1-dimethylethyl)-dimethylsilyl ether was followed with 10-undecyn-1-ol (6.73 g, 40.0 mmol), imidazole (6.80 g, 99.9 mmol), TBDMS-Cl (7.23 g, 48.0 mmol). This produced 7.58 g of clear liquid (67%): IR (neat) v 3315, 2926, 2119 cm$^{-1}$; $^1$H—NMR δ 3.56 (t, 2H, J=7.0 Hz), 2.14 (td, 2H, J=2.5 Hz, 7.0 Hz), 1.89 (t, 1H, J=2.5 Hz), 1.47–1.26 (bm, 14H), 0.86 (s, 9H), 0.01 (s, 6H); ⁻C—NMR δ 84.6, 68.0, 63.2, 32.8, 29.4, 29.3 (2C), 29.0, 28.7, 28.5, 25.9, 25.8, 18.3, −5.3 MS/ m/z 283.24 (M$^+$+H). Anal. Calcd for $C_{17}H_{32}OSi$: C, 72.27; H, 12.13. Found: C, 72.38; H, 12.05.

11-dodecyn-1-(1,1-dimethylethyl)-dimethylsilyl ether (53) (compound 30 where x=7) The same procedure for 4-pentyn-1-(1,1-dimethylethyl)-dimethylsilyl ether was followed with 11 -dodecyn-1-ol (4.28 g, 23.5 mmol), imidazole (4.00 g, 58.7 mmol), TBDMS-Cl (4.25 g, 28.2 mmol). This produced 4.97 g of clear liquid (71%): IR (neat) v 33158, 2935, 2120 cm$^{-1}$; $^1$H—NMR δ3.59 (t,2H, J=6.6 Hz), 2.17 (td, 2H, J=2.6 Hz, 7.1 Hz), 1.93 (t, 1H, J=2.6 Hz), 1.50 (bm, 6H), 1.27 (bm, 10H), 0.89 (s, 9H), 0.04 (s, 6H); $^{13}$C—NMR δ 84.8, 68.0, 63.3, 32.9, 29.6, 29.4 (2C), 29.1, 28.8, 28.5, 26.0, 25.8, 22.7, 18.4, −5.3 MS m/z 297.35 (M$^+$). Anal. Calcd for $C_{18}H_{36}OSi$: C, 72.90; H, 12.24. Found: C, 72.99; H, 12.19.

14-pentadecyn-1-(1,1-dimethylethyl)-dimethylsilyl ether (54) (compound 30 where x=10). The same procedure for 7-octyn-1-(1,1-dimethylethyl)-dimethylsilyl ether was followed with 14-pentadecyn-1-ol (3.16 g, 14.1 mmol), imidazole (2.40 g, 35.2 mmol), TBDMS-Cl (2.55 g, 16.9 mmol). This produced 4.28 g of clear oil (90%): IR (neat) v 3312, 2927, 2117 cm$^{-1}$; $^1$H—NMR δ 3.59 (t, 2H, J=6.5 Hz), 2.16 (td, 2H, J=2.5 Hz, 6.5 Hz), 1.92 (t, 1H, J=2.5 Hz), 1.50 (bm, 8H), 1.25 (bm, 18H), 0.88 (s, 9H), 0.04 (s, 6H); $^{13}$C—NMR δ 84.7, 68.0, 63.3, 32.9, 29.6 (4C), 29.5, 29.4, 29.1, 28.8, 28.5, 26.0, 25.8, 18.4 (2C), −5.3; MS m/z 339.44 (M$^+$+H). Anal. Calcd for $C_{21}H_{42}OSi$: C, 74.48; H, 12.50. Found: C, 74.56; H, 12.41.

Coupling reaction (55) (compound 32 where x=0). A three necked flask equipped with a low temperature thermometer, stir bar, and septa was charged with I-Pr$_2$NH (1.12 g, 11.1 mmol) and THF (50 mL). The solution was cooled to 0° C. and stirred under nitrogen before n-BuLi (4.44 mL of a 2.5-M solution in hexane, 11.1 mmol) was slowly added. After stirring for 30 min, the solution was cooled to −78° C. in a dry ice/acetone bath. Then 4-pentyn-1-(1,1-dimethylethyl)-dimethylsilyl ether 4$_0$, which was dissolved in THF (10 mL) was slowly added via syringe in a manner to keep the temperature below −70° C. This solution was stirred for 30 min at −78° C., then warmed to 0° C. for 30 min, and then back down to −78° C. This solution was added via cannula over 1 h to a stirring solution of the oxazolidine aldehyde 5 (2.08 g, 9.07 mmol) in THF (10 mL) at −78° C. with positive nitrogen pressure. The reaction was stirred for 1 h before quenching with water and extracting with Et$_2$O. The organic layers were washed with brine, dried with MgSO$_4$, and concentrated. This produced 5.56 g of cloudy-amber oil. The compound was then purified flash column chromatography on silica gel (10% Et$_2$O in hexane) to give 2.92 g of clear oil (68%): IR (neat) ν 3459, 2935, 2232, 1740 cm$^{-1}$; $^1$H—NMR δ 4.73 (m,05H), 4.46 (m, 0.5H), 4.04 (m, 3H), 3.87 (bm, 1H), 3.62 (t, 3H, J=6.0 Hz), 2,25 (td, 2H, J=1.0 Hz, 7.0 Hz), 1.65 (m, 2H), 1.47 (bs, 6H), 1.46 (bs, 9H), 0.85 (s, 9H), 0.01 (s, 6H); $^{13}$C—NMR δ 94.9, 61.5, (2C), 31.7, 31.6, 28.4 (2C), 28.2, 25.9, (2C), 25.7, 18.3, 15.2, −5.4.

Acetate protection (56) (compound 33 where x=0). To a 100-mL flask equipped with a stir bar and septum was added the oxazolidine alkyne (55) (2.89 g, 6.75 mmol) and CH$_2$Cl$_2$ (50 mL). The solution was stirred under a nitrogen atmosphere at room temperature when Et$_3$N (1.71 g, 16.9 mmol) and then Ac$_2$O (9.827 g, 8.10 mmol) were added dropwise. A catalytic amount of DMAP (10 mg) was added and the reaction was stirred for 24 h. The reaction was poured into water and extracted with Et$_2$O. The organic layers were combined, washed with water and brine, dried with MgSO$_4$, and concentrated. This produced 2.92 g of amber oil. The compound was purified by flash column chromatography on silica gel (10% Et2O in hexane) to give 2.29 g of clear oil (72%): IR (neat) ν 2947, 2234, 1761, 1704 cm$^{-1}$; $^1$H—NMR δ 5.84 (d, 1H, J=1.8 Hz), 4.00–4.30 (bm, 3H), 2,27 (td, 2H, J=1.2 Hz, 7.0 Hz), 3.64 (t, 2H, J=5.8 Hz), 2.08 (s, 3H), 1.68 (m, 2H), 1.53 (bs, 6H), 1.47 (bs, 9H), 0.87 (s, 9H), 0.03 (s, 6H); $^{13}$C—NMR δ 160.1, 64.3, 63.0, 61.4, 61.3, 59.9, 31.3, 28.3 (2C), 25.9 (2C), 25.7, 23.3, 21.1, 18.3, 15.1, −5.4. Anal. Calcd for C$_{24}$H$_{43}$O$_6$NSi: C, 61.37; H, 9.23; N, 2.98. Found: C, 61.50; H, 9.20; N, 3.01.

Desilylation (57) (compound 34 where x=0). The acylated oxazolidine alkyne (56) (2.17 g, 4.61 mmol) was dissolved in MeOH (40 mL) in a 100 mL-flask. The solution was stirred with a magnetic stir bar under a nitrogen atmosphere and cooled to 0° C. Amberlyst-15 was washed with MeOH (20 mL) on a fritted glass funnel before being added to the solution in one portion. The reaction was stirred at 0° C. for 45 min before being warmed to room temperature and stirred for an additional hour. The reaction was filtered through celite and concentrated to give 1.85 of pale yellow oil. The compound was purified by flash chromatography on silica gel (25% EtOAc in hexane) to give 1.32 g of amber oil (80%): IR (neat) ν 3478, 2978, 2239, 1752, 1700 cm$^{-1}$; $^1$H—NMR δ 5.79 (bs, 1H), 4.26–4.00 (bm, 3H), 3.70 (t, 2H, J=6.1 Hz), 2.32 (m, 2H), 2.09 (s, 3H), 1.75 (bm, 2H), 1.53 (s, 3H), 1.50 (s, 3H), 1.46 (s, 9H); $^{13}$C—NMR δ 150.0, 81.7, 80.6, 64.3, 63.9, 33.2, 63.0, 61.4, 59.8, 31.0, 30.8, 28.3, 26.7, 25.7, 23.2, 21.1, 15.2. Anal. Calcd for C$_{18}$H$_{29}$O$_6$N: C, 60.83; H, 8.22; N, 3.94. Found: C, 60.91; H, 8.17; N, 3.88.

N-Palmitoyl-FB$_1$: FB$_1$ (1mg, 1.38 μmol) and 4.4 mg of palmitic anhydride (6.92 μmol) were dissolved in 1 ml of methanol (MeOH):CHCl$_3$ (1:1). The mixture was kept at room temperature for up to 48 hr. The reaction was checked by TLC using silica 60 TLC plates and CHCl$_3$:MeOH:H$_2$O (90:20:0.5) as solvent system. To detect fumonisins, the plates were sprayed with a 0.5% p-anisaldehyde solution in MeOH:acetic acid:sulfuric acid (85:10:5), heated to 100° C. for 10 minutes, and visually examined. The clean-up was carried out by extraction with n-butanol as described for the ceramide synthase assay of FB$_1$. Results: yield 40–50%, ESI-MS: m/z 960.6 [M+H]+.

N-Palmitoyl-AP$_1$: AP$_1$(the product of removal of the tricarballylic acids from FB$_1$) (0.91 mg, 2.67 μmol) and 5.3 mg of palmitic anhydride (10.68 μmol) were dissolved in 1.5 ml of MeOH:CHCl$_3$ (1:1). The mixture was kept at room temperature for up to 48 hr. The reaction was checked by TLC as described above. The reaction mixture (0.5 ml) was applied to a SiO$_2$ SPE column (waters, 500 mg capacity), which was preconditioned with CHCl$_3$. The minicolumn was washed with 6 ml of CHCl$_3$ followed by 6 ml of CHCl$_3$/MeOH (95:5). PAP$_1$ was finally eluted with 6 ml of CHCl$_3$/MeOH (95:10). Results: yield 70–80%; FAB-MS (NBA-Li-Matrix): m/z 650.5 [M+Li]+, ESI-MS: m/z 644.8= [M+H]+.

BIOLOGICAL ACTIVITY

Biological Activity of Synthetic Glucuronoylceramide

Glucornoylceramide (GluAcCer), a ceramide with a glucuronic acid headgroup was synthesized according to the methods described above. The metabolism of GluAcCer requires β-glucuronidase, an enzyme found in bacteria but not in human intestinal cells. Accordingly, dietary GluAcCer cannot be digested in the small intestine but should be hydrolyzed in the colon by the colonic microflora. This digestion would result in releasing the same metabolites as seen from the other dietary sphingolipids, namely ceramide and sphingosine. The ability of GluAcCer to be cleaved by bacterial enzymes was established using β-glucuronidase from E. coli (Sigma) assayed according to the supplier's instructions.

Figure 12:
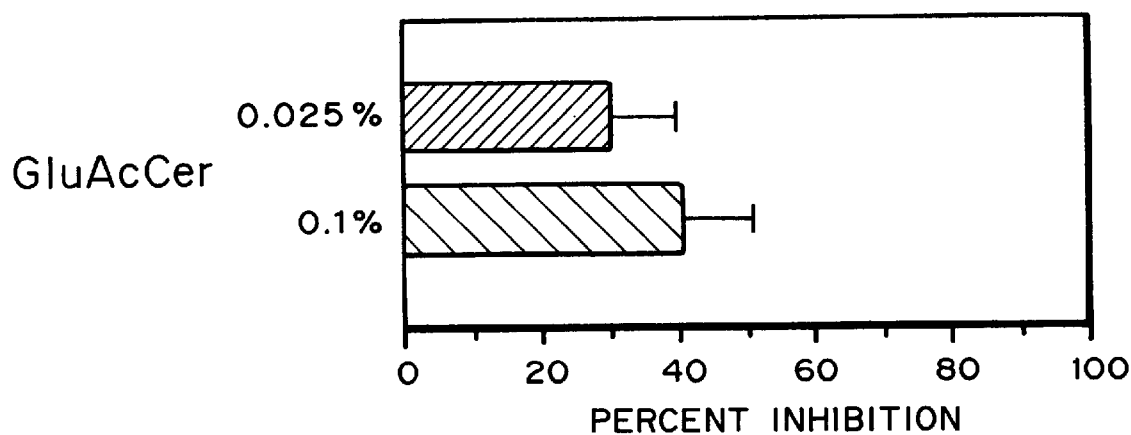
FIG. 12 is a bar chart graph of the percent inhibition of aberrant crypt foci formation by glucuronoylceramide as a function of percent of glucuronoylceramide in the diet in mice.

To evaluate the efficacy of GluAcCer in the suppression of the early stages of colon cancer, a model of chemically induced colon cancer was used. Female CF1 mice were injected with DMH to initiate colonic tumors. After initiation, the mice were fed and AIN 76A diet supplemented with GluAcCer (0.025 or 0.1% of the diet). The control group was fed the AIN 76A diet without supplements (one group without DMH and the other with DMH only). After four weeks, the mice were killed, the colons excised, and evaluated for the appearance of ACF. Both groups fed the supplemented diet showed fewer ACF than the control group (21 ±2.94, and 19.2±3.09 in the groups fed 0.025 and 0.1% GluAcCer in the diet, respectively, versus 30.2±4.19 in the control). The data demonstrate the GluAcCer inhibited ACF formation by 20–30% (FIG. 12).

Figure 13A:
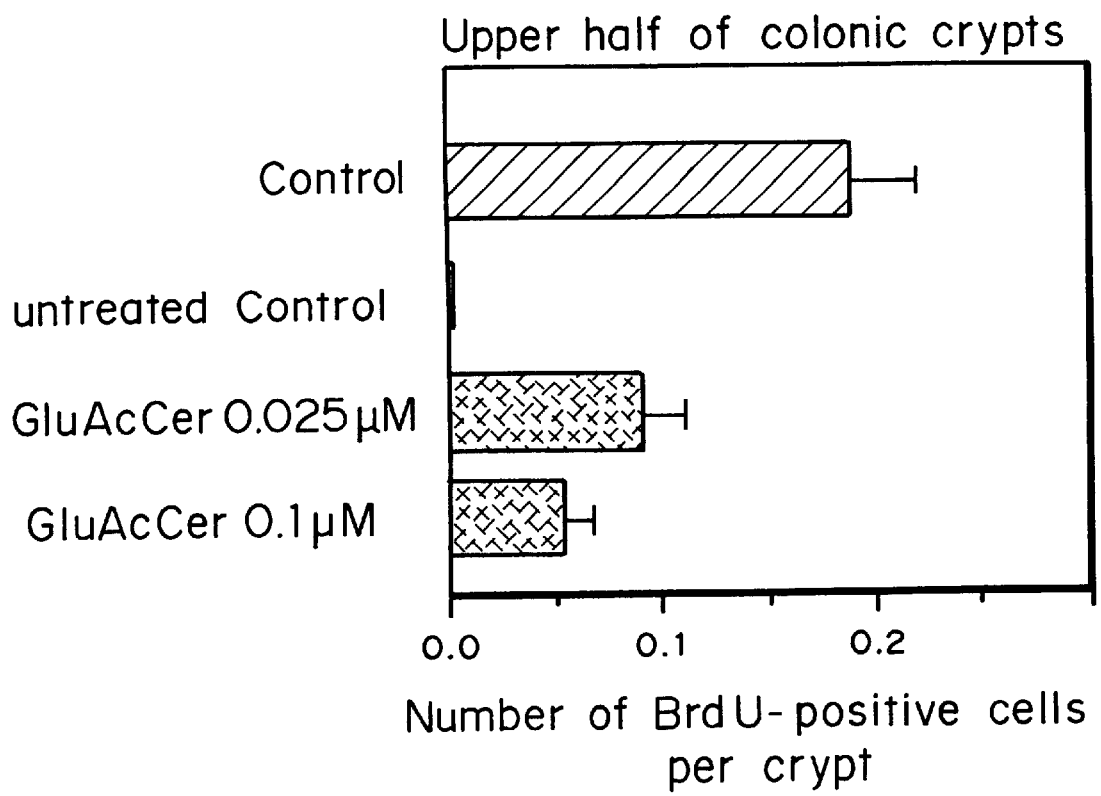
FIGS. 13a and b are bar chart graphs of the reduction of cell proliferation by glucuronoylceramide as a function of percent of glucuronoylceramide in the diet in mice in the upper half of colonic crypts (13a) and the lower half of colonic crypts (13b).
Figure 13B:
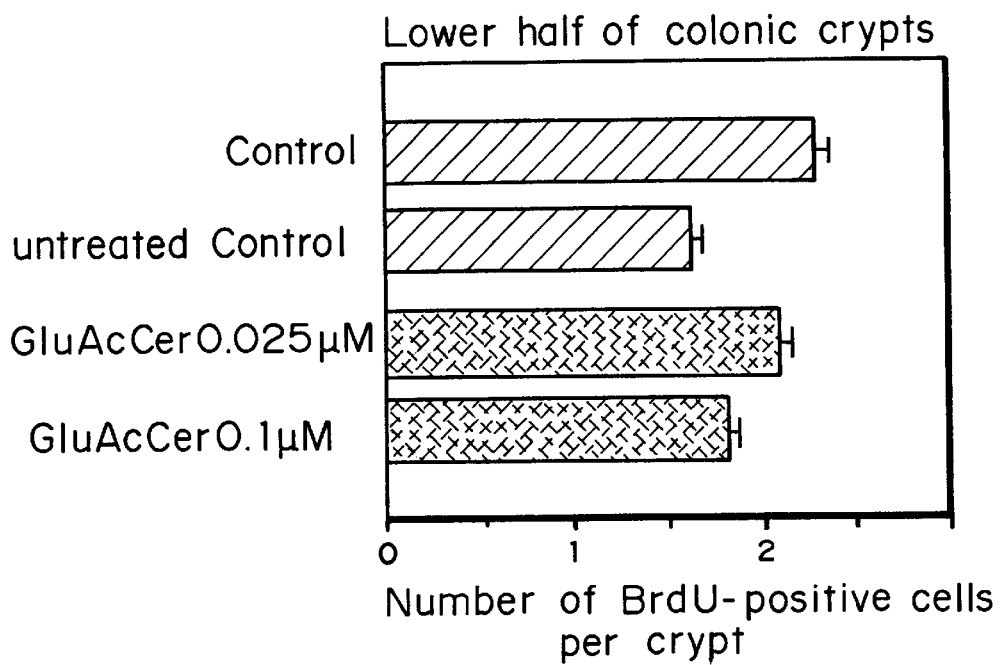

The effect of GluAcCer on cell proliferation was also investigated since a deregulation of cell growth is observed in carcinogenesis. GluAcCer at 0.15 reduced the proliferation in the lower half of the colonic crypts, but more importantly, both concentrations reduced proliferation in the upper half of the crypts in a dose dependent manner (FIGS. 13a and 13b). Therefore, feeding synthetic GluAcCer to mice suppresses the formation of early stages in colon carcinogenesis, possibly by restricting the proliferation to the lower half of the colonic crypt.

Induction of Cell Death by Sphingolipids

The activity of sphingosine, sphinganine and 1-deoxy-5-hydroxy-sphinganine in a human colon cancer cell line was investigated. The structures of the tested compounds appear below.

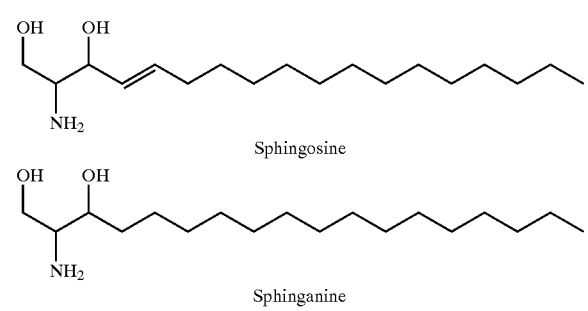

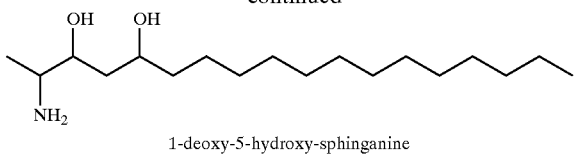

1-deoxy-5-hydroxy-sphinganine

Figure 14:
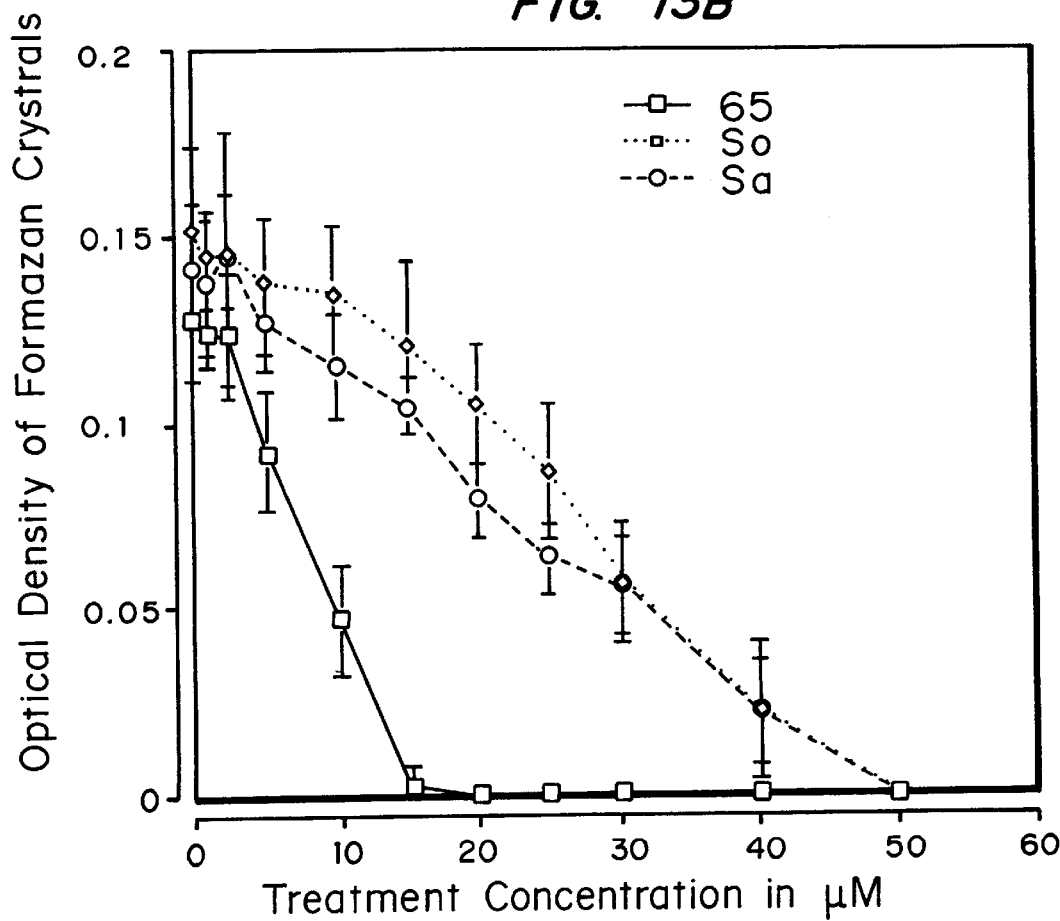
FIG. 14 is a graph of treatment concentration in micromolar of sphingosine, sphinganine and 1-deoxy-5-hydroxy-sphinganine versus the optical density of formazan crystals as a means to illustrate the induction of cell death by sphingolipids as shown by MTT assay.

An MTT assay was used to determine the cytotoxicity of the compounds shown above. Only cells with intact mitochondria are able to form formazane crystals, whereas late apoptotic and necrotic cells are not. The optical density of formazane crystals is used to infer cell viability. A 15 μM treatment of 1-deoxy-5-hydroxy-sphinganine results in nearly 100% cell death in HT-29 cells after 24 hours. A 50 um treatment of sphingosine and a 50 uM treatment of sphinganine were required to produce comparable cell death in HT-29 cells after 24 hours. As a result, it was concluded that (a) sphinganine and sphingosine show similar cytotoxicity in HT-29 cells, and (b) 1-deoxy-5-hydroxy-sphinganine is at least twice as potent in inducing cell death in HT-29 cells as sphingosine and sphinganine. The results of this assay are shown in FIG. 14.

Pharmaceutical Compositions

Mammals, and specifically humans, suffering from any of the above-described conditions can be treated by the topical or systemic administration to the patient of an effective amount of one or more of the compounds described herein, including a sphingolipid metabolism altering compound, or pharmaceutically acceptable salt, optionally in the presence of a pharmaceutically acceptable carrier or diluent.

The sphingolipid compound is administered subcutaneously, intravenously, intra peritoneally, intramuscularly, parenterally, orally, submucosally, by inhalation, transdermally via a slow release patch or topically, in an effective dosage range to treat the target condition. Typical systemic dosages for all of the herein described conditions are those ranging from 0.1 mg/kg to 500 mg/kg of body weight per day as a single daily dose or divided daily doses. Typical dosages for topical applications are those ranging from 0.001 to 100% by weight of the active compound.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compounds in vivo in the absence of serious toxic effects.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound for systemic delivery is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound or its salts can be administered as a component of an elixir, suspension, syrup, wafer, chewing gum or the like. A syrup may contain, in addition to the active compounds, sucrose as a sweetening agent and certain preservatives, dyes and colorings and flavors.

The compound can also be mixed with other active materials which do not impair the desired action, or with materials that supplement the desired action, such as antibiotics, antifungals, antiinflammatories, antivirals, or other immunosuppressive agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid of sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

If administered intravenously, preferred carriers are physiological saline, bacteriostatic water, Cremophor EL™ (BASF, Parsippany, N.J.) or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients, and stabilizers can be used to prepared topical compositions. Examples of thickening agents include petrolatum, beeswax, xanthan gum, or polyethylene, humectants such as sorbitol, emollients such as mineral oil, lanolin and its derivatives, or squalene. A number of solutions and ointments are commercially available, especially for ophthalmic applications.

Modifications and variations of the present invention will be obvious to those skilled in the art from the foregoing description of the invention. Such modifications and variations are intended to come within the scope of the appended claims.

What is claimed is:
1. A sphingolipid derivative of the formula:

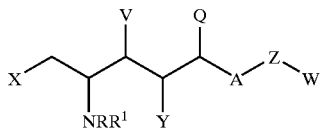

wherein
  A is a spacer group which is $(CH_2)_m$ where m=0–14, where any of the hydrogens may be independently replaced by $R^1$ or X and where any two adjacent carbons may be independently replaced by a $C_3$–$C_8$ cycloalkyl group, a 1,2-, 1,3-, or 1,4-disubstituted benzene group, or a 2,3- 2,4-, or 2,5-disubstituted thiophene, furan or pyrrole group;
  Y, V and Q are independently hydrogen, $OR^1$, $NR_2$, CN, alkyl, acyl or carboxylate, and wherein alternatively, V and Y or Y and Q can together constitute a double or triple bond;
  X is hydrogen;
  W=no substituent, H, alkyl, aryl, alkenyl, alkynyl, alkaryl, aralkyl, $C(O)(CH_{2I\ y})_nCO_2H$, $C(O)(CH_2)_nCW'_2CO_2H$ or $OR^1$;
  W' is selected independently from H, alkyl, aryl, $(CH_2)_nCO_2H$; $(CH_2)_nCH(CO_2H)$—$CH_2CO_2H$; and $(CH_2)_nCH(CO_2H)CH(CH_2CO_2H)CO_2H$;
  Z is H, O, NH, NR, NHC(O), $CO_2$, C(O)NH or C(O)NR;
  R is selected independently from H, alkyl, acyl, alkenyl, alkynyl, aryl, alkaryl, aralkyl or heteroaryl;
  $R^1$ is R or $R^2$;
  $R^2$ is β-D-galatoside, N-acetyl-β-D-glucosamine, α-D-mannoside, β-D-cellobioside, β-D-glucopyranoside, β-D-galatopyranoside, β-D-glucuronide, starch, lactose, raffinose, stachyose, fructo-oligo-saccharide, or amide or ester of β-cyclodextrin, or dextran linked via succinate or glutarate, or furanose or pyranose carbohydrate;
  wherein there is at least one $R^2$ substituent in the sphingolipid derivative.

2. The compound of claim 1, wherein $R^2$ is selected from the group consisting of β-glucuronide, β-D-galactoside; N-acetyl-β-D-glucosamine; α-D-mannoside; β-D-cellobioside; and β-D-glucopyranoside.

3. The compound of claim 1, wherein the bond between V and Y or Y and Q is a double bond.
4. The compound of claim 1, wherein Y is hydrogen.
5. The compound of claim 1, wherein V is $OR^2$.
6. The compound of claim 5, wherein V is O-β-D-galactoside.
7. The compound of claim 5, wherein V is O-β-D-glucuronide.
8. The compound of claim 5, wherein V is O-(N-acetyl-β-D-glucosamine).
9. The compound of claim 5, wherein V is O-α-D-mannoside.
10. The compound of claim 5, wherein V is O-β-D-cellobioside.
11. The compound of claim 5, wherein V is O-β-D-glucopyranoside.
12. The compound of claim 5, wherein V is O-β-D-galatopyranoside.
13. The compound of claim 5, wherein V is O-β-D-galatopyranoside.
14. The compound of claim 1, wherein Y is H and V is $OR^2$.
15. The compound of claim 14, wherein V is O-β-D-galatoside.
16. The compound of claim 14, wherein V is O-β-D-glucuronide.
17. The compound of claim 14, wherein V is O-(N-acetyl-β-D-glucosamine).
18. The compound of claim 14, wherein V is O-α-D-mannoside.
19. The compound of claim 14, wherein V is O-β-D-cellobioside.
20. The compound of claim 14, wherein V is O-β-D-glucopyranoside.
21. The compound of claim 14, wherein V is O-β-D-galatopyranoside.
22. The compound of claim 14, wherein V is O-β-D-galatopyranoside.
23. The compound of claim 1, wherein Q is $OR^2$.
24. The compound of claim 23, wherein Q is O-β-D-galatoside.
25. The compound of claim 23, wherein Q is O-β-D-glucuronide.
26. The compound of claim 23, wherein Q is O-(N-acetyl-β-D-glucosamine).
27. The compound of claim 23, wherein Q is O-α-D-mannoside.
28. The compound of claim 23, wherein Q is O-β-D-cellobioside.
29. The compound of claim 23, wherein Q is O-β-D-glucopyranoside.
30. The compound of claim 23, wherein Q is O-β-D-galatopyranoside.
31. The compound of claim 23, wherein Q is O-β-D-galatopyranoside.
32. The compound of claim 1, wherein Y is H and Q is $OR^2$.
33. The compound of claim 32, wherein Q is O-β-D-galactoside.
34. The compound of claim 32, wherein Q is O-β-D-glucuronide.
35. The compound of claim 32, wherein Q is O-(N-acetyl-β-D-glucosamine).
36. The compound of claim 32, wherein Q is O-α-D-mannoside.
37. The compound of claim 32, wherein Q is O-β-D-cellobioside.
38. The compound of claim 32, wherein Q is O-β-D-glucopyranoside.
39. The compound of claim 32, wherein Q is O-β-D-galatopyranoside.

40. The compound of claim 32, wherein Q is O-β-D-galatopyranoside.

41. A 1-deoxy-5-substituted-sphinganine derivative of the formula:

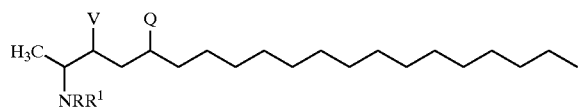

wherein

V and Q are independently $OR^1$;

$R^1$ is R or $R^2$;

R is selected independently from hydrogen, alkyl, acyl, alkenyl, alkynyl, aryl, alkaryl, aralkyl or heteroaryl;

$R^2$ is phosphate, β-D-galactoside, N-acetyl-β-D-glucosamine, α-D-mannoside, an organic azo-bond containing moiety that can be reduced by an azoreductase, β-D-cellobioside, β-D-glucopyranoside, β-D-galatopyranoside, β-D-glucoronide, starch lactose, raffinose, stachyose, fructo-oligo-saccharide, amide or ester of β-cyclodextrin, dextran linked via succinate or glutarate, amino acid, peptide, polyamino acid, polypeptide, furanose or pyranose carbohydrate, sulfonate (or an ester thereof), phosphocholine, phosphoserine or phosphoethanol-amine; p1 wherein there is at least one $R^2$ substituent in the sphinganine derivative.

42. Ceramide β-glucuronide, which has the chemical formula

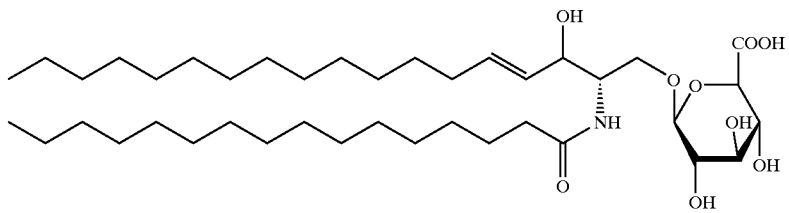

* * * * *